United States Patent
Kim et al.

(10) Patent No.: US 7,119,229 B2
(45) Date of Patent: Oct. 10, 2006

(54) ALKALOID DERIVATIVE AND A PHARMACEUTICAL COMPOSITION CONTAINING THE SAME

(75) Inventors: Wan Joo Kim, Seoul (KR); Kyoung Soo Kim, Kyunggi-do (KR); Myung Hwa Kim, Kyunggi-do (KR); Jong Yek Park, Kyunggi-do (KR); Jung Min Jang, Seoul (KR); Jae Won Choi, Seoul (KR); Dong Hoo Kim, Daegu (KR)

(73) Assignees: Chemtech Research Incorporation, (KR); KT & G Corporation, (KR)

( * ) Notice: Subject to any disclaimer, the term of this patent is extended or adjusted under 35 U.S.C. 154(b) by 163 days.

(21) Appl. No.: 10/479,057

(22) PCT Filed: May 27, 2002

(86) PCT No.: PCT/KR02/00996

§ 371 (c)(1),
(2), (4) Date: Nov. 26, 2003

(87) PCT Pub. No.: WO02/100824

PCT Pub. Date: Dec. 19, 2002

(65) Prior Publication Data

US 2004/0204494 A1    Oct. 14, 2004

(30) Foreign Application Priority Data

May 28, 2001 (KR) ................. 2001-29341

(51) Int. Cl.
C07C 233/05 (2006.01)
A61K 31/165 (2006.01)

(52) U.S. Cl. .................. 564/162; 564/166; 564/176; 564/193; 564/211; 560/24; 514/617; 514/618; 514/619; 514/626; 514/628; 514/478

(58) Field of Classification Search ............. 564/162, 564/166, 176, 193, 211; 514/617, 618, 619, 514/626, 628, 478; 560/24
See application file for complete search history.

(56) References Cited

U.S. PATENT DOCUMENTS 3,222,253 A   12/1965   Eschenmoser et al.
4,533,675 A    8/1985   Brossi et al.

FOREIGN PATENT DOCUMENTS

FR    2002496    * 10/1969
WO    91/02084    2/1991

OTHER PUBLICATIONS

Shi, Quian, et al., "Antitumor Agents. 172. Synthesis and Biological Evaluation of Novel Deacetamidothiocolchicin-7-ols and Ester Analogs as Antitubulin Agents." *J. Med. Chem*, 1997, vol. 40, pp. 961-966. American Chemical Society, Washington, D.C.

Muzaffar, Anjum, et al., "Antitubulin Effects of Derivatives of 3-Demethylthiocoichicine, Methylthio Ethers of Natural Colchicinoids, and Thioketones Derived from Thiocolchicine. Comparison with Colchicinoids." *J. Med. Chem.*, 1990, vol. 33, pp. 567-571. American Chemical Society, Washington, D.C.

Kerekes, Peter, et al., "Synthesis and Biological Effects of Novel Thiocolchicines. 3. Evaluation of N-Acyldeacetylthiocolchicines, N-(Alkoxycarbonyl)deacetylthiocolchicines, and O-Ethyldemethylthiocolchicines. New Synthesis of Thiodemecolcine and Antileukemic Effects of 2-Demethyl- and 3-Demethylthiocolchicine." *J. Med. Chem.*, 1985, vol. 28, pp. 1204-1208, American Chemical Society, Washington, D.C.

Malkinson, Frederick D., "Colchicine: New Uses of an Old, Old Drug." *Arch Dermatol*, vol. 118, Jul. 1982, pp. 453-457. American Medical Association, Chicago, IL.

Boyé, Olivier, et al., "Tropoionic *Colchicum* Alkaloids and Allo Congeners." *The Alkaloids*. 1992, vol. 41, Chapter 3, pp. 125-176.

Andreu, Jose M., "Interaction of Tubulin with Bifunctional Colchicine Analogues: An Equilibrium Study." *Biochemistry*, 1984, vol. 23, pp. 1742-1752. American Chemical Society, Washington, D.C.

Pyles, Erica A., et al., "Effect of the B Ring and C-7 Substituent on the Kinetics of Colchicinoid-Tubulin Associations." *Biochemistry*, 1993, vol. 32, pp. 2329-2336. American Chemical Society, Washington, D.C.

(Continued)

*Primary Examiner*—Shailendra Kumar
(74) *Attorney, Agent, or Firm*—Buchanan Ingersoll PC

(57) ABSTRACT

Colchicine derivatives represented by the formula (I)

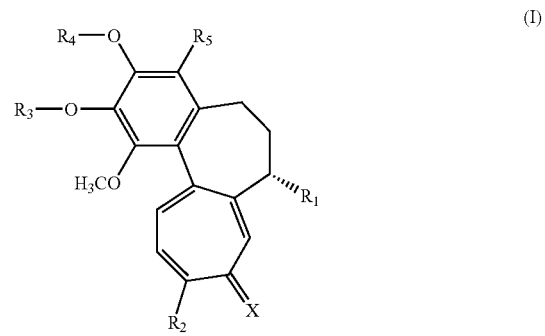

with a halogen or nitric ester group, or pharmaceutically acceptable salts thereof, are described. Pharmaceutical compositions containing the same as effective components are also described. The colchicine derivatives were found to have anticancer, anti-proliferous and immunosuppressive function. Methods for preparing the colchicines derivatives are also provided.

6 Claims, 5 Drawing Sheets

OTHER PUBLICATIONS

Williams, Robert F., et al., "A Photoaffinity Derivative of Colchicine: 6'-(4'-Azido-2'-nitrophenylamino)hexanoyldeacetylcochicine. Photolabeling and Location of the Colchicine-Binding Site on the α-Subunit of Tubulin." *The Journal of Biological Chemistry*, 1985, vol. 260, No. 25, pp. 13794-13800. The American Society of Biological Chemists, Inc., Baltimore, MD.

Ostermann, Daniel, et al., "Colchicine Allows Prolonged survival of Highly Reactive Renal Allograft in the Rat." *Journal of the American Society of Nephrology*, 1993, vol. 4, No. 6, pp. 1294-1299, The American Society of Nephrology, Washington, D.C..

Kang, Gil-Jong, et al., "N-Acetylcolchinol O-Methyl Ether and Thiocolchicine, Potent Analogs of Colchicine Modified in the C Ring: Evaluation of the Mechanistic Basis for Their Enhanced Biological Properties." *The Journal of Biological Chemistry*, 1990, vol. 265, No. 18, pp. 10255-10259. The American Society of Biochemistry and Molecular Biology, Inc., Baltimore, MD.

Quinn, Frank R., "Toxicity Quantitative Structure-Activity Relationships of Colchicines" *J. Med. Chem.*, 1981, vol. 24, pp. 636-639. American Chemical Society, Washington, D.C.

Quinn, Frank R., "Quantitative Structure-Activity Relationships of Colchicines against P388 Leukemia in Mice." *J. Med. Chem.*, 1981, vol. 24, pp. 251-256. American Chemical Society, Washington, D.C.

Hansch, Corwin, et al. "Antitumor Structure-Activity Relationships. Nitrosources vs. L-1210 Leukemia." *J. Med. Chem.*, 1980, vol. 23, pp. 1095-1101. American Chemical Society Washington, D.C.

Shiau, George T., et al. "Alkylthiocolchicines and N-Deacetyl-alkylthiocolchicines and Their Antileukemic Activity." *Journal of Pharmaceutical Sciences*, Apr. 1975, vol. 64, No. 4, pp. 646-648. American Pharmaceutical Association, Easton, PA.

Poulev, Alexander, et al. "Regioselective Bioconversion of Colchicine and Thiocolchicine into Their Corresponding 3-Demethyl Derivatives." *Journal of Fermentation and Bioengineering*, 1995, vol. 79, No. 1, pp. 33-38. Elsevier Science Inc., New York, NY.

Li, Leping, et al. "Antitumor Agents. 150. 2', 3', 4', 5', 5,6,7-Substituted 2-Phenyl-4-quinolones and Related Compounds: Their Synthesis, Cytotoxicity, and Inhibition of Tubulin Polymerization." *J. Med. Chem.*, 1994, vol. 37, pp. 1126-1135. American Chemical Society, Washington, D.C.

Andreu, Jose M., et al. "Interaction of Tubulin with Bifunctional Colchicine Analogues: An Equilibrium Study." *Biochemistry*, 1984, vol. 23, pp. 1742-1752. American Chemical Society, Washington, D.C.

Capraro, Hans-Georg, et al. "Simple Conversion of Colchicine into Demecolcine." *Helvetica Chimica Acta*, 1979, vol. 62, Fasc. 4, No. 99, pp. 965-970. Verlag Helvetica Chimica Acta, Basel, Switzerland.

Iorio, Maria A. "Contraction of Tropolonic Ring of Colchicine by Hydrogen Peroxide Oxidation." *Heterocycles*, 1984, vol. 22, No. 10, pp. 2207-2211. Elsevier, New York, NY.

Jang, H.J. "Comparison of Pancreas Transplantation Outcome Between the Cyclosporine and Tacrolimus Eras." *Transplantation Proceedings*, 2000, vol. 32, pp. 2470-2471. Elsevier Science Inc., New York, NY.

Guo, L., et al. "Role of Natural Killer Cells in Allograft Rejection." *Transplantation Proceedings*, 2000, vol. 32, pp. 2089-2090. Elsevier Science Inc., New York, NY.

Jang, H.J. et al. "Tacrolimus for Rescue Therapy in Refractory Renal Allograft Rejection." *Transplantation Proceedings*, 2000, vol. 32, pp. 1765-1766. Elsevier Science Inc., New York, NY.

Jang, H.J. et al. "Conversion from Cyclosporine to Tacrolimus in Renal Allograft Recipients with Delayed Graft Function from Severe Acute Tubular Necrosis." *Transplantation Proceedings*, 2000, vol. 32, pp. 1714-1715. Elsevier Science Inc., New York, NY.

* cited by examiner

ALKALOID DERIVATIVE AND A PHARMACEUTICAL COMPOSITION CONTAINING THE SAME

This application is a 371 of PCT/KR02/00996, filed May 27, 2002.

TECHNICAL FIELD

The present invention relates to a novel alkaloid derivative and a pharmaceutical composition containing the same. More particularly, the present invention relates to a novel colchicine derivative having anticancer, anti-proliferous and anti-inflammatory effects and immunosuppressive and muscle relaxing functions, and pharmaceutically acceptable salts thereof, a pharmaceutical composition containing the same as an effective component, and methods for preparing the same.

BACKGROUND ART

Colchicine is a pseudo-alkaloid widely used for treatment of gout and is used only for short-term therapeutic treatment due to its toxicity. However, colchicine has been reported to exhibit a very fast and specific therapeutic effect on gout, as described in the Alkaloids, 1991, vol. 41, 125–176, U.S. Pat. No. 4,533,675, and so on.

During cell division, colchicine inhibits formation of mitotic spindle, thereby suppresses cell division, leading to activation of anticancer and anti-proliferous effects. Also, continuous research into colchicine applications has been carried out and a variety of colchicine derivatives have been synthesized up to now, as described in U.S. Pat. No. 3,222,253, U.S. patent application Ser. No. 00/608073A, WO 91/02084, and so on. Among them, only demecolcine has been used for treatment of leukemia.

There is also a report that colchicine can be used for treatment of psoriasis or rheumatoid arthritis and has an amyloidosis inhibitory effect and an anti-inflammatory effect (*Arch. Dermatol.* 1982, Vol. 118, Jul., pp 453–457). Also, thiocolchicoside, which is one of colchicine derivatives, is widely used for treatment of skeletal muscle contracture and inflammation.

DISCLOSURE OF THE INVENTION

A first feature of the present invention is to provide a novel colchicine derivative having anticancer, anti-proliferous and anti-inflammatory effects and immunosuppressive and muscle-relaxing functions, and pharmaceutically acceptable salts thereof.

A second feature of the present invention is to provide methods for preparing the colchicine derivatives.

A third feature of the present invention is to provide a pharmaceutical composition containing the colchicine derivative and pharmaceutically acceptable salts thereof as an effective component.

In an aspect of the present invention, it is provided colchicine derivatives represented by the formula (1) and pharmaceutically acceptable salts thereof:

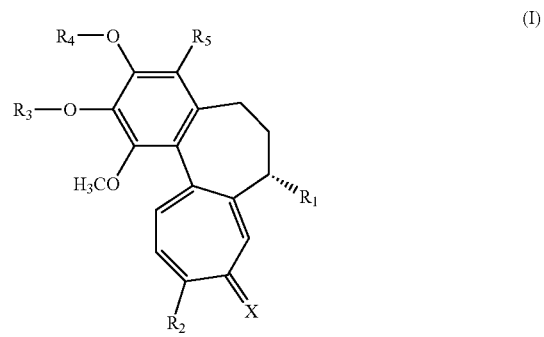

wherein when $R_1$ is $N(R_6)C(X_1)$-A, $X_2C(X_1)$-A, $N(R_6)$-A, $N(A)_2$ or $X_2$-A, $R_2$ is $X_3R_7$ or $N(R_7)_2$, $R_3$ and $R_4$ are independently hydrogen or a methyl group, $R_5$ is hydrogen, a methyl group or $CH_2X_4R_7$, wherein $R_6$ and $R_7$ are independently hydrogen or a lower alkyl, and X, $X_1$, $X_2$, $X_3$ and $X_4$ are independently O or S;

when $R_2$ is $N(R_6)C(X_1)$-A, $X_2C(X_1)$-A, $N(R_6)$-A, $N(A)_2$. or $X_2$-A, $R_1$ is $N(R_6)COCH_3$, $N(R_6)COCF_3$, or $NHC(O)OR$, $R_3$ and $R_4$ are independently hydrogen or a methyl group, $R_5$ is hydrogen, a methyl group or $CH_2X_4R_7$, wherein $R_6$ and $R_7$ are independently hydrogen or a lower alkyl, $R_8$ is a lower alkyl, alkenyl, or substituted or unsubstituted aryl, and X, $X_1$, $X_2$ and $X_4$ are independently O or S;

when $R_3$ and $R_4$ are independently $C(X_1)$-A or -A, $R_1$ is $N(R_6)COCH_3$, $N(R_6)COCF_3$, or $NHC(O)O_8$, $R_2$ is $X_3R_7$ or $N(R_7)_2$, $R_5$ is hydrogen, a methyl or $CH_2X_4R_7$, wherein $R_6$ and $R_7$ are independently hydrogen or a lower alkyl, $R_8$ is a lower alkyl, alkenyl, or substituted or unsubstituted aryl, and X, $X_1$, $X_3$ or $X_4$ are independently O or S;

when $R_5$ is $CH_2X_2C(X_1)$-A, $R_1$ is $N(R_6)COCH_3$, $N(R_6)COCF_3$ or $NHC(O)OR_8$, $R_2$ is $X_3R_7$ or $N(R_7)_2$, $R_3$ and $R_4$ are independently hydrogen or a methyl group, wherein $R_6$ and $R_7$ are independently hydrogen or a lower alkyl, $R_8$ is a lower alkyl, alkenyl, or substituted or unsubstituted aryl, and X, $X_1$, $X_2$ and $X_3$ are independently O or S, wherein A is represented by the formula (a), (b), (c), (d), (e), (f), (g), (h), (i) or (j):

—$Y_1$—Hal (a)

—$Y_1$—$ONO_2$ (b)

—(CH—$CH_2$—O)$n_1$—Hal (c)
    |
    $R_9$

—(CH—$CH_2$—O)$n_1$—$NO_2$ (d)
    |
    $R_9$

—$(CH_2)n_2$—CH—$(CH_2)n_3$—$CH_3$ (e)
          |
          Hal

—$(CH_2)n_2$—CH—$(CH_2)n_3$—$CH_3$ (f)
          |
          $ONO_2$

3

-continued

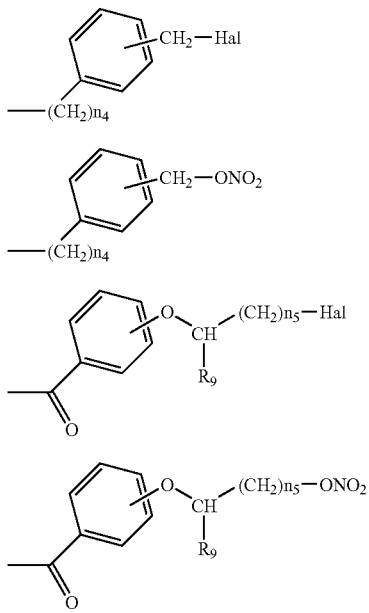

(g)

(h)

(i)

(j)

4 wherein $Y_1$ is a $C_1$ to $C_{10}$ straight chain or branched alkyl, preferably, a $C_2$ to $C_5$ straight chain or branched alkyl or a substituted $C_5$ to $C_7$ cycloalkyl; Hal is halogen, for example, F, Cl, Br or I, $R_9$ is hydrogen or a lower alkyl; $n_1$ is an integer from 1 to 6, preferably from 2 to 4; $n_2$ and $n_3$ are independently an integer from 1 to 5, preferably from 1 to 3; $n_4$ is an integer from 0 to 3; and $n_4$ is an integer from 1 to 6.

In another aspect of the present invention, it is provided a pharmaceutical composition containing the colchicine derivatives and pharmaceutically acceptable salts thereof as effective components, the pharmaceutical composition having anticancer, anti-proliferous and anti-inflammatory effects and immunosuppressive and muscle-relaxing functions.

In still another aspect of the present invention, it is provided methods for preparing the colchicine derivative represented by the formula (I) according to the reaction schemes 1, 2, 3, 4 and 5. In the reaction schemes 1 to 5, the colchicine derivatives of the formula (I) are represented as the formula (Ia), (Ib), (Ic), (Id), or (Ie):

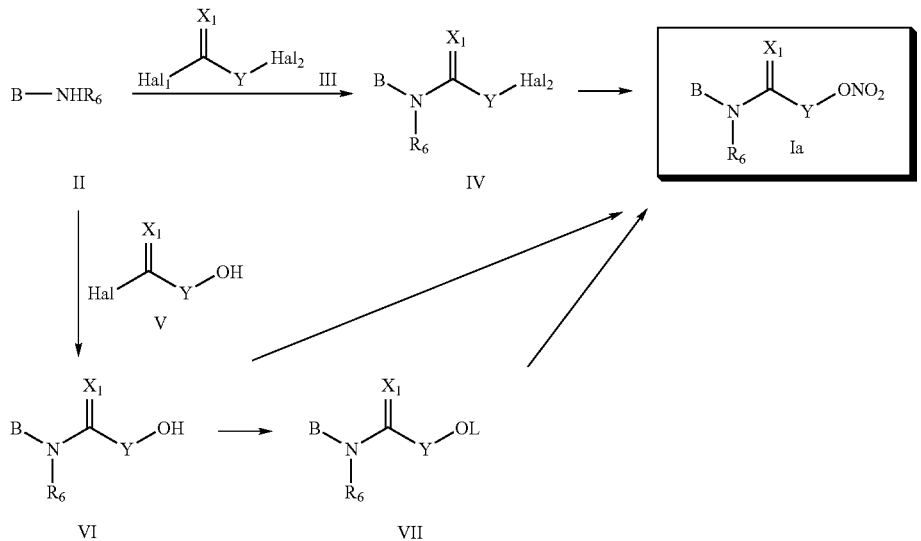

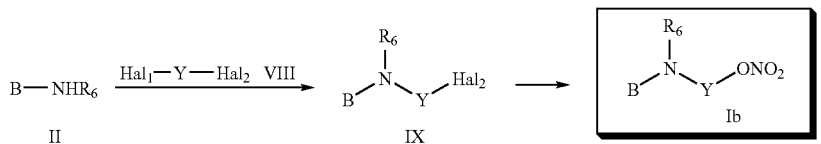

-continued
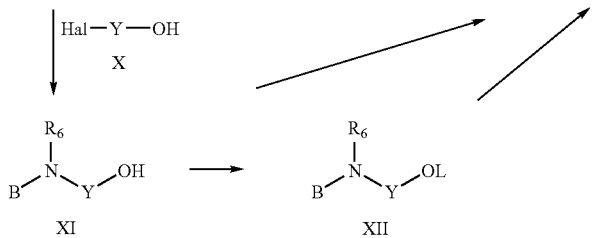
Reaction scheme 3 (Method 3)
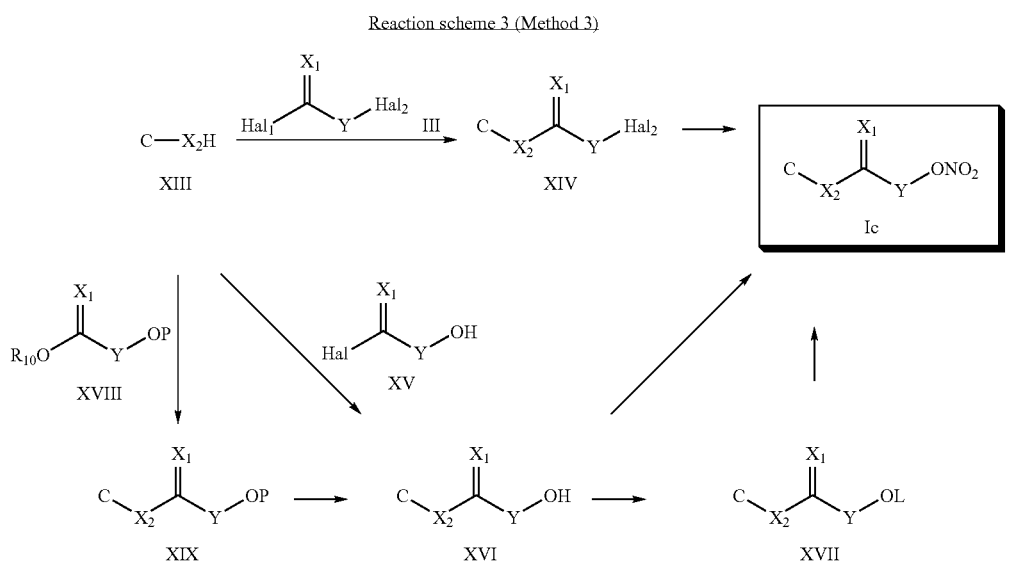
Reaction scheme 4 (Method 4)
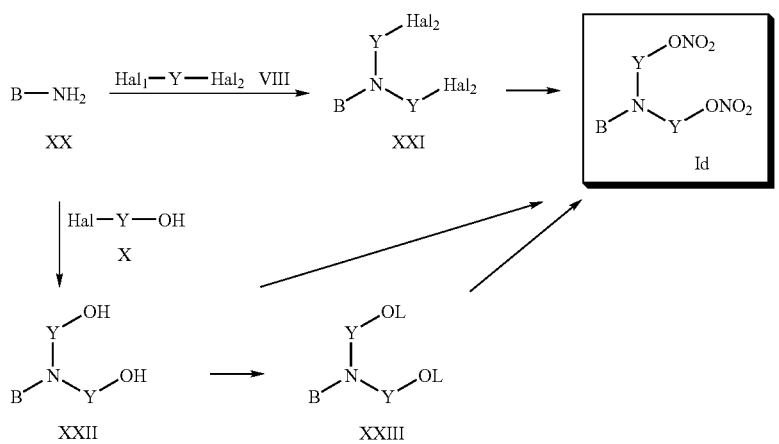
Reaction scheme 5 (Method 5)
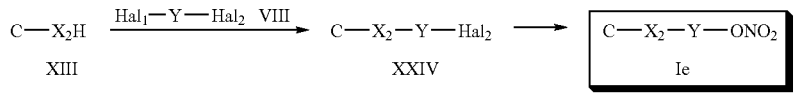

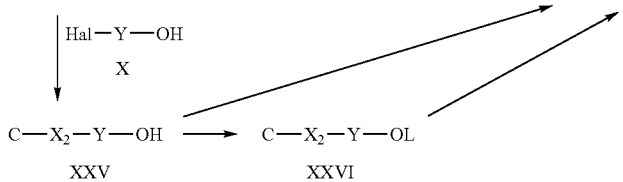

wherein B in the formulas (Ia), (Ib), (Ic), (Id) and (Ie) is represented by the formula C1 or C2, and C in the formulas is represented by the formula C1, C2, C3, C4 or C5:

C1
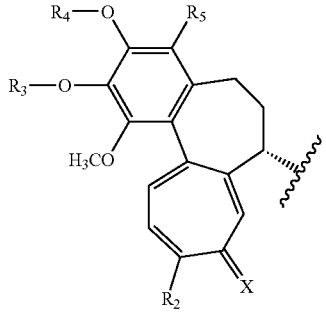

C2
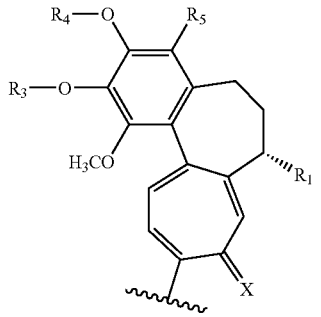

C3

C4

C5
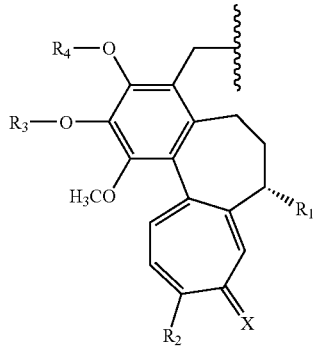

wherein $R_1$ through $R_5$ and X are defined as in the compound of the formula (I).

$R_6$ is hydrogen or a lower alkyl; $X_1$ and $X_2$ are independently O or S; Hal, $Hal_1$, and $Hal_2$ may be the same or different halogens; L is a leaving group selected from methanesulfonyl, p-toluenesulfonyl or triflate; P represents a general hydroxy-protecting group including methoxymethyl or t-butyldimethylsilyl; $R_{10}$ is hydrogen or a lower alcohol of $C_1$ to $C_3$; and Y is represented by the general formula (a'), (b'), (c'), (d') or (e'):

(a')

(b')
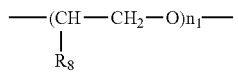

(c')
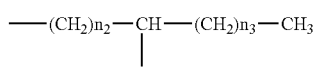

(d')
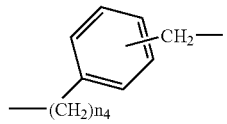

(e')
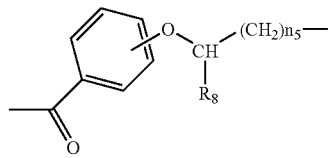

wherein $Y_1$ represents a $C_1$ to $C_{10}$ straight chain or branched alkyl, preferably, a $C_2$ to $C_5$ straight chain or branched alkyl, or a substituted $C_5$ to $C_7$ cycloalkyl, $R_8$ represents hydrogen or a lower alkyl, $n_1$ is an integer from 1 to 6, preferably an integer from 2 to 4, $n_2$ and $n_3$ are independently an integer from 1 to 5, preferably an integer from 1 to 3, $n_4$ is an integer 0 to 3, and $n_5$ is an integer from 1 to 6.

BEST MODE FOR CARRYING OUT THE INVENTION

Figure 1:
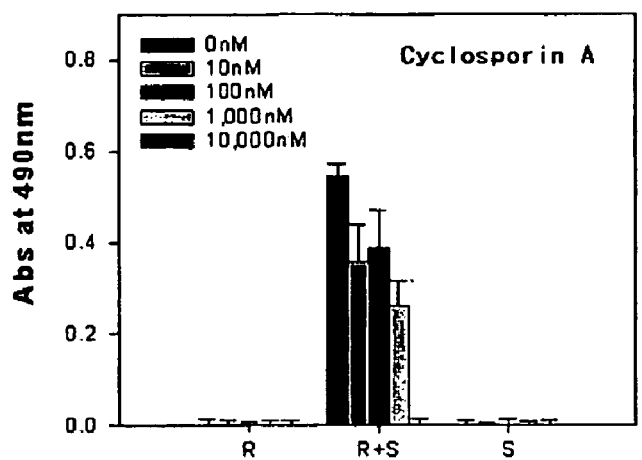
FIG. 1 is a graph showing the immonosuppressive effect of a colchicine derivative tested by mixed lymphocyte reaction (MLR)
Figure 1:
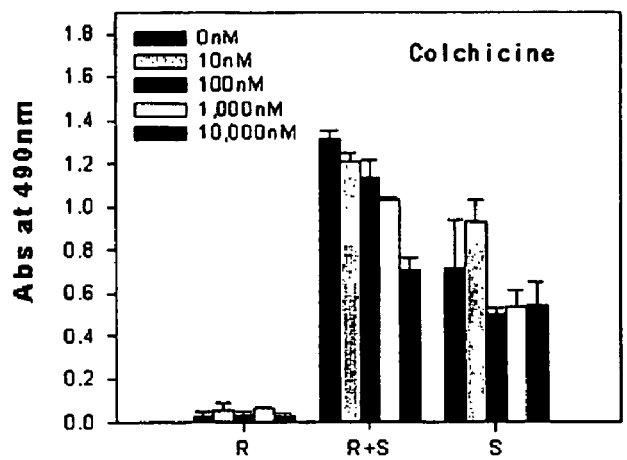
Figure 1:
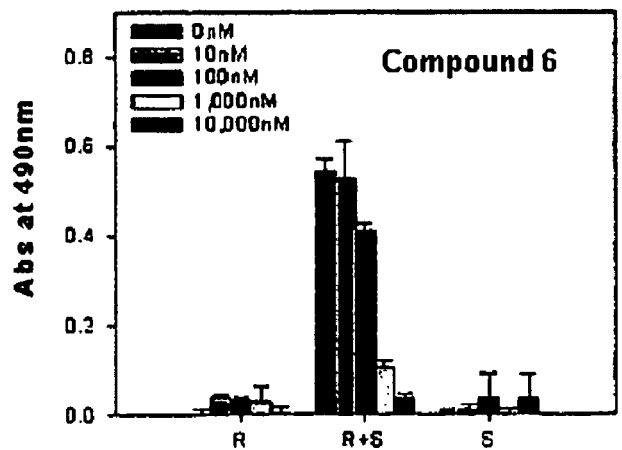
Figure 1:
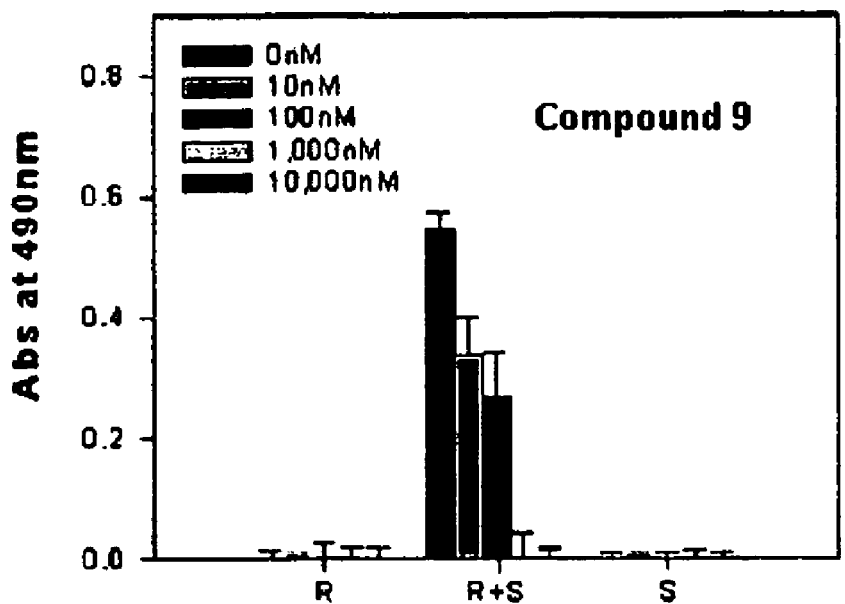
Figure 1:
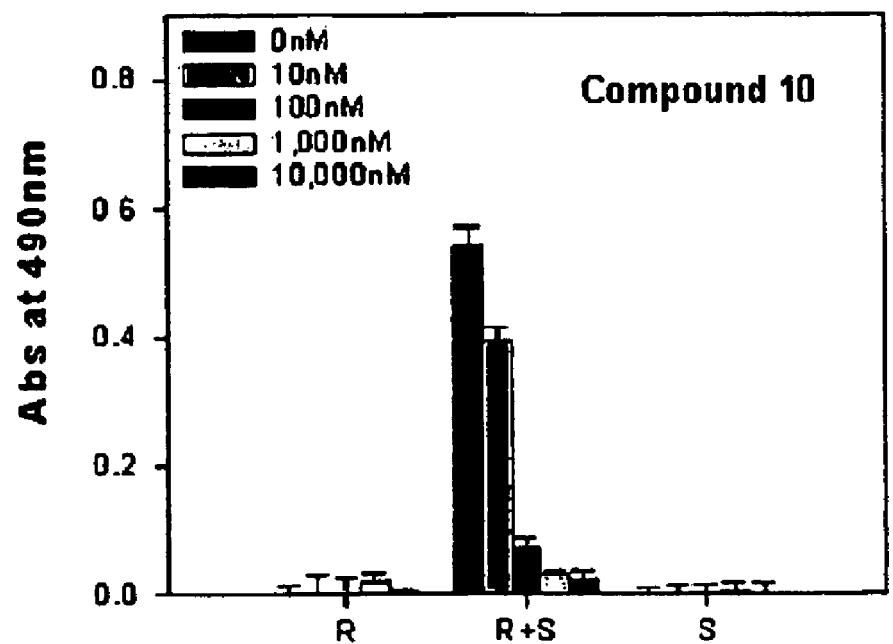
Figure 1:
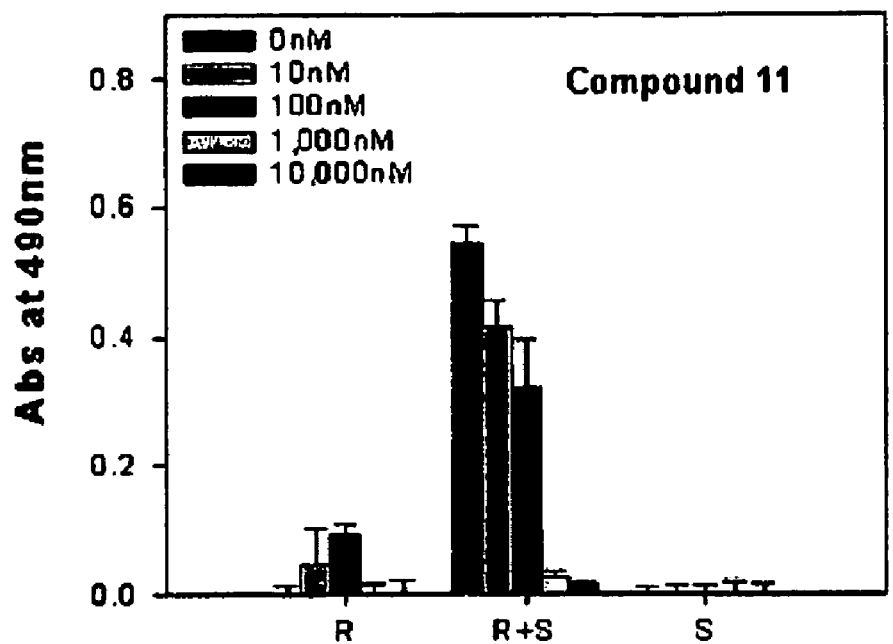
Figure 1:
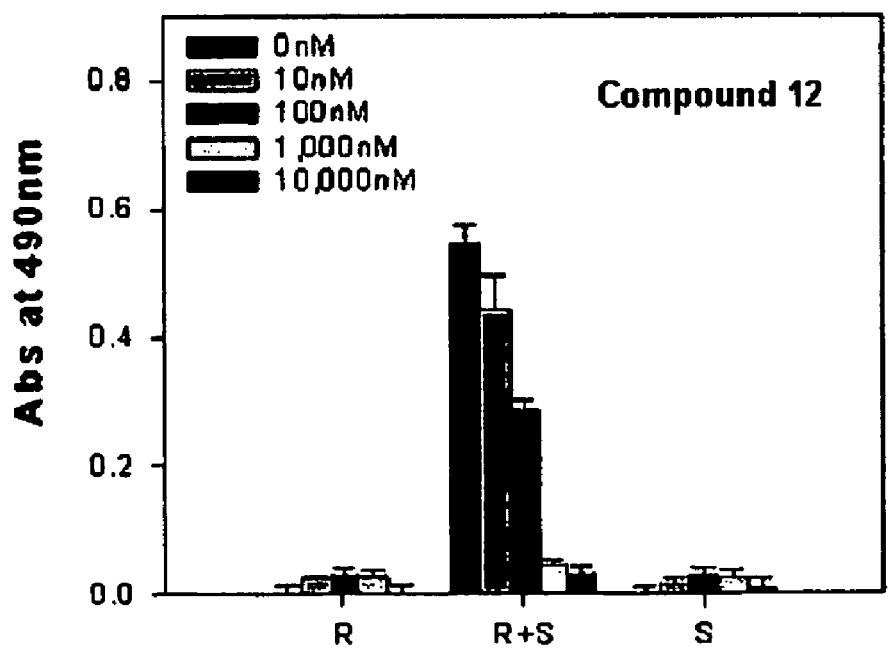

The present invention will now be described in more detail.

Throughout the specification, a lower alkyl represents a saturated $C_1$ to $C_6$, preferably, $C_1$ to $C_4$ straight chain or branched hydrocarbon.

Preferred examples of the colchicine derivative of the formula (I) and its pharmaceutically acceptable salt according to the present invention include:

4-chloro-N-(1,2,3,10-tetramethoxy-9-oxo-5,6,7,9-tetrahydro-benzo[a]heptarene-7-yl)-butylamide;
4-chloromethyl-N-(1,2,3,10-tetramethoxy-9-oxo-5,6,7,9-tetrahydro-benzo[a]heptarene-7-yl)-benzamide;
3 -chloromethyl-N-(1,2,3,10-tetramethoxy-9-oxo-5,6,7,9-tetrahydro-benzo[a]heptarene-7-yl)-benzamide;
4-iodo-N-(1,2,3,10-tetramethoxy-9-oxo-5,6,7,9-tetrahydro-benzo[a]heptarene-7-yl)-butylamide;
4-nitrooxy-N-(1,2,3,10-tetramethoxy-9-oxo-5,6,7,9-tetrahydro-benzo[a]heptarene-7-yl)-butylamide;
4-iodomethyl-N-(1,2,3,10-tetramethoxy-9-oxo-5,6,7,9-tetrahydro-benzo[a]heptarene-7-yl)-benzamide;
4-nitrooxymethyl-N-(1,2,3,10-tetramethoxy-9-oxo-5,6,7,9-tetrahydro-benzo[a]heptarene-7-yl)-benzamide;
3-iodomethyl-N-(1,2,3,10-tetramethoxy-9-oxo-5,6,7,9-tetrahydro-benzo[a]heptarene-7-yl)-benzamide;
3-nitrooxymethyl-N-(1,2,3,10-tetramethoxy-9-oxo-5,6,7,9-tetrahydro-benzo[a]heptarene-7-yl)-benzamide;
4-chloro-N-(1,2,3-trimethoxy-10-methylsulfanyl-9-oxo-5,6,7,9-tetrahydro-benzo[a]heptarene-7-yl)-butylamide;
4-chloromethyl-N-(1,2,3-trimethoxy-10-methylsulfanyl-9-oxo-5,6,7,9-tetrahydro-benzo[a]heptarene-7-yl)-benzamide;
3-chloromethyl-N-(1,2,3-trimethoxy-10-methylsulfanyl-9-oxo-5,6,7,9-tetrahydro-benzo[a]heptarene-7-yl)-benzamide;
4-iodo-N-(1,2,3-trimethoxy-10-methylsulfanyl-9-oxo-5,6,7,9-tetrahydro-benzo[a]heptarene-7-yl)-butylamide;
4-nitrooxy-N-(1,2,3-trimethoxy-10-methylsulfanyl-9-oxo-5,6,7,9-tetrahydro-benzo[a]heptarene-7-yl)-butylamide;
4-iodomethyl-N-(1,2,3-trimethoxy-10-methylsulfanyl-9-oxo-5,6,7,9-tetrahydro-benzo[a]heptarene-7-yl)-benzamide;
4-nitrooxymethyl-N-(1,2,3-trimethoxy-10-methylsulfanyl-9-oxo-5,6,7,9-tetrahydro-benzo[a]heptarene-7-yl)-benzamide;
3-iodomethyl-N-(1,2,3-trimethoxy-10-methylsulfanyl-9-oxo-5,6,7,9-tetrahydro-benzo[a]heptarene-7-yl)-benzamide;
3-nitrooxymethyl-N-(1,2,3-trimethoxy-10-methylsulfanyl-9-oxo-5,6,7,9-tetrahydro-benzo[a]heptarene-7-yl)-benzamide;
N-(7-acetylamino-1,2,3-trimethoxy-9-oxo-5,6,7,9-tetrahydro-benzo[a]heptarene-10-yl)-4-chloromethyl-benzamide;
N-(7-acetylamino-1,2,3-trimethoxy-9-oxo-5,6,7,9-tetrahydro-benzo[a]heptarene-10-yl)-4-iodomethyl-benzamide;
N-(7-acetylamino-1,2,3-trimethoxy-9-oxo-5,6,7,9-tetrahydro-benzo[a]heptarene-10-yl)-4-nitrooxymethyl-benzamide;
4-chloromethyl-benzoic acid 7-acetylamino-1,2,3,10-tetramethoxy-9-oxo-5,6,7,9-tetrahydro-benzo[a]heptarene-7-yl-methyl ester;
4-chloromethyl-benzoic acid 7-acetylamino-1,2,3-trimethoxy-10-methylsulfanyl-9-oxo-5,6,7,9-tetrahydro-benzo[a]heptarene-7-yl-methyl ester;
4-chloro-butyric acid 7-acetylamino-1,2,3,10-tetramethoxy-9-oxo-5,6,7,9-tetrahydro-benzo[a]heptarene-7-yl-methyl ester;
4-chloro-butyric acid 7-acetylamino-1,2,3-trimethoxy-10-methylsulfanyl-9-oxo-5,6,7,9-tetrahydro-benzo[a]heptarene-7-yl-methyl ester;
4-nitrooxymethyl-benzoic acid 7-acetylamino-1,2,3,10-tetramethoxy-9-oxo-5,6,7,9-tetrahydro-benzo[a]heptarene-4-yl-methyl ester;
4-iodomethyl-butyric acid 7-acetylamino-1,2,3-trimethoxy-10-methylsulfanyl-9-oxo-5,6,7,9-tetrahydro-benzo[a]heptarene-4-yl-methyl ester;
4-nitrooxymethyl-butyric acid 7-acetylamino-1,2,3-trimethoxy-10-methylsulfanyl-9-oxo-5,6,7,9-tetrahydro-benzo[a]heptarene-4-yl-methyl ester;
4-iodomethyl-benzoic acid 7-acetylamino-1,2,3 -trimethoxy-10-methylsulfanyl-9-oxo-5,6,7,9-tetrahydro-benzo[a]heptarene-4-yl-methyl ester;
4-nitrooxymethyl-benzoic acid 7-acetylamino-1,2,3-trimethoxy-10-methylsulfanyl-9-oxo-5,6,7,9-tetrahydro-benzo[a]heptarene-4-yl-methyl ester;
(−)-3-chloromethyl-benzoic acid 1,2,3,10-tetramethoxy-9-oxo-5,6,7,9-tetrahydro-benzo[a]heptarene-7-yl ester;
(+)-3-chloromethyl-benzoic acid 1,2,3,10-tetramethoxy-9-oxo-5,6,7,9-tetrahydro-benzo[a]heptarene-7-yl ester;
(−)-3-iodomethyl-benzoic acid 1,2,3,10-tetramethoxy-9-oxo-5,6,7,9-tetrahydro-benzo[a]heptarene-7-yl ester;
(+)-3-iodomethyl-benzoic acid 1,2,3,10-tetramethoxy-9-oxo-5,6,7,9-tetrahydro-benzo[a]heptarene-7-yl ester;
(−)-3-nitrooxymethyl-benzoic acid 1,2,3,10-tetramethoxy-9-oxo-5,6,7,9-tetrahydro-benzo[a]heptarene-7-yl ester;
(+)-3-nitrooxymethyl-benzoic acid 1,2,3,10-tetramethoxy-9-oxo-5,6,7,9-tetrahydro-benzo[a]heptarene-7-yl ester;
4-chloro-butyric acid 7-acetylamino-1,2,10-trimethoxy-9-oxo-5,6,7,9-tetrahydro-benzo[a]heptarene-3-yl ester;
4-chloromethyl-benzoic acid 7-acetylamino-1,2,10-trimethoxy-9-oxo-5,6,7,9-tetrahydro-benzo[a]heptarene-3-yl ester;
3-chloromethyl-benzoic acid 7-acetylamino-1,2,10-trimethoxy-9-oxo-5,6,7,9-tetrahydro-benzo[a]heptarene-3-yl ester;
4-nitrooxy-butyric acid 7-acetylamino-1,2,10-trimethoxy-9-oxo-5,6,7,9-tetrahydro-benzo[a]heptarene-3-yl ester;

4-nitrooxymethyl-benzoic acid 7-acetylamino-1,2,10-trimethoxy-9-oxo-5,6,7,9-tetrahydro-benzo[a]heptarene-3-yl ester;
3-nitrooxymethyl-benzoic acid 7-acetylamino-1,2,10-trimethoxy-9-oxo-5,6,7,9-tetrahydro-benzo[a]heptarene-3-yl ester;
4-chloro-N-methyl-N-(1,2,3-trimethoxy-10-methylsulfanyl-9-oxo-5,6,7,9-tetrahydro-benzo[a]heptarene-7-yl)-butylamide;
4-nitrooxymethyl-N-methyl-N-(1,2,3-trimethoxy-10-methylsulfanyl-9-oxo-5,6,7,9-tetrahydro-benzo[a]heptarene-7-yl)-benzamide;
3-nitrooxymethyl-N-methyl-N-(1,2,3-trimethoxy-10-methylsulfanyl-9-oxo-5,6,7,9-tetrahydro-benzo[a]heptarene-7-yl)-benzamide;
(−)-3-chloromethyl-benzoic acid 1,2,3-trimethoxy-10-methylsulfenyl-9-oxo-5,6,7,9-tetrahydro-benzo[a]heptarene-7-yl ester;
(+)-3-chloromethyl-benzoic acid 1,2,3-trimethoxy-10-methylsulfenyl-9-oxo-5,6,7,9-tetrahydro-benzo[a]heptarene-7-yl ester;
(−)-3-nitrooxymethyl-benzoic acid 1,2,3-trimethoxy-10-methylsulfenyl-9-oxo-5,6,7,9-tetrahydro-benzo[a]heptarene-7-yl ester;
(+)-3-nitrooxymethyl-benzoic acid 1,2,3-trimethoxy-10-methylsulfenyl-9-oxo-5,6,7,9-tetrahydro-benzo[a]heptarene-7-yl ester;
4-chloro-N-methyl-N-(1,2,3,10-tetramethoxy-9-oxo-5,6,7,9-tetrahydro-benzo[a]heptarene-7-yl) butylamide;
4-chloromethyl-N-methyl-N-(1,2,3,10-tetramethoxy-9-oxo-5,6,7,9-tetrahydro-benzo[a]heptarene-7-yl) benzamide;
N-methyl-4-nitrooxy-N-(1,2,3,10-tetramethoxy-9-oxo-5,6,7,9-tetrahydro-benzo[a]heptarene-7-yl) butylamide;
N-methyl-4-nitrooxymethyl-N-(1,2,3,10-tetramethoxy-9-oxo-5,6,7,9-tetrahydro-benzo[a]heptarene-7-yl) benzamide;
4-nitrooxy-butyric acid 7-acetylamino-1,2,3,10-tetramethoxy-9-oxo-5,6,7,9-tetrahydro-benzo[a]heptarene-4-yl methyl ester;
4-chloro-N-(1,2,3-trimethoxy-4-methoxymethyl-10-methylsulfanyl-9-oxo-5,6,7,9-tetrahydro-benzo[a]heptarene-7-yl)-butylamide;
4-chloromethyl-N-(1,2,3-trimethoxy-4-methoxymethyl-10-methylsulfanyl-9-oxo-5,6,7,9-tetrahydro-benzo[a]heptarene-7-yl)-benzamide;
4-nitrooxy-N-(1,2,3-trimethoxy-4-methoxymethyl-10-methylsulfanyl-9-oxo-5,6,7,9-tetrahydro-benzo[a]heptarene-7-yl)-butylamide;
4-nitrooxymethyl-N-(1,2,3-trimethoxy-4-methoxymethyl-10-methylsulfanyl-9-oxo-5,6,7,9-tetrahydro-benzo[a]heptarene-7-yl)-benzamide;
N-(7-acetylamino-1,2,3-trimethoxy-9-oxo-5,6,7,9-tetrahydro-benzo[a]heptarene-10-yl)-3-chloromethyl-benzamide;
N-(7-acetylamino-1,2,3-trimethoxy-9-oxo-5,6,7,9-tetrahydro-benzo[a]heptarene-10-yl)-3-nitrooxymethyl-benzamide;
N-(7-acetylamino-1,2,3-trimethoxy-9-oxo-5,6,7,9-tetrahydro-benzo[a]heptarene-10-yl-4-chloro-butylamide;
4-chloromethyl-N-(10-dimethylamino-1,2,3-trimethoxy-9-oxo-5,6,7,9-tetrahydro-benzo[a]heptarene-7-yl)-benzamide;
N-(10-dimethylamino-1,2,3-trimethoxy-9-oxo-5,6,7,9-tetrahydro-benzo[a]heptarene-7-yl)-4-nitrooxymethyl-benzamide;
3-chloromethyl-N-(10-dimethylamino-1,2,3-trimethoxy-9-oxo-5,6,7,9-tetrahydro-benzo[a]heptarene-7-yl)-benzamide;
N-(10-dimethylamino-1,2,3-trimethoxy-9-oxo-5,6,7,9-tetrahydro-benzo[a]heptarene-7-yl)-3-nitrooxymethyl-benzamide;
4-chloro-N-(10-dimethylamino-1,2,3-trimethoxy-9-oxo-5,6,7,9-tetrahydro-benzo[a]heptarene-7-yl)-butyrilamide; and
N-(10-dimethylamino-1,2,3-trimethoxy-9-oxo-5,6,7,9-tetrahydro-benzo[a]heptarene-7-yl)-4-nitrooxy-butyrilamide.

Examples of the pharmaceutically acceptable salt of the colchicine derivative of the formula (I) include, but are not limited to, salts with inorganic bases such as sodium, potassium, magnesium or calcium and salts with organic bases such as ammonium, lysine, ethanolamine, N,N'-dibenzylethylenediamine and angelic acid Preparation methods of the invention will now be described in more detail.

Method 1

In Method 1 for preparing a compound of the formula (Ia), first, a compound of the formula (II) is reacted with a compound of the formula (III) to produce a compound (IV). The reaction can be carried out without using a base, but is generally carried out in the presence of a base used for amidation. Preferred examples of the base include pyridine, triethylamine, diethylisopropylamine and dimethylphenylamine, and a phase transfer catalyst such as sodium hydrocarbonate or benzyltriethylammonium chloride. The reaction can be carried out without using a solvent, but is advantageously carried out in the presence of a solvent that does not adversely affect the reaction. Examples of the solvent used include dichloromethane, chloroform, tetrahydrofuran, diethylether, toluene and dimethylformamide. The reaction temperature is not specifically limited and is generally carried out at reduced or elevated temperature, preferably at room temperature.

Second, the compound of the formula (IV) is subjected to nitration to convert it into a compound of the formula (Ia). Compounds capable of nitrating halogen are generally used for the reaction, and examples of such compounds include $AgNO_3$ and t-butylammonium nitrate ($Bu_4NNO_3$). The reaction is preferably carried out in the presence of a solvent that does not adversely affect the reaction, and examples of such solvent include chloroform, acetonitrile, a mixed solution of acetonitrile and water, dichloromethane, and the like. The reaction temperature is not specifically limited and is generally carried out at reduced or elevated temperature, preferably at room temperature.

Alternatively, the compound of the formula (Ia) can be synthesized by reacting the compound of the formula (II) with a compound of the formula (V) to produce a compound (VI), followed by converting it into the compound (Ia). The conditions for reacting the compound of the formula (II) with the compound of the formula (V) are the same as those for amidation like in the reaction between the compound of the formula (II) and the compound of the formula (III). In order to convert the compound (VI) into the compound of the formula (Ia), the reaction is generally carried out under nitrating conditions of alcohol. Preferably, nitric acid and sulfuric acid, dinitrogen pentaoxide ($N_2O_5$) and aluminum chloride III, potassium nitrate and boron trifluoride ($BF_3$), acetylnitrate, etc., may be used, most preferably nitric acid and acetic anhydride ($Ac_2O$) are used. The reaction is preferably carried out in the presence of a solvent that does not adversely affect the reaction, and examples of the solvent used include chloroform, dichloromethane, and the like. The reaction temperature is not specifically limited and is generally carried out at reduced or elevated temperature, preferably at room temperature.

The compound of the formula (Ia) can also be synthesized by performing nitration a compound of the formula (VII) prepared by converting hydrogen of alcohol in the compound of the formula (VI) into a leaving group such as methane sulfonyl, p-toluene sulfonyl or triflate. In order to convert the compound (VII) into the compound of the formula (Ia), the reaction is generally carried out under nitrating conditions. Most preferably, t-butylammonium nitrate ($Bu_4NNO_3$), t-butylammonium nitrate ($Bu_4NNO_3$) and nitric acid, nitric acid and silver nitrate, or potassium nitrate is used. The reaction is preferably carried out in the presence of a solvent that does not adversely affect the reaction. Examples of the solvent used include chloroform, dichloromethane, a mixed solution of benzene and water, acetonitrile, ethylalcohol, and the like. The reaction temperature is not specifically limited and is generally carried out at reduced or elevated temperature, preferably at room temperature.

Desired products can be isolated and purified by general methods, for example, column chromatography or recrystallization.

Method 2

In Method 2 for preparing a compound of the formula (Ib), first, a compound of the formula (II) is reacted with a compound of the formula (VIII) to produce a compound (IX). The reaction is generally carried out in the same manner as in the amidation for converting the compound (II) into the compound (IV) as described in Method 1.

Second, the compound of the formula (IX) is subjected to nitration to produce the compound of the formula (Ib). This reaction is generally carried out in the same manner as in the nitration for converting the compound of the formula (IV) into the compound of the formula (Ia) as described in Method 1.

Alternatively, the compound of the formula (Ib) can be synthesized by reacting the compound of the formula (II) with a compound of the formula (X) to produce a compound (XI), followed by converting the same into the compound (Ib). The conditions of reacting the compound of the formula (II) with the compound of the formula (X) are the same as those for amidation like in the reaction between the compound of the formula (II) and the compound of the formula (IV) as described in Method 1. In order to convert the compound (XI) into the compound of the formula (Ib), the reaction is generally carried out under nitrating conditions of an alcoholic compound, that is, under the same conditions as those of converting the compound of the formula (VI) into the compound of the formula (Ia) as described in Method 1.

The compound of the formula (Ib) can also be synthesized by performing nitration the compound of the formula (XII) prepared by converting hydrogen of alcohol in the compound of the formula (XI) into a leaving group such as methane sulfonyl, p-toluene sulfonyl or triflate. In order to convert the compound (XII) into the compound of the formula (Ib), the reaction is generally carried out under nitrating conditions, that is, under the same conditions of converting the compound of the formula (VII) into the compound of the formula (Ia) as described in Method 1.

Desired products can be isolated and purified by general methods, for example, column chromatography or recrystallization.

Method 3

In Method 3 for preparing a compound of the formula (Ic), first, a compound of the formula (III) is reacted with a compound of the formula (XI) to produce a compound (XIV). The reaction is generally esterification between alcohol ($X_2$=O) or thioalcohol ($X_2$=S) and acyl or thioacyl halide, that is, the reaction is carried out in the presence of nickelacetylacetonate or zinc chloride or in the presence of a base that can be used for esterification. Examples of the base include pyridine, 4-dimethylaminopyridine, triethylamine, diethylisopropylamine, dimethylphenylamine, 2,6-lutidine, or sodium hydride (NaH), cesium carbonate, and a phase transfer catalyst such as sodium hydroxide or benzyltriethylammonium chloride. Also, the reaction can be advantageously carried out in the presence of a solvent that does not adversely affect the reaction. Examples of the solvent include dichloromethane, chloroform, tetrahydrofuran, diethylether, toluene, dimethylformamide, toluene, dimethylformamide, acetonitrile, and the like. The reaction temperature is not specifically limited and is generally carried out at reduced or elevated temperature, preferably at room temperature.

Second, the compound of the formula (XIV) synthesized in the first step is subjected to nitration to produce the compound of the formula (Ic). This reaction is generally carried out in the same manner as in the nitration of halogen for converting the compound of the formula (IV) into the compound of the formula (Ia) as described in Method 1.

Alternatively, the compound of the formula (Ic) can be synthesized by reacting the compound of the formula (XIII) with a compound of the formula (XV) to produce a compound (XVI), followed by converting the same into the compound (Ic). The reaction between the compound of the formula (XIII) and the compound of the formula (XV) is generally esterification between alcohol ($X_2$=O) or thioalcohol ($X_2$=S) and acyl or thioacyl halide, that is, the reaction is carried out under the same conditions as the reaction between the compound of the formula (XIII) and the compound of the formula (III) as mentioned above. In order to convert the compound (XVI) into the compound of the formula (Ic), the reaction is generally carried out under nitrating conditions of an alcoholic compound, that is, under the same conditions as those of converting the compound of the formula (VI) into the compound of the formula (Ia) as described in Method 1.

The compound of the formula (Ic) also can be synthesized by performing nitration the compound of the formula (XVII) prepared by converting hydrogen of alcohol in the compound (XVI) is converted into a leaving group such as methane sulfonyl, p-toluene sulfonyl or triflate. In order to convert the compound (XVI) into the compound of the formula (Ic), the reaction is generally carried out under nitrating conditions of an alcoholic compound, that is, under the same conditions of converting the compound of the formula (VII) into the compound of the formula (Ia) as described in Method 1.

Also, the compound of the formula (Ic) can be synthesized by reacting the compound of the formula (XIII) with a compound of the formula (XVIII) having a protecting group in alcohol to convert the same into a compound of the formula (XIX), followed by converting the compound of the formula (XIX) into the compound (XVI) by a deprotection. The conversion of the compound of the formula (XIII) into the compound of the formula (XIX) is generally esterification between alcohol ($X_2$=O) or thioalcohol ($X_2$=S) and carboxylic acid ($R_{10}$=H) or carboxylic acid ester ($R_{10}$=a lower alkyl of $C_1$ to $C_3$). When $R_{10}$ is H, the reaction is preferably carried out in the presence of a base, preferably pentafluorophenyl and pyridine, or ethylchloroformate and triethylamine. This reaction can also be carried out without using a solvent, preferably in the presence of a solvent that does not adversely affect the reaction. Examples of the solvent include dichloromethane, chloroform, tetrahydrofuran, diethylether, and the like. The reaction temperature is not specifically limited and is generally carried out at reduced or elevated temperature, preferably at room temperature.

Desired products can be isolated and purified by general methods, for example, column chromatography or recrystallization.

Method 4

In Method 4 for preparing a compound of the formula (Id), first, a compound of the formula (XX) is reacted with a compound of the formula (VIII) to produce a compound (XXI). The reaction is generally carried out in the same manner as in the amidation for converting the compound (II) into the compound (IV) as described in Method 1.

Second, the compound of the formula (XXI) synthesized in the first step is subjected to nitration to produce the compound of the formula (Id). This reaction is generally carried out in the same manner as in the nitration of halogen for converting the compound of the formula (IV) into the compound of the formula (Ia) as described in Method 1.

Alternatively, the compound of the formula (Id) can be synthesized by reacting the compound of the formula (XX) with a compound of the formula (X) to produce a compound (XXII), followed by converting the same into the compound (Id). The conditions of reacting the compound of the formula (XX) with the compound of the formula (X) are the same as those for amidation by which the compound of the formula (II) is converted into the compound of the formula (IV) as described in Method 1. In order to convert the compound (XXII) into the compound of the formula (Id), the reaction is generally carried out under nitrating conditions of an alcoholic compound, that is, under the same conditions as those of converting the compound of the formula (VI) into the compound of the formula (Ia) as described in Method 1.

The compound of the formula (Id) can also be synthesized by performing nitration the compound of the formula (XXIII) prepared by converting hydrogen of alcohol in the compound of the formula (XXII) into a leaving group such as methane sulfonyl, p-toluene sulfonyl or triflate. In order to convert the compound (XXIII) into the compound of the formula (Id), the reaction is generally carried out under nitrating conditions, that is, under the same conditions of converting the compound of the formula (VII) into the compound of the formula (Ia) as described in Method 1.

Desired products can be isolated and purified by general methods, for example, column chromatography or recrystallization.

Method 5

In Method 5 for preparing a compound of the formula (Ie), first, a compound of the formula (XIII) is reacted with a compound of the formula (VIII) to produce a compound (XXIV). The reaction is generally a reaction between alcohol ($X_2$=O) or thioalcohol ($X_2$=S) and alkylhalide to produce ether or thioether, preferably in the presence of a base that can be used for etherification. Examples of the base include sodium hydride (NaH), cecium carbonate, silver carbonate, a phase transfer catalyst such as sodium or potassium hydroxide or benzyltriethylammonium chloride, or crown ether. The reaction is preferably carried out in the presence of a solvent that does not adversely affect the reaction. Examples of the solvent include dichloromethane, chloroform, tetrahydrofuran, diethylether, toluene, dimethylformamide, dimethyl sulfoxide, or benzene. The reaction temperature is not specifically limited and is generally carried out at reduced or elevated temperature, preferably at cooling temperature or room temperature.

Second, the compound of the formula (XXIV) synthesized in the first step is subjected to nitration to convert the same into a compound of the formula (Ie). The reaction is generally carried out in the same manner as in the nitration of halogen for converting the compound (IV) into the compound (Ia) as described in Method 1.

Alternatively, the compound of the formula (Ie) can be synthesized by reacting the compound of the formula (XIII) with a compound of the formula (X) to produce a compound (XXV), followed by converting the same into the compound (Ie). The conditions of reacting the compound of the formula (XIII) with the compound of the formula (X) are the same as those for the reaction between the compound of the formula (XIII) and the compound of the formula (VIII). In order to convert the compound (XXV) into the compound of the formula (Ie), the reaction is generally carried out under nitrating conditions of an alcoholic compound, preferably under the same conditions for the reaction for converting the compound of the formula (VI) into the compound of the formula (Ia) as described in Method 1.

The compound of the formula (Ie) can also be synthesized by performing nitration a compound of the formula (XXVI) prepared by converting hydrogen in alcohol in the compound of the formula (XXV) into a leaving group such as methane sulfonyl, p-toluene sulfonyl or triflate. In order to convert the compound (XXVI) into the compound of the formula (Ie), the reaction is generally carried out under nitrating conditions, preferably under the same conditions of converting the compound of the formula (VII) into the compound of the formula (Ia) as described in Method 1.

Desired products can be isolated and purified by general methods, for example, column chromatography or recrystallization.

As described above, the pharmaceutical composition according to the present invention including the colchicine derivative of the formula (I) and its pharmaceutically acceptable salt as effective components can be used for gout treatment agents, anticancer agents, anti-proliferous agents, anti-inflammatory agents, immunosuppressive agents and muscle relaxing agents.

The pharmaceutical composition according to the present invention can be prepared in various parenterally or orally administrable formulations. Typical examples of formations for parenteral administration preferably include in the form of an isotonic aqueous saline solution or suspension for injection. Examples of formulations for oral administration include tablets, capsules and the like, which may further contain a diluent (e.g.: lactose, dextrose, sucrose, mannitol, sorbitol, cellulose and/or glycine) or a lubricant (e.g.: silica, talc, stearic acid and its magnesium or potassium salt, and/or polyethylene glycol) in addition to effective components. Tablets can further be prepared with a binder such as magnesium aluminum silicate, starch paste, gelatins, tragacanth, methylcellulose, sodium carboxymethylcellulose and/or polyvinylpyrrolidine. In some cases, there may be further contained an disintegrator such as starch, agar, and alginate or sodium salts thereof, boiling mixtures and/or absorbents, a coloring agent, a flavoring agent, or a sweetener. The formulations can be prepared by general techniques of mixing, granulation or coating.

The pharmaceutical composition according to the present invention is sterilized and/or contains additives such as an antiseptic, a stabilizer, a hydrator or emulsifier, osmosis adjusting salts and/or a buffering agent, and other therapeutically effective materials. These preparations can be formulated in accordance with known methods usually employed in the formulation process.

As the effective components of the pharmaceutical composition of the present invention, the colchicine derivative of the formula (I) and its pharmaceutically acceptable salt can be administered to mammals including humans through parenteral or oral routes in an amount of 1 to 200 mg/kg (body weight) once or several times per a day.

EXAMPLES

The present invention will be further described by the following Examples, but the Examples do not limit the scope of the invention.

7-deacetylcolchicine used in Examples was synthesized according to the method of the reference EP 0 493 064 and Synthetic Communications 1997, 27(2), 293–296.

The preparation of the thiodeacetylcolchicine was carried out in accordance with the method of WO 9421598 and Bioorganic & Medicinal Chemistry, Vol 5, No. 12, pp 2277–2282(1997).

The preparation of N-(10-amino-1,2,3-trimethoxy-9-oxo-5,6,7,9-tetrahydro-benzo[a]heptarene-7-yl)acetamide was carried out in accordance with the method of WO 9421598.

The preparation of 4-hydroxymethylcolchicine and 4-hydroxy-methylthiocolchicine was carried out in accordance with the method of the Brevet Canadien 778369 and Justus Liebigs Ann. Chem. 662, 105–113 (1963)

The preparation of 7-hydroxy-1,2,3-trimethoxy-10-methylsulphenyl-6,7,-dihydro-5H-benzo[a]heptarene-9-on and colchicone was carried out in accordance with the method of the J. Med. Chem. Vol.40, 961–965 (1997).

Example 1

Preparation of 4-chloro-N-(1,2,3,10-tetramethoxy-9-oxo-5,6,7,9-tetrahydro-benzo[a]heptarene-7-yl)-butylamide 0.1 g (0.28 mmol) of deacetylcolchicine was placed into a 10 ml flask and 3.5 ml of tetrahydrofuran was added thereto and then dissolved. To the mixture, 0.2 ml (1.40 mmol) of triethylamine was added dropwise and 0.035 ml (0.31 mmol) of 4-chlorobutyryl chloride was added slowly. The mixture was stirred for 2 hours, and then extracted with chloroform and dried over anhydrous magnesium sulfate and filtered. The solvent in the mixture was removed under reduced pressure. The concentrated product was purified by the column chromatography (ethylacetate:methanol=85:15) to obtain the title product:

$^1$H NMR (500 MHz, CDCl$_3$) δ: 1.87–1.91 (m, 1H), 2.00–2.04 (m, 2H), 2.29–2.54 (m, 5H), 3.50 (t, J=4.3 Hz, 2H), 3.67 (s, 3H), 3.91 (s, 3H), 3.95 (s, 3H), 4.01 (s, 3H), 4.65–4.68 (m, 1H), 6.54 (s, 1H), 6.88 (d, J=11.0 Hz, 1H), 7.35 (d, J=11.0 Hz, 1H), 7.51 (d, J=6.5 Hz, 1H), 7.52 (s, 1H)

Example 2

Preparation of 4-chloromethyl-N-(1,2,3,10-tetramethoxy-9-oxo-5,6,7,9-tetrahydro-benzo[a]heptarene-7-yl)-benzamide

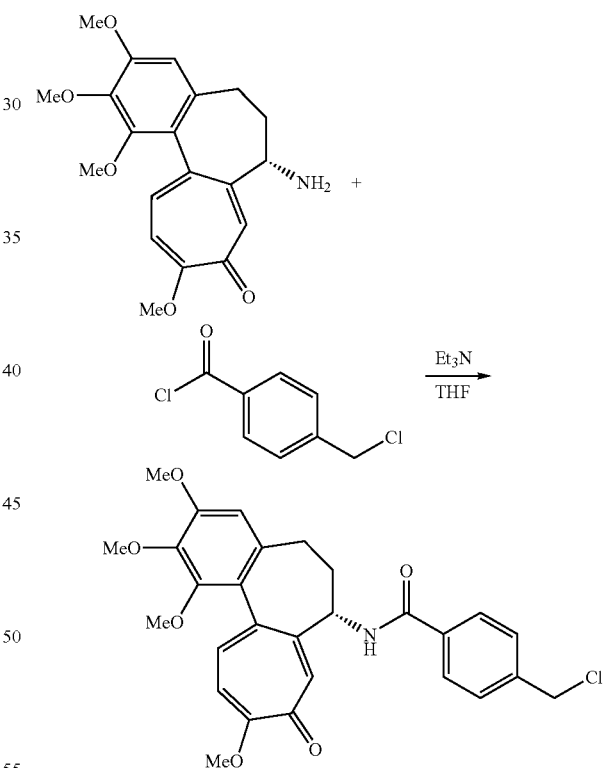

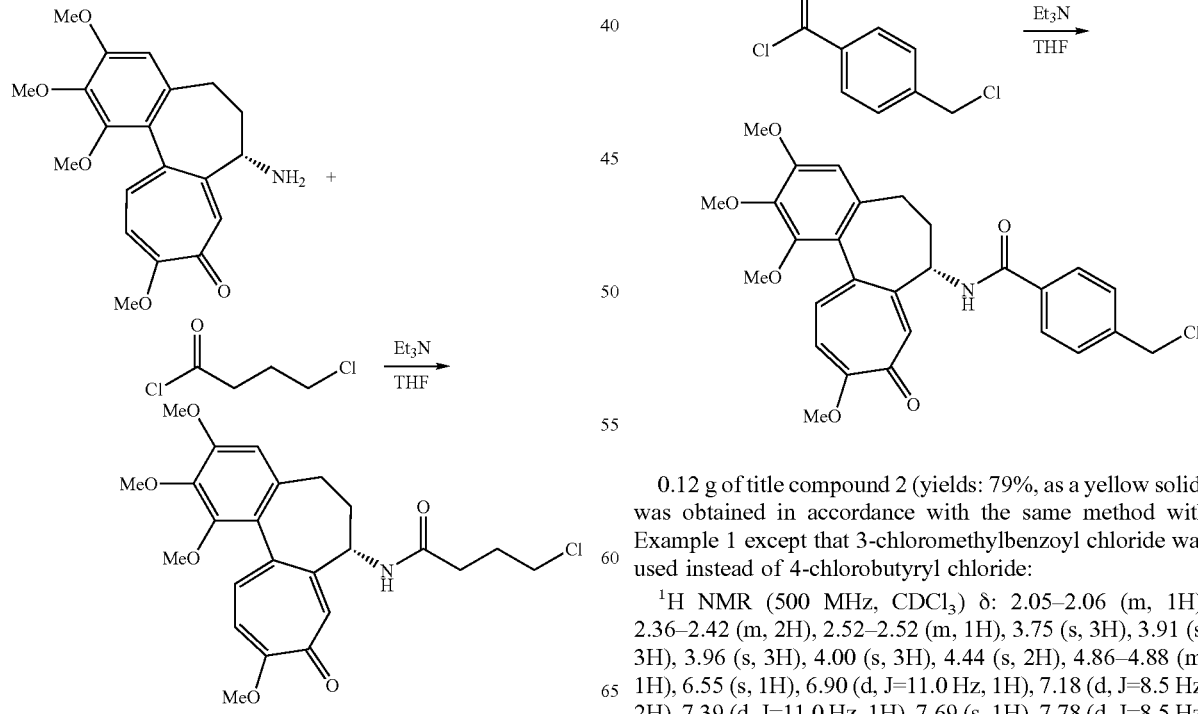

0.12 g of title compound 2 (yields: 79%, as a yellow solid) was obtained in accordance with the same method with Example 1 except that 3-chloromethylbenzoyl chloride was used instead of 4-chlorobutyryl chloride:

$^1$H NMR (500 MHz, CDCl$_3$) δ: 2.05–2.06 (m, 1H), 2.36–2.42 (m, 2H), 2.52–2.52 (m, 1H), 3.75 (s, 3H), 3.91 (s, 3H), 3.96 (s, 3H), 4.00 (s, 3H), 4.44 (s, 2H), 4.86–4.88 (m, 1H), 6.55 (s, 1H), 6.90 (d, J=11.0 Hz, 1H), 7.18 (d, J=8.5 Hz, 2H), 7.39 (d, J=11.0 Hz, 1H), 7.69 (s, 1H), 7.78 (d, J=8.5 Hz, 2H), 8.40 (d, J=6.5 Hz, 1H)

Example 3

Preparation of 3-chloromethyl-N-(1,2,3,10-tetramethoxy-9-oxo-5,6,7,9-tetrahydro-benzo[a]heptarene-7-yl)-benzamide

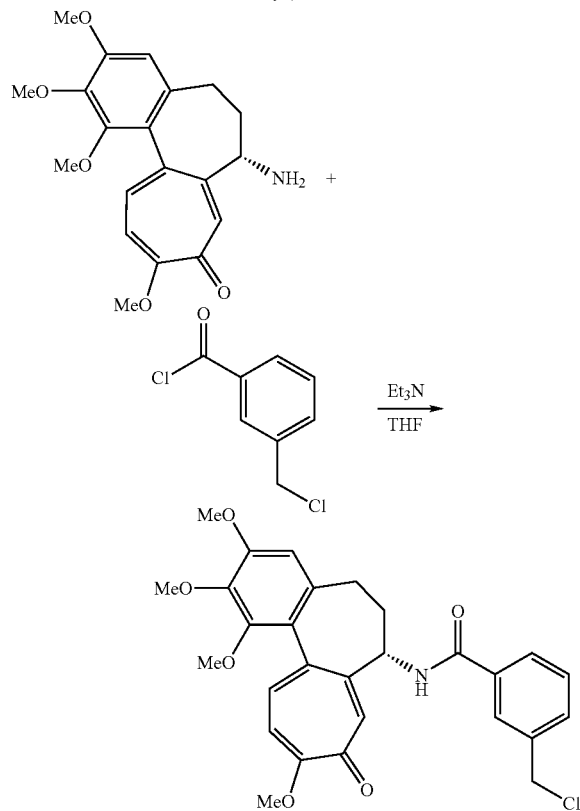

0.13 g of the title compound 3 (yields: 92%, as a yellow solid) was carried out in accordance with the same method with Example 1 except that 4-chloromethyl benzoyl chloride was used instead of 4-chlorobutyryl chloride:

$^1$H NMR (500 MHz, CDCl$_3$) δ: 2.22–2.26 (m, 1H), 2.39–2.48 (m, 2H), 2.53–2.57 (m, 1H), 3.75 (s, 3H), 3.95 (s, 3H), 3.97 (s, 3H), 4.01 (s, 3H), 4.90–4.95 (m, 1H), 5.30 (d, 12.0 Hz, 1H), 5.36 (d, 12.0 Hz, 1H), 6.56 (s, 1H), 6.93 (d, J=11.0 Hz, 1H), 7.12 (t, J=7.5 Hz, 1H), 7.30 (d, J=7.5 Hz, 1H), 7.41 (d, J=11.0 Hz, 1H), 7.56 (d, J=7.5 Hz, 1H), 7.69 (s, 1H), 7.77 (s, 1H), (d, J=6.5 Hz, 1H)

Example 4

Preparation of 4-nitrooxy-N-(1,2,3,10-tetramethoxy-9-oxo-5,6,7,9-tetrahydro-benzo[a]heptarene-7-yl)-butylamide

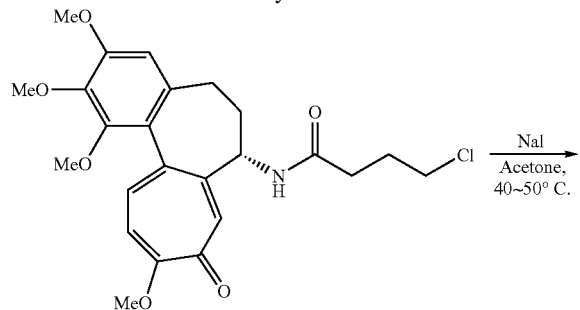

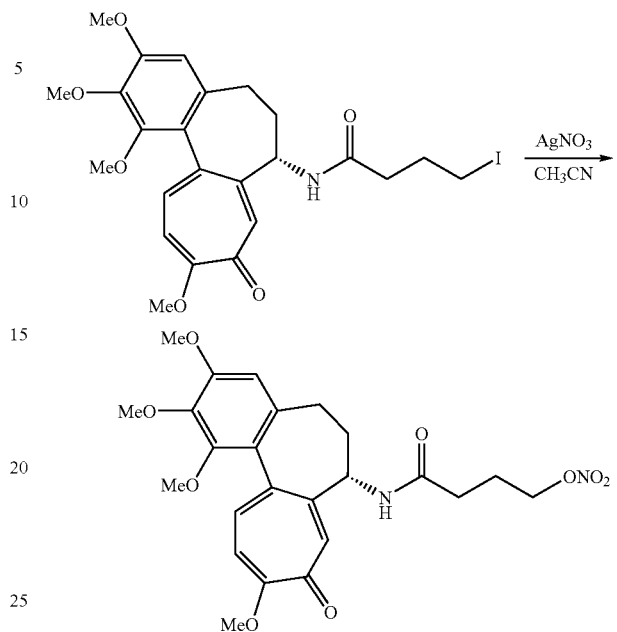

0.1 g (0.22 mmol) of the compound 1 obtained from the Example 1 was placed into a 10 ml flask and dissolved by adding the 5 ml of acetone. 0.097 g (0.065 mmol) of sodium iodide was added dropwise thereto, and then the mixture was stirred at temperature of 40~50° C. for 12 hours. The mixture was extracted with chloroform, dried over anhydrous magnesium sulfate and filtered, and then concentrated under reduced pressure to obtain 4-iodo-N-(1,2,3,10-tetramethoxy-9-oxo-5,6,7,9-tetrahydro-benzo[a]heptarene-7-yl)-butylamide (intermediate compound 1) (the first step reaction). The concentrated intermediate compound 1 and 2 ml of acetonitrile were placed into a 25 ml flask and 0.15 g (0.87 mmol) of silver nitrate was added thereto. After stirring for 12 hours, the mixture was filtered. The solvent was removed under reduced pressure. Chloroform was added thereto and the mixture was dried over sodium sulfate and filtered under reduced pressure. The resulting compound was purified by the column chromatography (ethylacetate:methanol=85:15) to obtain the title compound 4 as a yellow solid (53 mg, yields of the second step: 50%) (the second step reaction).

$^1$H NMR of the intermediate compound 1:

$^1$H NMR (500 MHz, CDCl$_3$) δ: 1.86–1.89 (m, 1H), 2.02–2.07 (m, 2H), 2.18–2.25 (m, 1H), 2.35–2.47 (m, 3H), 2.51–2.55 (m, 1H), 3.55 (t, 2H), 3.65 (s, 3H), 3.90 (s, 3H), 3.94 (s, 3H), 3.99 (s, 3H), 4.61–4.66 (m, 1H), 6.54 (s, 1H), 6.82 (d, 1H), 7.30 (d, 1H), 7.44 (s, 1H), 7.46 (d, 1H)

$^1$H NMR of the Compound 4:

$^1$H NMR (500 MHz, CDCl$_3$) δ: 1.96–1.20 (m, 3H), 2.29–2.39 (m, 4H), 2.51–2.52 (m, 1H), 3.66 (s, 3H), 3.91 (s, 3H), 3.95 (s, 3H), 4.01 (s, 3H), 4.40–4.44 (m, 2H), 4.65–4.67 (m, 1H), 6.54 (s, 1H), 6.89 (d, J=11.0 Hz, 1H), 7.36 (d, J=11.0 Hz, 1H), 7.51 (s, 1H), 7.55 (d, J=6.5 Hz, 1H)

MS m/z (relative intensity): 977.349([2M+H]$^+$, 17), 846.271(6), 527.12 (9), 489.165([M+H]$^+$, 100), 358.170 ([M+H]$^+$—CO(CH$_2$)$_3$ONO$_2$, 48), 341.46(48)

Example 5

Preparation of 4-nitrooxymethyl-N-(1,2,3,10-tetramethoxy-9-oxo-5,6,7,9-tetrahydro-benzo[a]heptarene-7-yl)-benzamide

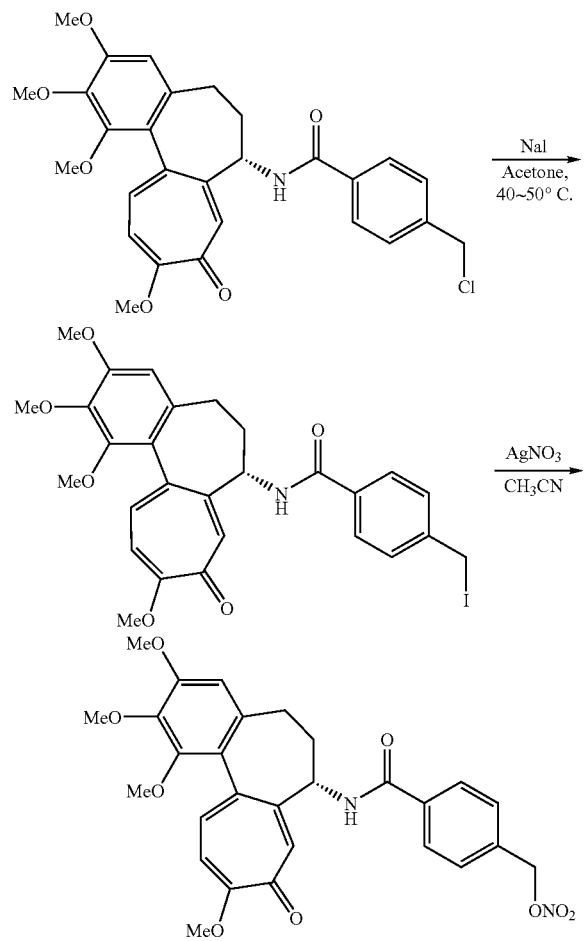

Example 6

Preparation of 3-nitrooxymethyl-N-(1,2,3,10-tetramethoxy-9-oxo-5,6,7,9-tetrahydro-benzo[a]heptarene-7-yl)-benzamide

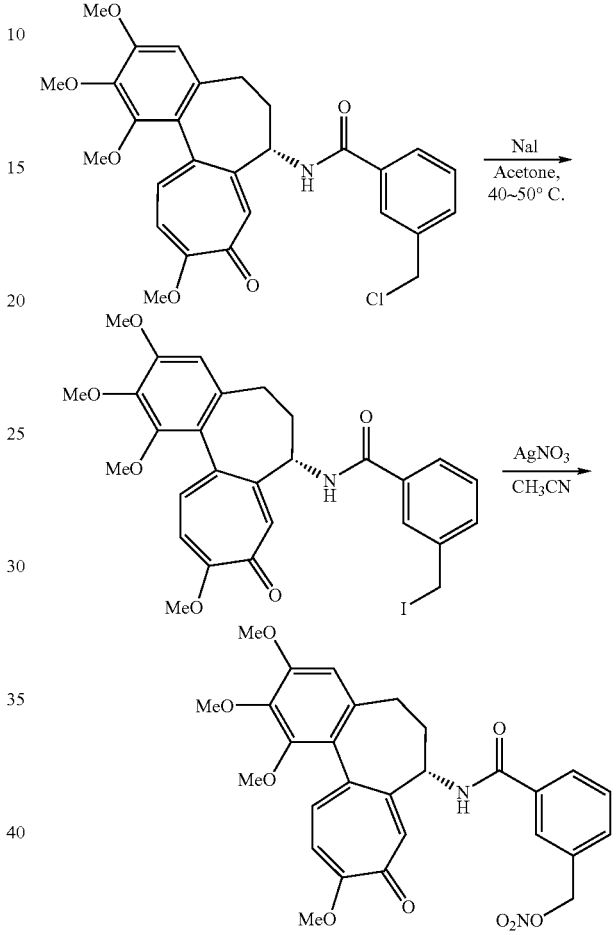

33 mg of the title compound 5 (yields of the second step reaction: 45%, as a yellow solid) was prepared by the same method of Example 4 through 4-iodomethyl-N-(1,2,3,10-tetramethoxy-9-oxo-5,6,7,9-tetra-hydro-benzo[a]heptarene-7-yl)-bezamide (intermediate compound 2) except for using compound 2 obtained from the Example 2.

$^1$H NMR of intermediate compound 2:

$^1$H NMR (500 MHz, CDCl$_3$) δ: 2.01–2.09 (m, 1H), 2.31–2.45 (m, 2H), 2.51–2.55 (m, 1H), 3.75 (s, 3H), 3.91 (s, 3H), 3.96 (s, 3H), 4.00 (s, 2H), 4.86–4.89 (m, 1H), 6.54 (s, 1H), 6.90 (d, 1H), 7.19 (d, 2H), 7.38 (d, 1H), 7.67 (s, 1H), 7.71 (d, 2H), 8.28 (d, J=6.5 Hz, 1H)

$^1$H NMR of compound 5:

$^1$H NMR (500 MHz, CDCl$_3$) δ: 2.02–2.09 (m, 1H), 2.35–2.58 (m, 3H), 3.76 (s, 3H), 3.91 (s, 3H), 3.97 (s, 3H), 4.01 (s, 3H), 4.86–4.91 (m, 1H), 5.30 (s, 2H), 6.56 (s, 1H), 6.92 (d, J=11.0 Hz, 1H), 7.19 (d, J=8.2 Hz, 2H), 7.41 (d, J=11.0 Hz, 1H), 7.70 (s, 1H), 7.81 (d, J=8.2 Hz, 2H), 8.36 (d, J=6.5 Hz, 1H)

25 mg of the title compound 6 (yields of the second step reaction: 42%, as a yellow solid) was prepared by the same method of Example 4 through 3-iodomethyl-N-(1,2,3,10-tetramethoxy-9-oxo-5,6,7,9-tetra-hydro-benzo[a]heptarene-7-yl)-benzamide (intermediate compound 3) except for using compound 3 obtained from the Example 3.

$^1$H NMR of the intermediate compound 3:

$^1$H NMR (500 MHz, CDCl$_3$) δ: 2.23–2.31 (m, 1H), 2.38–2.48 (m, 2H), 2.56–2.60 (m, 1H), 3.74 (s, 3H), 3.92 (s, 3H), 3.97 (s, 3H), 3.99 (s, 3H), 4.23 (d, 1H), 4.28 (d, 1H), 4.88–4.95 (m, 1H), 6.59 (s, 1H), 7.03 (d, 1H), 7.13 (t, 1H), 7.33 (d, 1H), 7.45 (d, 1H), 7.59 (d, 1H), 7.70 (s, 1H), 7.78 (s, 1H), 8.44 (d, 1H)

$^1$H NMR of the compound 6:

$^1$H NMR (500 MHz, CDCl$_3$) δ: 2.23–2.31 (m, 1H), 2.40–2.50 (m, 2H), 2.55–2.61 (m, 1H), 3.76 (s, 3H), 3.92 (s, 3H), 3.98 (s, 3H), 4.02 (s, 3H), 4.89–4.94 (m, 1H), 5.10 (d, J=12.3 Hz, 1H), 5.20 (d, J=12.3 Hz, 1H), 6.57 (s, 1H), 6.94 (d, J=11.0 Hz, 1H), 7.14 (t, J=7.9 Hz, 1H), 7.28 (d, J=7.9 Hz, 1H), 7.44 (d, J=11.0 Hz, 1H), 7.60 (d, J=7.9 Hz, 1H), 7.70 (s, 1H), 7.81 (s, 1H), 8.56 (d, J=6.5 Hz, 1H)

Example 7

Preparation of 4-chlroro-N-(1,2,3-trimethoxy-10-methyl-sulfonly-9-oxo-5,6,7,9-tetra-hydro-benzo[a]heptarene-7-yl)-butylamide.

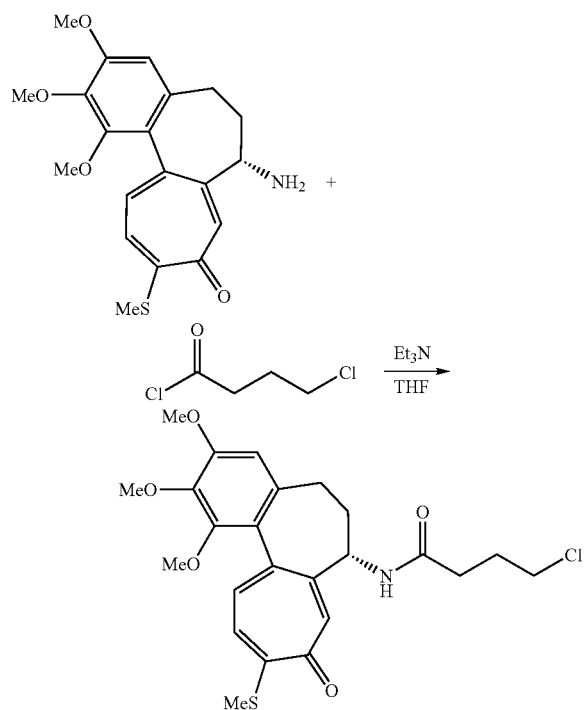

0.13 g of the title compound 7 (yields: 86%, as a yellow solid) was prepared by the same method of Example 1 except that thiodeacetylcolchicine was used instead of deacetylcolchicine.

$^{1}$H NMR (500 MHz, CDCl$_3$) δ: 1.86–1.93 (m, 1H), 2.00–2.10 (m, 2H), 2.23–2.31 (m, 1H), 2.37–2.55 (m, 4H), 2.45 (s, 3H), 3.53 (td, J=6.5, 1.5 Hz, 2H), 3.67 (s, 3H), 3.91 (s, 3H), 3.95 (s, 3H), 4.68–4.73 (m, 1H), 6.54 (s, 1H), 7.09 (d, J=10.6 Hz, 1H), 7.32 (d, J=10.6 Hz, 1H), 7.35 (d, J=7.3 Hz, 1H), 7.42 (s, 1H)

Example 8

Preparation of 4-chloro-N-(1,2,3-trimethoxy-10-methylsulfonyl-oxo-5,6,7,9-tetrahydro-benzo[a]heptarene-7-yl)-benzamide

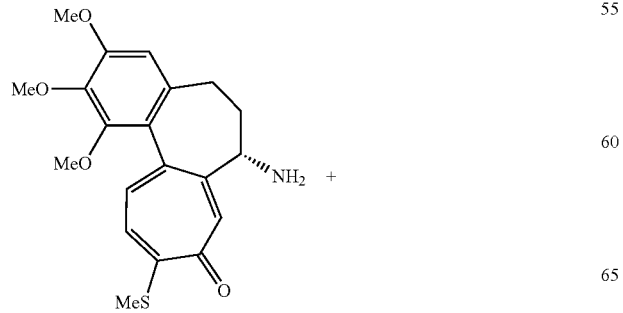

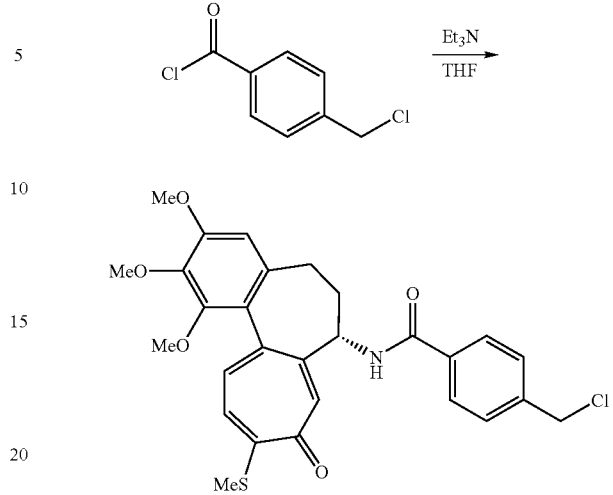

0.12 g of the title compound 8 (yields: 89%, as a yellow solid) was prepared by the same method of Example 1 except that thiodeacetylcolchicine and 3-chloromethylbenzoyl chloride were used instead of deacetylcochicine and 4-chlorobutyryl chloride, respectively.

$^{1}$H NMR (500 MHz, CDCl$_3$) δ: 2.09–2.15 (m, 1H), 2.31–2.38 (m, 1H), 2.41–2.48 (m, 1H), 2.44 (s, 3H), 2.55–2.59 (m, 1H), 3.75 (s, 3H), 3.91 (s, 3H), 3.97 (s, 3H), 4.47 (s, 2H), 4.90–4.95 (m, 1H), 6.56 (s, 1H), 7.10 (d, J=10.6 Hz, 1H), 7.25 (d, J=8.2 Hz, 2H), 7.35 (d, J=10.6 Hz, 1H), 7.56 (s, 1H), 7.84 (d, J=8.2 Hz, 2H), 8.11 (d, J=7.3 Hz, 1H)

Example 9

Preparation of 3-chloromethyl-N-(1,2,3-trimethoxy-10-methylsulfonyl-9-oxo-5,6,7,9-tetrahydro-benzo[a]heptarene-7-yl)-benzamide

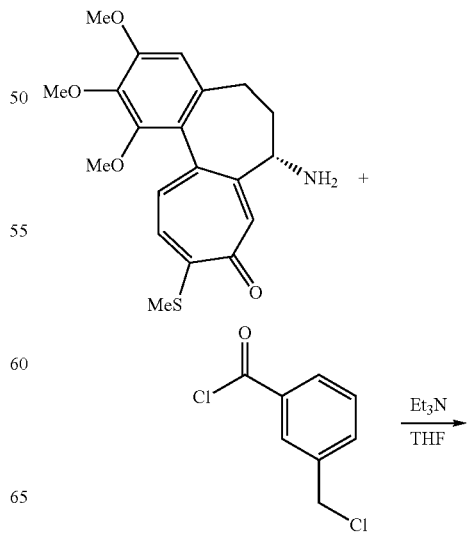

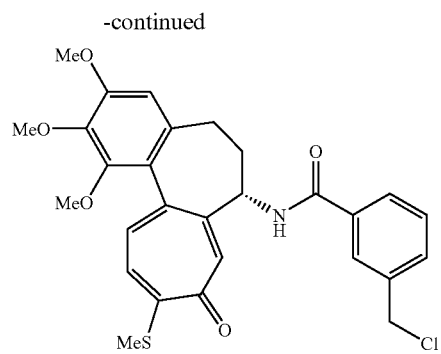

0.15 g of the title compound 9 (yields: 90%, as a yellow solid) was prepared by the same method of Example 1 except that thiodeacetylcolchicine and 4-chloromethylbenzoyl chloride were used instead of deacetylcolchicine and 4-chlorobutyryl chloride, respectively.

$^{1}$H NMR (500 MHz, CDCl$_3$) δ: 2.20–2.25 (m, 1H), 2.33–2.49 (m, 2H), 2.45 (s, 3H), 2.56–2.60 (m, 1H), 3.75 (s, 3H), 3.92 (s, 3H), 3.96 (s, 3H), 4.37 (d, 11.7 Hz, 1H), 4.41 (d, 11.7 Hz, 1H), 4.93–4.98(m, 1H), 6.57 (s, 1H), 7.13 (d, J=10.6 Hz, 1H), 7.17 (t, J=7.6 Hz, 1H), 7.34 (d, J=7.6 Hz, 1H), 7.38 (d, J=10.6 Hz, 1H), 7.65 (s, 1H), 7.67 (d, J=7.6 Hz, 1H), 7.77 (s, 1H), 8.35 (d, J=7.3 Hz, 1H)

Example 10

Preparation of 4-nitrooxy-N-(1,2,3-trimethoxy-10-methylsulfonyl-9-oxo-5,6,7,9-tetrahydro-benzo[a]heptarene-7-yl)-butylamide

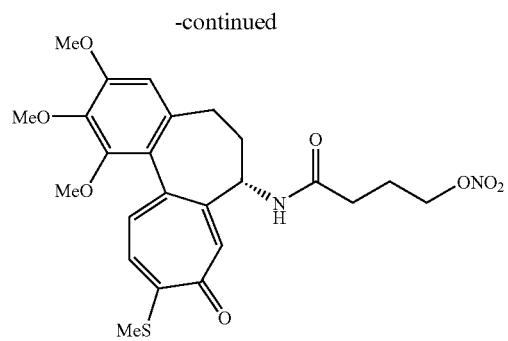

30 mg of the title compound 10 (yields of second step reaction: 33%, as a yellow solid) was prepared by the same method of Example 4 through 4-iodo-N-(1,2,3-trimethoxy-10-methylsulfonyl-9-oxo-5,6,7,9-tetrahydro-benzo[a]heptarene-7-yl)-butylamide (intermediate compound 4) except for using compound 7 obtained from the Example 7.

$^{1}$H NMR of intermediate compound 4:
$^{1}$H NMR (500 MHz, CDCl$_3$) δ: 1.92–1.98 (m, 1H), 2.01–2.12 (m, 2H), 2.24–2.55 (m, 5H), 2.45 (s, 3H), 3.50–3.54 (m, 2H), 3.68 (s, 3H), 3.91 (s, 3H), 3.95 (s, 3H), 4.71–4.74 (m, 1H), 6.55 (s, 1H), 7.11 (d, 1H), 7.34 (d, 1H), 7.53 (s, 1H), 7.98 (d, 1H)

$^{1}$H NMR of compound 10:
$^{1}$H NMR (500 MHz, CDCl$_3$) δ: 1.87–1.93 (m, 1H), 1.96–2.06 (m, 2H), 2.24–2.55 (m, 5H), 2.45 (s, 3H), 3.67 (s, 3H), 3.91 (s, 3H), 3.95 (s, 3H), 4.42–4.47 (m, 2H), 4.70–4.75 (m, 1H), 6.54 (s, 1H), 7.11 (d, J=10.6 Hz, 1H), 7.34 (d, J=10.6 Hz, 1H), 7.49 (s, 1H), 7.69 (d, J=7.6 Hz, 1H)

Example 11

Preparation of 4-nitrooxymethyl-N-(1,2,3-trimethoxy-10-methylsulfonyl-9-oxo-5,6,7,9-tetrahydro-benzo[a]heptarene-7-yl)-benzamide

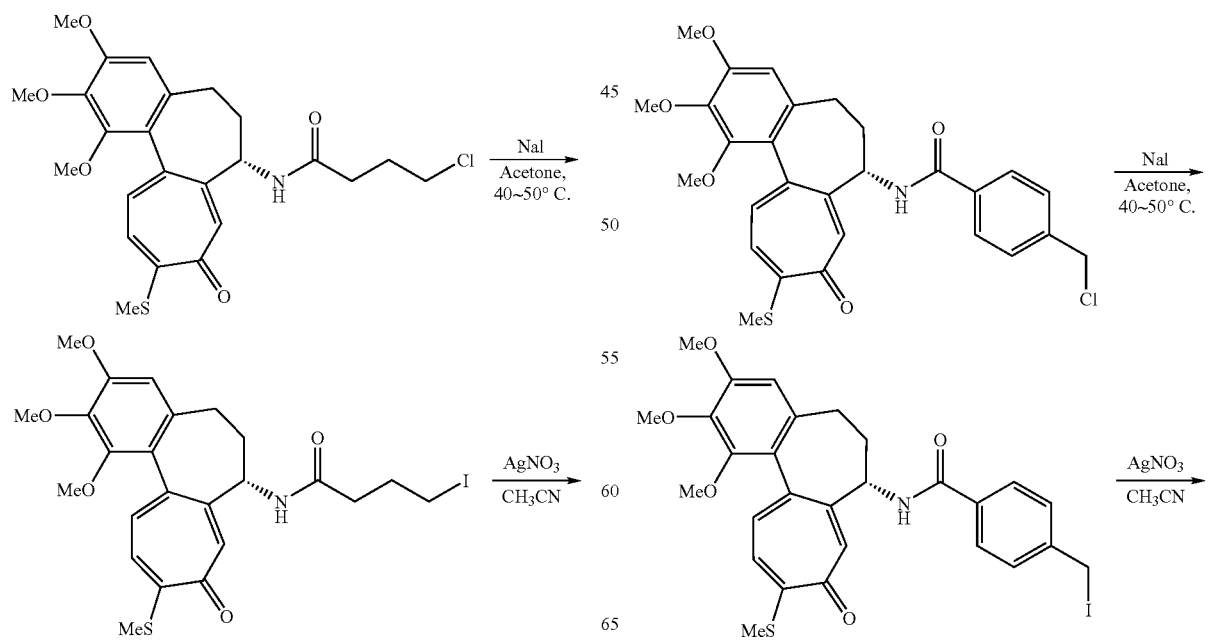

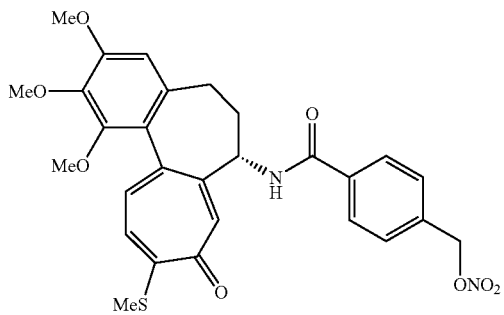

75 mg of the title compound 11 (yields of second step reaction: 58%, as a yellow solid) was prepared by the same method of Example 4 through 4-iodomethyl-N-(1,2,3-trimethoxy-10-methylsulfonyl-9-oxo-5,6,7,9-tetrahydro-benzo[a]heptarene-7-yl)-benzamide (intermediate compound 5) except for using compound 8 obtained from the Example 8.

¹H NMR of intermediate compound 5:

¹H NMR (500 MHz, CDCl₃) δ: 2.15–2.20 (m, 1H), 2.28–2.35 (m, 1H), 2.38–2.44 (m, 1H), 2.44 (s, 3H), 2.53–2.56 (m, 1H), 3.75 (s, 3H), 3.90 (s, 3H), 3.96 (s, 3H), 4.27 (s, 2H), 4.92–4.97 (m, 1H), 6.56 (s, 1H), 7.12 (d, 1H), 7.17 (d, 2H), 7.36 (d, 1H), 7.67 (s, 1H), 7.80 (d, 2H), 8.67 (d, 1H)

¹H NMR of compound 11:

¹H NMR (500 MHz, CDCl₃) δ: 2.14–2.20 (m, 1H), 2.30–2.48 (m, 2H), 2.45 (s, 3H), 2.55–2.59 (m, 1H), 3.76 (s, 3H), 3.91 (s, 3H), 3.97 (s, 3H), 4.93–4.98 (m, 1H), 5.29 (s, 2H), 6.56 (s, 1H), 7.13 (d, J=10.6 Hz, 1H), 7.20 (d, J=8.5 Hz, 2H), 7.37 (d, J=10.6 Hz, 1H), 7.66 (s, 1H), 7.90 (d, J=8.5 Hz, 2H), 8.64 (d, J=7.3 Hz, 1H)

Example 12

Preparation of 3-nitrooxymethyl-N-(1,2,3-trimethoxy-10-methylsulfonyl-9-oxo-5,6,7,9-tetrahydro-benzo[a]heptarene-7-yl)-benzamide

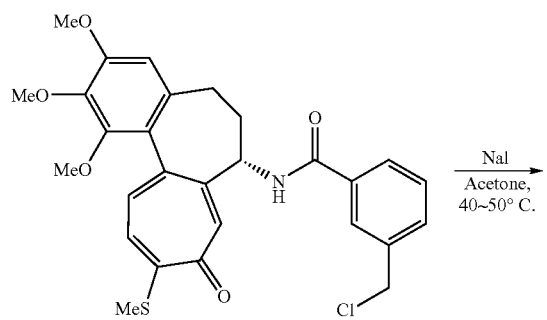

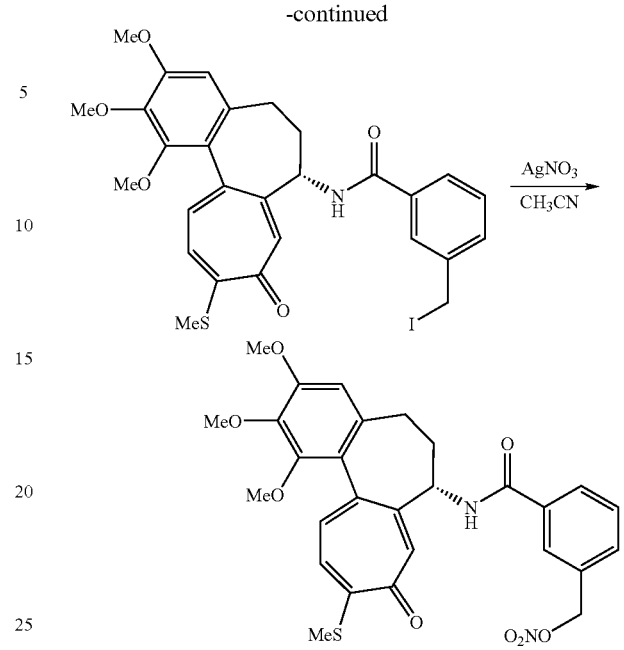

70 mg of the title compound 12 (yields of second step reaction: 64%, as a yellow solid) was prepared by the same method of Example 4 through 3-iodomethyl-N-(1,2,3-trimethoxy-10-methylsulfonyl-9-oxo-5,6,7,9-tetrahydro-benzo[a]heptarene-7-yl)-benzamide (intermediate compound 6) except for using compound 9 obtained from the Example 9.

¹H NMR of intermediate compound 6:

¹H NMR (500 MHz, CDCl₃) δ: 2.26–2.45 (m, 3H), 2.45 (s, 3H), 2.54–2.58 (m, 1H), 3.75 (s, 3H), 3.91 (s, 3H), 3.97 (s, 3H), 4.16 (d, 1H), 4.23 (d, 1H), 4.95–5.00 (m, 1H), 6.57 (s, 1H), 7.05 (t, 1H), 7.16 (d, 1H), 7.26 (d, 1H), 7.39 (d, 1H), 7.60 (d, 1H), 7.77 (s, 1H), 7.80 (s, 1H), 8.82 (d, 1H)

¹H NMR of compound 12:

¹H NMR (500 MHz, CDCl₃) δ: 2.31–2.47 (m, 3H), 2.45 (s, 3H), 2.57–2.61 (m, 1H), 3.77 (s, 3H), 3.92 (s, 3H), 3.98 (s, 3H), 4.94–4.99 (m, 1H), 5.10 (d, 12.0 Hz, 1H), 5.18 (d, 12.0 Hz, 1H), 6.57 (s, 1H), 7.12 (t, J=7.6 Hz, 1H), 7.18 (d, J=10.6 Hz, 1H), 7.25 (d, J=7.6 Hz, 1H), 7.42 (d, J=10.6 Hz, 1H), 7.69 (s, 1H), 7.78–7.79 (m, 2H), 9.02 (d, J=7.3 Hz, 1H)

Example 13

Preparation of N-(7-acetylamino-1,2,3-trimethoxy-9-oxo-5,6,7,9-tetrahydro-benzo[a]heptarene-10-yl)-4-chloromethyl-benzamide

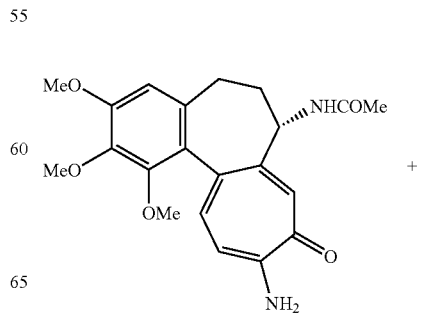

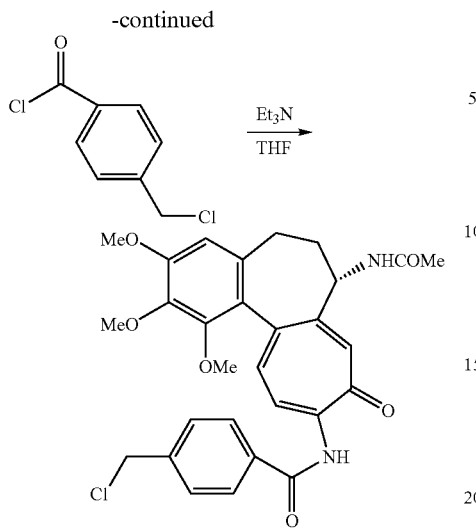

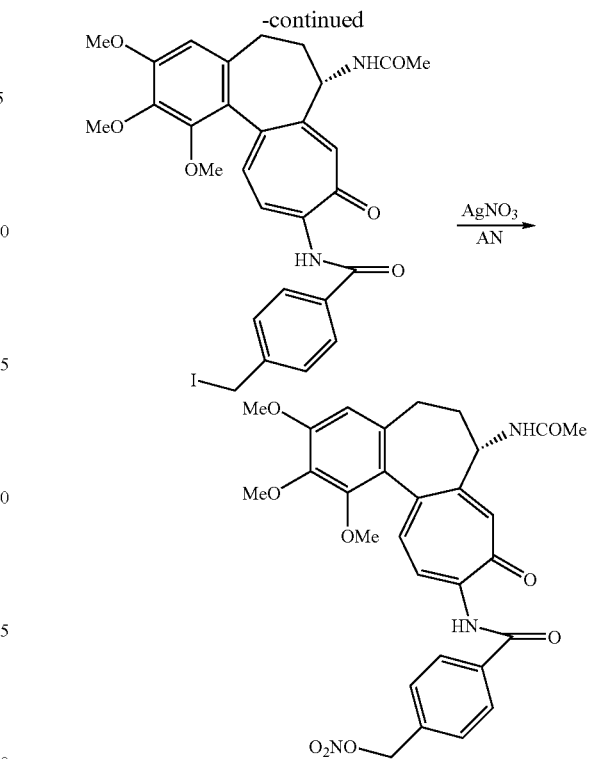

1 g (26 mmol) of N-(10-amino-1,2,3-trimethoxy-9-oxo-5,6,7,9-tetrahydro benzo[a]heptarene-7-yl) acetamide was placed into a 25 ml flask and dissolved with 10 ml of tetrahydrofuran. 2.8 ml (20 mmol) of triethylamine was added thereto dropwise, and then the mixture was stirred for 30 minutes. 0.55 g (2.9 mmol) of 4-chloromethylbenzoyl chloride was added thereto and dissolved with stirring at room temperature for 48 hours, extracted with chloroform, dried over anhydrous magnesium sulfate and then filtered. After concentrating under reduced pressure, the concentrated resulting compound was purified through the column chromatography (chloroform:methanol=9:1) to obtained 1.36 g of the title compound 13 (yields: 98%, as a yellow solid).

$^1$H NMR (500 MHz, CDCl$_3$) δ: 1.87 (m, 1H), 2.02 (s, 3H), 2.39 (m, 1H), 2.41 (m, 1H), 2.53 (m, 1H), 3.67 (s, 3H), 3.91 (s, 3H), 3.92 (s, 3H), 4.68 (s, 2H), 4.71 (m, 1H), 6.54 (s, 1H), 6.94 (d, J=10.0 Hz, 1H), 7.54~7.67 (m, 4H), 8.00 (m, 2H), 9.21 (d, J=10.9 Hz, 1H), 10.32 (s, 1H)

Example 14

Preparation of N-(7-acetylamino-1,2,3-trimethoxy-9-oxo-5,6,7,9-tetrahydro-benzo[a]heptarene-10-yl)-4-nitrooxymethyl-benzamide

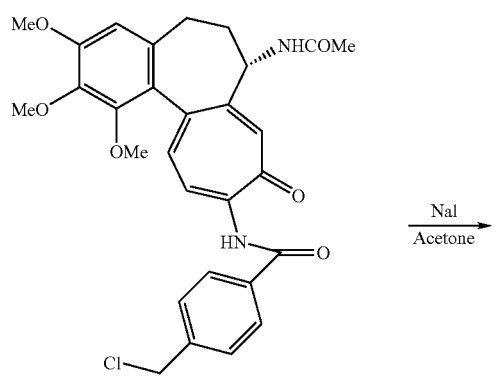

The compound 13 obtained from the Example 13 was dissolved using 5 ml of acetone. 0.072 g (0.48 mmol) of the sodium iodide was added dropwise thereto. After stirring at 40~50° C. for 24 hours, the mixture was extracted with chloroform, dried over anhydrous magnesium sulfate and filtered. The mixture was concentrated under reduced pressure to obtain N-(7-acetylamino-1,2,3-trimethoxy-9-oxo-5,6,7,9-tetrahydro-benzo[a]heptarene-10-yl)-4-iodidmethyl benzamide (intermediate compound 7). 0.0205 g (0.033 mmol) of the concentrated intermediate compound 7 and 0.2 ml of the acetonitrile were placed into a 25 ml flask and 0.022 g (0.13 mmol) of silver nitrate was added thereto. After stirring for 24 hours, the mixture was filtered, and followed by concentrating under reduced pressure, and chloroform was added thereto. The resulting mixture was dried over sodium sulfate, filtered, and followed by concentrating under reduced pressure. 18 mg of the title compound 14 (yields of second step reaction: 96%, as a yellow solid) was obtained after purification by column chromatography (chloroform:methanol=9:1)

$^1$H NMR of intermediate compound 7:

$^1$H NMR (500 MHz, CDCl$_3$) δ: 1.85 (m, 1H), 2.02 (s, 3H), 2.29 (m, 1H), 2.40 (m, 1H), 2.54 (m, 1H), 3.66 (s, 3H), 3.91 (s, 3H), 3.95 (s, 3H), 4.50 (s, 2H), 4.69 (m, 1H), 6.54 (s, 1H), 6.85 (d, J=6.75 Hz, 1H), 7.53 (m, 3H), 7.60 (s, 1H), 7.93 (d, J=8.2 Hz, 2H), 9.20 (d, J=10.9 Hz, 1H), 10.30 (s, 1H)

$^1$H NMR of compound 14:

$^1$H NMR (500 MHz, CDCl$_3$) δ: 1.85 (m, 1H), 2.02 (s, 3H), 2.29 (m, 1H), 2.41 (m, 1H), 2.54 (m, 1H), 3.66 (s, 3H), 3.91 (s, 3H), 3.94 (s, 3H), 4.69 (m, 1H), 5.52 (s, 2H), 6.54 (s, 1H), 6.73 (d, J=6.8 Hz, 1H), 7.51~7.60 (m, 4H), 8.03 (m, 2H), 9.19 (d, J=10.9 Hz, 1H), 10.33 (s, 1H)

Example 15

Preparation of 4-chloromethyl-benzoic acid-7-acetylamino-1,2,3,10-tetramethoxy-9-oxo-5,6,7,9-tetrahydro-benzo[a]heptarene-7-yl-methyl ester

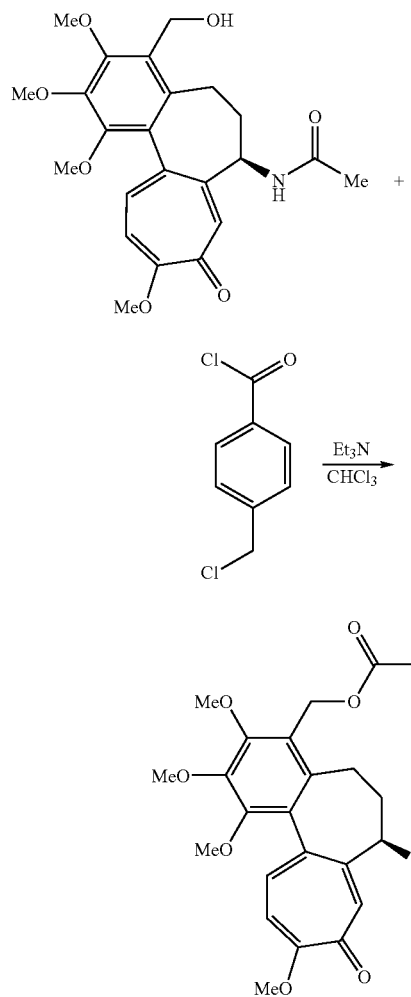

0.05 g (0.12 mmol) of 4-hydroxymethylcolchicine (N-(4-hydroxymethyl-1,2,3,10-tetramethoxy-9-oxo-5,6,7,9-tetrahydro-benzo[a]-heptarene-7-yl)-acetamide) was placed into a 10 ml flask and 3.5 ml of chloroform was added thereto to dissolve the compound. To the mixture, 0.13 ml (0.096 mmol) of triethylamine was added dropwise and then 0.088 mg (0.48 mmol) of 4-chloromethylbenzoyl chloride was added slowly. After stirring for 18 hours, the mixture was extracted with chloroform, dried and filtered over anhydrous magnesium sulfate, and the solvent was removed under reduced pressure. Concentrated resulting compounds was purified using the column chromatography (ethylacetate:methanol=85:15) to obtain 0.034 g of the title compound 15 (yields: 50.2%) as a white solid.

$^1$H NMR (500 MHz, CDCl$_3$) δ: 1.85–1.87 (m, 1H), 1.99 (s, 3H), 2.21–2.23 (m, 2H), 2.92–2.94 (m, 1H), 3.67 (s, 3H), 3.98 (s, 3H), 4.00 (s, 3H), 4.02 (s, 3H), 4.61 (s, 3H), 4.67–4.69 (m, 1H), 5.40 (d, J=11.15 Hz, 1H), 5.46 (d, J=11.15 Hz, 1H), 6.86 (d, J=11.15 Hz, 1H), 7.30 (d, J=10.85 Hz, 1H), 7.45 (d, J=8.80 Hz, 2H), 7.55 (s, 1H), 7.80 (d, J=6.75 Hz, 1H), 8.03 (d, J=8.80 Hz, 2H)

Example 16

Preparation of 4-chloromethyl-benzoic acid-7-acetylamino-1,2,3-trimethoxy-10-methylsulfonyl-9-oxo-5,6,7,9-tetrahydro-benzo[a]heptarene-7-yl-methyl-ester

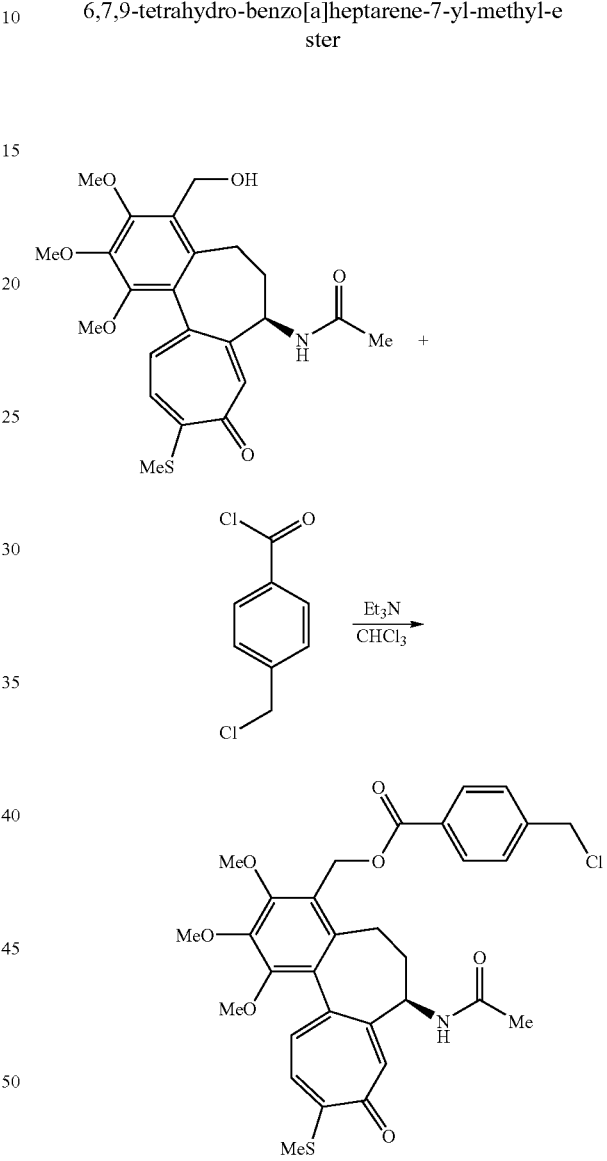

0.12 g of the title compound 16 (yields: 40%, as a yellow solid) was prepared by the same method of Example 15 except that 4-hydroxymethylthiocolchicine was used instead of 4-hydroxymethylcolchicine.

$^1$H NMR (500 MHz, CDCl$_3$) δ: 1.83–1.85(m, 1H), 2.02 (s, 3H), 2.19–2.21(m, 2H), 2.43 (s, 3H), 2.92–2.94(m, 1H), 3.67 (s, 3H), 3.98 (s, 3H), 4.00 (s, 3H), 4.61 (s, 2H), 4.64–4.66 (m, 1H), 5.41 (d, J=11.15 Hz, 1H), 5.46 (d, J=11.15 Hz, 1H), 7.06 (d, J=10.56 Hz, 1H), 7.27 (d, J=9.39 Hz, 1H), 7.38 (s, 1H), 7.45 (d, J=8.51 Hz, 2H), 7.50 (d, J=7.33 Hz, 1H), 8.03 (d, J=8.51 Hz, 2H)

Example 17

Preparation of 4-chlorobutyric acid-7-acetylamino-1,2,3,10-tetramethoxy-9-oxo-5,6,7,9-tetrahydro-benzo[a]heptarene-7-yl-methyl ester

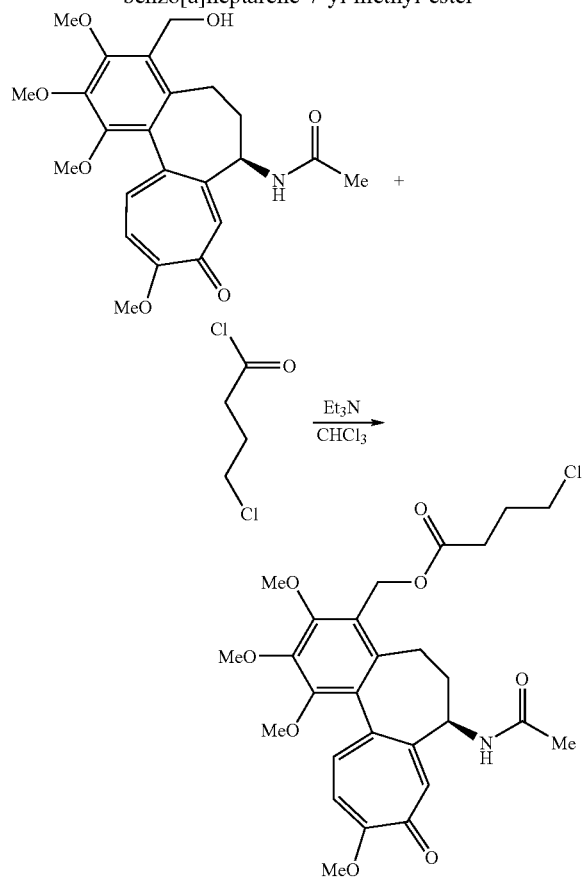

0.13 g of the title compound 17 (yields: 92%, as a yellow solid) was prepared by the same method of Example 15 except that 4-chlolobutyryl chloride was used instead of 4-chloromethylbenzoyl chloride.

$^1$H NMR (500 MHz, CDCl$_3$) δ: 1.91–1.93(m, 1H), 2.00 (s, 3H), 2.10–2.12 (m, 2H), 2.23–2.25 (m, 2H), 2.55 (t, J=7.04 Hz, 2H), 2.82–2.84 (m, 1H), 3.63 (t, J=6.16 Hz, 2H), 3.65 (s, 3H), 3.96 (s, 3H), 3.98 (s, 3H), 4.03 (s, 3H), 4.63–4.66 (m, 1H), 5.12 (d, J=12.91 Hz, 1H), 5.27 (d, J=12.91 Hz, 1H), 6.90 (d, J=11.15 Hz, 1H), 7.30 (d, J=9.68 Hz, 1H), 7.61 (s, 1H), 8.21 (d, J=6.45 Hz, 1H)

Example 18

Preparation of 4-chloro-butyric acid-7-acetylamino-1,2,3-trimethoxy-10-methyl-sulfonyl-9-oxo-5,6,7,9-tetrahydro-benzo[a]heptarene-7-yl-methyl ester

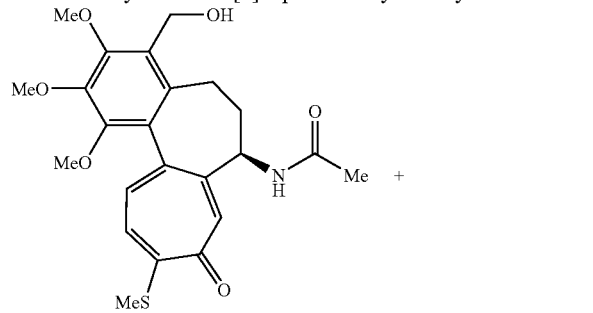

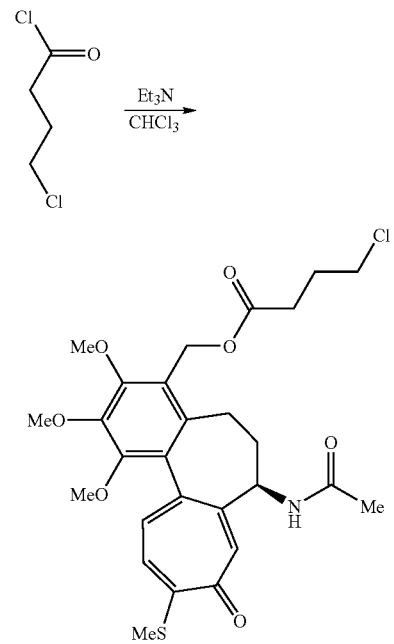

0.13 g of the title compound 18 (yields: 92%, as a yellow solid) was prepared by the same method of Example 15 except that 4-hydroxymethyl thiocolchicine and 4-chlorobutyryl chloride were used instead of 4-hydroxymethyl colchicine and 4-chloromethylbenzoyl chloride, respectively.

$^1$H NMR (500 MHz, CDCl$_3$) δ: 1.85–1.87 (m, 1H), 2.03 (s, 3H), 2.12–2.14 (m, 2H), 2.19–2.21 (m, 2H), 2.45 (s, 3H), 2.53 (t, J=7.33 Hz, 2H), 2.81–2.83 (m, 1H), 3.60 (t, J=6.75 Hz, 2H), 3.65 (s, 3H), 3.96 (s, 3H), 3.98 (s, 3H), 4.64–4.66 (m, 1H), 5.17 (d, J=12.03 Hz, 1H), 5.26 (d, J=12.03 Hz, 1H), 7.07 (d, J=10.56 Hz, 1H), 7.26 (d, J=10.27 Hz, 1H), 7.37 (s, 1H), 7.40 (d, J=7.04 Hz, 1H)

Example 19

Preparation of 4-nitrooxymethyl-benzoic acid-7-acetylamino-1,2,3,10-tetra-methoxy-9-oxo-5,6,7,9-tetrahydro-benzo[a]heptarene-4-yl-methyl-ester

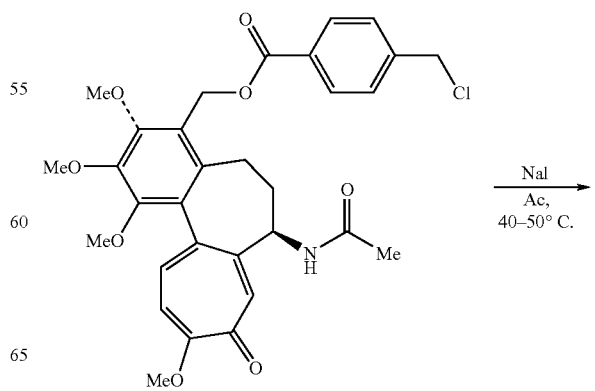

35

-continued

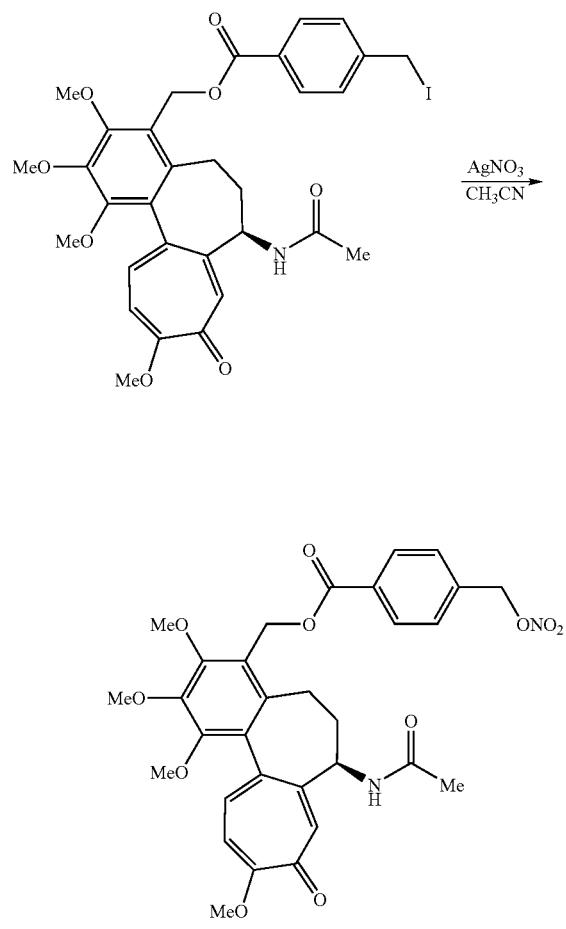

0.084 g (0.14 mmol) of the compound 15 obtained from the Example 15 (0.14 mmol) was placed into the flask and then dissolved by adding 5 ml of acetone. After adding 0.086 g of sodium iodide(0.057 mmol) dropwisely thereto, the mixture was stirred at 40~50° C. for 12 hours, extracted with chloroform, dried over anhydrous magnesium sulfate, and then concentrated under reduced pressure. Concentrated resulting compound and 2 ml acetonitrile were placed with a 25 ml flask and 0.09 g (0.53 mmol) of silver nitrate was added thereto. The mixture was stirred for 12 hours, and the solvent was filtered and removed under reduced pressure. The resulting compound was purified by column chromatography (ethylacetate:methanol=85:15) to obtain 40 mg of the title compound 19 (yields of second step reaction: 46%) as a yellow solid.

$^1$H NMR of compound 19:

$^1$H NMR (500 MHz, CDCl$_3$) δ: 1.86–1.88 (m, 1H), 1.77 (s, 1H), 2.20–2.22 (m, 2H), 2.92–2.94 (m, 1H), 3.67 (s, 3H), 3.98 (s, 3H), 3.99 (s, 3H), 4.00 (s, 3H), 4.67–4.69 (m, 1H), 5.39–5.47 (m, 2H), 5.47 (s, 2H), 6.86 (d, J=10.85 Hz, 1H), 7.30 (d, J=10.85 Hz, 1H), 7.47 (d, J=8.51 Hz, 2H), 7.54 (s, 1H), 7.76 (d, J=7.04 Hz, 1H), 8.01 (d, J=8.51 Hz, 2H),

36

Example 20

Preparation of 4-nitrooxymethyl-butyric acid-7-acetylamino-1,2,3-trimethoxy-10-methylsulfonyl-9-oxo-5,6,7,9-tetrahydro-benzo[a]heptarene-4-yl-methyl-ester

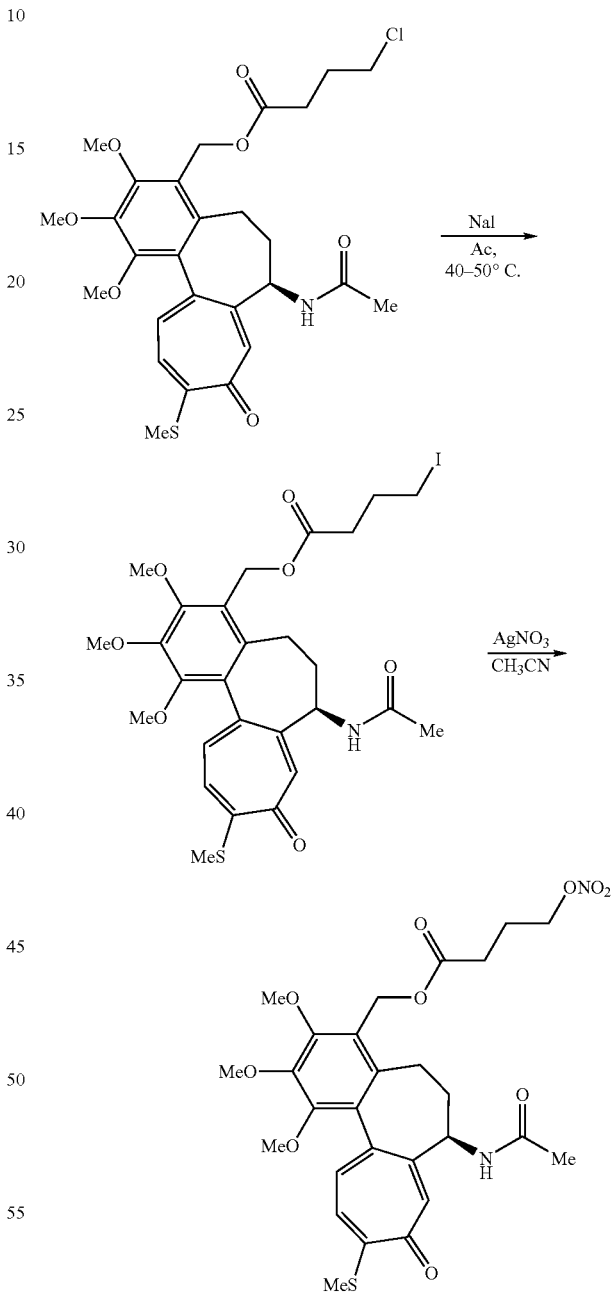

70 mg of the title compound 20 (yields of second step reaction: 39%, as a yellow solid) was prepared by the same method of the Example 19 through 4-iodomethyl-butyric acid-7-acetylamido-1,2,3-trimethoxy-10-methylsulfonyl-9-oxo-5,6,7,9-tetrahydro-benzo[a]heptarene-4-yl-methyl-ester (intermediate compound 8) except for using compound 18 obtained from the Example 18.

¹H NMR of intermediate compound 8:

¹H NMR (500 MHz, CDCl₃) δ: 1.82–1.84 (m, 1H), 2.02 (s, 3H), 2.13–2.15 (m, 4H), 2.44 (s, 3H), 2.47 (t, J=7.04 Hz, 2H), 2.82–2.84 (m, 1H), 3.24 (t, J=6.75 Hz, 2H), 3.65 (s, 3H), 3.95 (s, 3H), 3.97 (s, 3H), 4.63–4.65 (m, 1H), 5.17 (d, J=11.73 Hz, 1H), 5.25 (d, J=11.73 Hz, 1H), 6.65 (d, J=7.33 Hz, 1H), 7.05 (d, J=10.27 Hz, 1H), 7.23 (d, J=10.27 Hz, 1H), 7.27 (s, 1H)

¹H NMR of compound 20:

¹H NMR (500 MHz, CDCl₃) δ: 1.90–1.92 (m, 1H), 2.02 (s, 3H), 2.08–2.10 (m, 2H), 2.18–2.20 (m, 2H), 2.45 (s, 3H), 2.49 (t, J=7.04 Hz, 2H), 2.81–2.83 (m, 1H), 3.65 (s, 3H), 3.96 (s, 3H), 3.97 (s, 3H), 4.54 (t, J=6.45 Hz, 2H), 4.65–4.67 (m, 1H), 5.18 (d, J=11.73 Hz, 1H), 5.27 (d, J=11.73 Hz, 2H), 7.10 (d, J=11.15 Hz, 1H), 7.26 (d, J=9.68 Hz, 1H), 7.45 (s, 1H), 8.00 (d, J=7.04 Hz, 1H)

Example 21

Preparation of 4-nitrooxymethyl-benzoic acid-7-acetylamino-1,2,3-trimethoxy-10-methylsulfonyl-9-oxo-5,6,7,9,-tetrahydro-benzo[a]heptarene-4-yl-methyl-ester

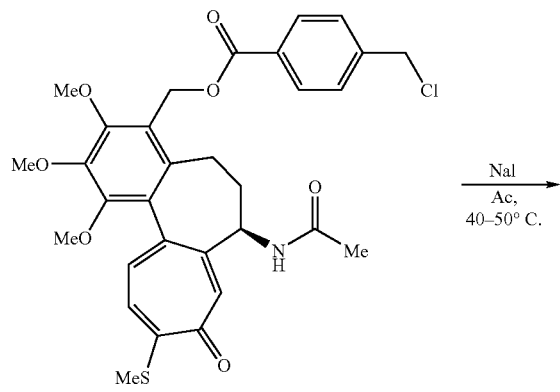

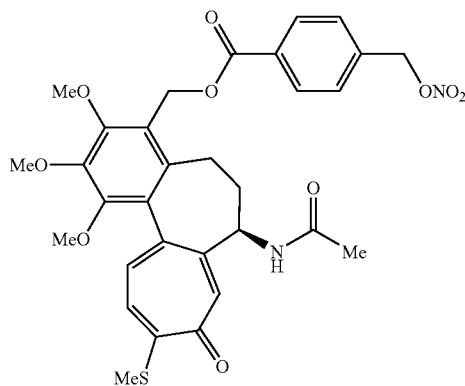

70 mg of the title compound 21 (yields of second step reaction: 45%, as a yellow solid) was prepared by the same method of the Example 19 through 4-iodomethyl-benzoic acid-7-acetylamino-1,2,3-trimethoxy-10-methylsulfonyl-9-oxo-5,6,7,9-tetrahydro-benzo[a]heptarene-4-yl-methyl-ester(intermediate compound 9) except for using compound 16 obtained from the Example 16.

¹H NMR of intermediate compound 9:

¹H NMR (500 MHz, CDCl₃) δ: 1.74–1.76 (m, 1H), 2.23 (s, 3H), 2.13–2.15 (m, 1H), 2.23–2.25 (m, 1H), 2.43 (s, 3H), 2.92–2.94 (m, 1H), 3.66 (s, 3H), 3.97 (s, 3H), 3.99 (s, 3H), 4.45 (s, 2H), 4.66–4.68 (m, 1H), 5.40 (d, J=12.03 Hz, 1H), 5.45 (d, J=12.03 Hz, 1H), 6.35 (d, J=6.45 Hz, 1H), 7.05 (d, J=9.97 Hz, 1H), 7.24 (d, J=7.24 Hz, 1H), 7.22 (s, 1H), 7.41 (d, J=8.51 Hz, 2H), 7.96 (d, J=8.51 Hz, 2H)

¹H NMR of compound 21:

¹H NMR (500 MHz, CDCl₃) δ: 1.79–1.81 (m, 1H), 2.00 (s, 3H), 2.13–2.15 (m, 1H), 2.23–2.25 (m, 1H), 2.43 (s, 3H), 2.92–2.94 (m, 1H), 3.67 (s, 3H), 3.97 (s, 3H), 3.99 (s, 3H), 4.66–4.68 (m. 1H), 5.42–5.47 (m, 2H), 5.47 (s, 2H), 6.95 (d, J=6.75 Hz, 1H), 7.05 (d, J=10.56 Hz, 1H), 7.24 (d, J=10.85 Hz, 1H), 7.30 (s, 1H), 7.46 (d, J=8.21 Hz, 2H), 8.07 (d, J=8.21 Hz, 2H)

Example 22

Deacetamidocolchicine-7-ol

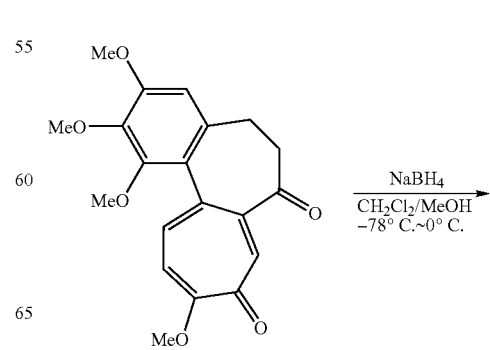

-continued

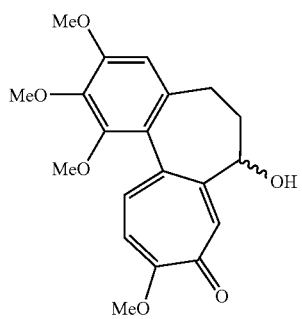

2.29 g (6.426 mmol) of colchicine, 20 ml of methanol and 20 ml of chloromethane were placed into a 100 ml flask and cooled to −78° C. To the mixture, 0.729 g (19.278 mmol) of sodium borohydride was added and the mixture was warmed to 0∼−20° C. with stirring for 5 hours. The solution was acidified with 50% acetic acid and extracted with chloroform, and then dried over sodium sulfate, filtered and the solvent was removed under reduced pressure. The concentrated resulting compound was recrystallized (methanol/ethylether) to obtain the title compound 22(2.0844 g, 90.5%).

$^1$H NMR (500 MHz, CDCl$_3$): δ 1.80–1.83 (m, 1H), 2.40–2.49 (m, 3H), 3.26 (br, 1H), 3.60 (s, 3H), 3.90 (s, 3H), 3.91 (s, 3H), 3.97 (s, 3H), 4.46–4.49 (m, 1H), 6.55 (s, 1H), 6.79 (d, J=11.0 Hz, 1H), 7.18 (d, J=11.0 Hz, 1H), 7.94 (s, 1H)

Example 23

Preparation of (−)-4,7,7-trimethyl-3-oxo-2-oxa-bicyclo[2.2.1]heptane-1-carboxylic acid-1,2,3,10-tetramethoxy-9-oxo-5,6,7,9-tetrahydro-benzo[a]heptalene-7-yl ester and (+)-4,7,7-trimethyl-3-oxo-2-oxabicyclo[2.2.1]heptane-1-carboxcylic acid-1,2,3,10-tetramethoxy-9-oxo-5,6,7,9-tetrahydro-benzo[a]heptalene-7-yl ester

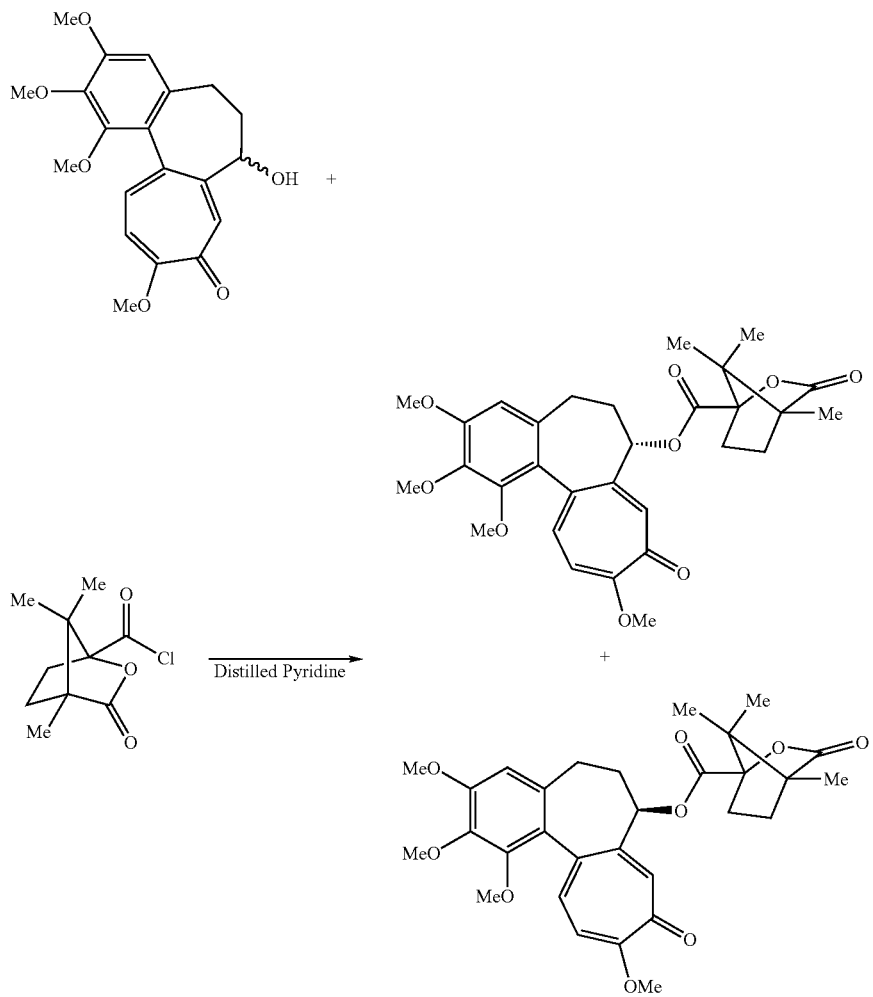

0.5098 g (1.4225 mmol) of deacetamidocolchicine-7-ol was placed into a 10 ml flask and 8 ml of distilled pyridine was added thereto. To the mixture, (−)-camphanic chloride (0.4007 g, 1.8492 mmol) was added. After 3 hours, 1N hydrochloric acid was added to stop the reaction. The mixture was extracted with ethyl acetate for three times, and then dried over anhydrous sodium sulfate and filtered, and the compound was concentrated under reduced pressure. The concentrated compound was purified by column chromatography (ethyl acetate) to obtain the racemates of the title compounds 23(1) and 23(2). The racemates were separated by MPLC (ethanol:isopropyl alcohol=9:1) to obtain the compounds 23(1) (184.6 mg, 24.1%) and 23(2) (191.5 mg, 25.0%).

$^1$H NMR of compound 23(1):

$^1$H NMR (500 MHz, CDCl$_3$): δ 0.95 (s, 3H), 1.10 (s, 3H), 1.11 (s, 3H), 1.71–1.74 (m, 1H), 1.90–1.93 (m, 1H), 2.05–2.13 (m, 2H), 2.14–2.43 (m, 2H), 2.49–2.52 (m, 1H), 2.54–2.58 (m, 1H), 3.66 (s, 3H), 3.92 (m, 3H), 3.94 (s, 3H), 3.99 (s, 3H), 5.41 (dd, J=7.0, 11.0 Hz, 1H), 6.56 (s, 1H), 6.80 (d, J=11.0 Hz, 1H), 7.28 (d, J=11.0 Hz, 1H), 7.40 (s, 1H)

$^1$H NMR of compound 23(2):

$^1$H NMR (500 MHz, CDCl$_3$): δ 1.02 (s, 3H), 1.07 (s, 3H), 1.12 (s, 3H), 1.71–1.74 (m, 1H), 1.92–1.95 (m, 1H), 2.07–2.11 (m, 2H), 2.35–2.43 (m, 1H), 2.48–2.56 (m, 3H), 3.66 (s, 3H), 3.91 (m, 1H), 3.94 (s, 3H), 3.99 (s, 3H), 5.46 (dd, J=7.0, 11.0 Hz, 1H), 6.56 (s, 1H), 6.80 (d, J=11.0 Hz, 1H), 7.28 (d, J=11.0 Hz, 1H), 7.36 (s, 1H)

Example 24

(−)-deacetamidocolchicine-7-ol

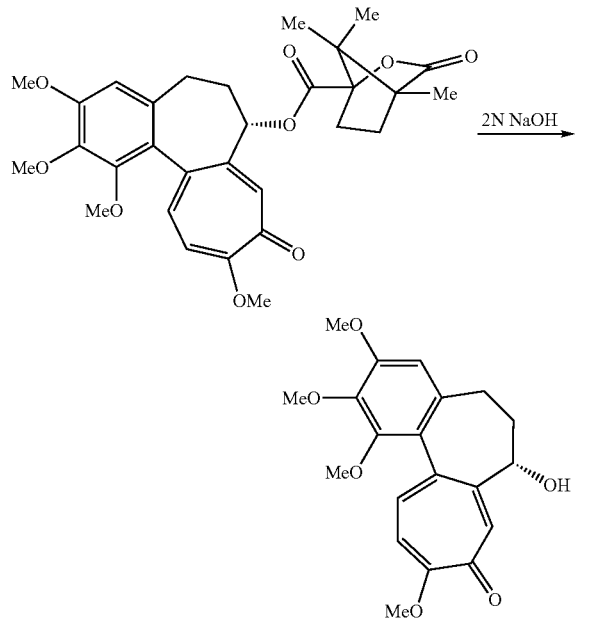

184.6 mg (0.3427 mmol) of the compound 23(1) obtained from the Example 23 was placed into a 10 ml flask, and 2.5 ml of methanol and 2.5 ml of chloroform were added thereto. The solution was cooled to −78° C., and 1.71 ml (3.4275 mmol) of 2N aqueous solution of sodium hydroxide was added into the solution. The mixture was warmed to the room temperature and stirred for 3 hours. It was extracted with chloroform for three times and washed with water, and then dried over anhydrous sodium sulfate. The solvent in the mixture was removed under reduced pressure. The resulting concentrated product was recrystallized (ethyl acetate/hexane) to obtain the title product 24 (128.8 mg, 100%).

$[\alpha]_D^{25}$: −102.55 (CDCl$_3$, c = 6.875×10$^{-3}$ g/ml)

$^1$H NMR (500 MHz, CDCl$_3$): δ 1.80–1.83 (m, 1H), 2.40–2.49 (m, 3H), 3.26 (br, 1H), 3.60 (s, 3H), 3.90 (s, 3H), 3.91 (s, 3H), 3.97 (s, 3H), 4.46–4.49 (m, 1H), 6.55 (s, 1H), 6.79 (d, J=11.0 Hz, 1H), 7.18 (d, J=11.0 Hz, 1H), 7.94 (s, 1H)

Example 25

(+)-deacetamidocolchicine-7-ol

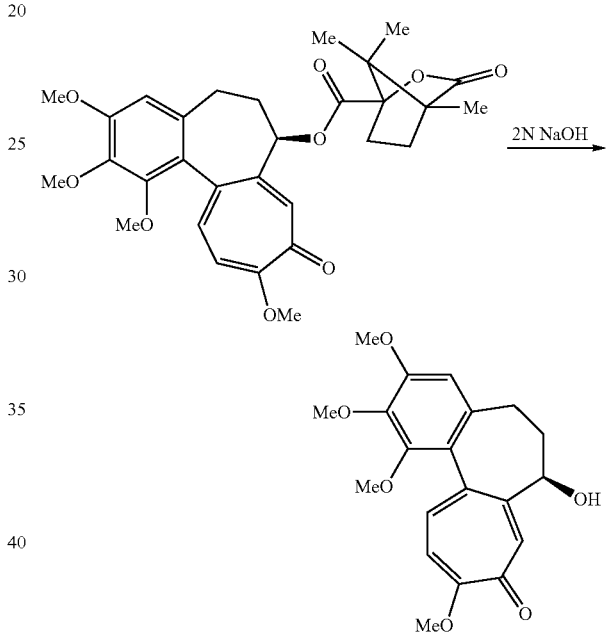

191.5 mg (0.3556 mmol) of the compound 23(2) obtained from the Example 23 was added to a 10 ml flask, and 2.5 ml of methanol and 2.5 ml of chloromethane were added thereto. The temperature was cooled down to −78° C., and 1.78 ml (3.5560 mmol) of 2N aqueous solution of sodium hydroxide was added thereto. The solution was warmed to the room temperature and stirred for 3 hours. The mixture was extracted with chloroform for three times and washed with water, and dried over anhydrous sodium sulfate and the solvent was removed by concentrating under reduced pressure. The resulting concentrated product was recrystallized (ethyl acetate/hexane) to obtain the title product 25(127.4 mg, 100%).

$[\alpha]_D^{25}$: +113.10 (CDCl$_3$, c = 7.250×10$^{-3}$ g/ml)

$^1$H NMR (500 MHz, CDCl$_3$): δ 1.80–1.83 (m, 1H), 2.40–2.49 (m, 3H), 3.26 (br, 1H), 3.60 (s, 3H), 3.90 (s, 3H), 3.91 (s, 3H), 3.97 (s, 3H), 4.46–4.49 (m, 1H), 6.55 (s, 1H), 6.79 (d, J=11.0 Hz, 1H), 7.18 (d, J=11.0 Hz, 1H), 7.94 (s, 1H)

Example 26

(−)-3-chloromethyl-benzoic acid-1,2,3,10-tetramethoxy-9-oxo-5,6,7,9-tetrahydro-bezo[a]heptarene-7-yl ester

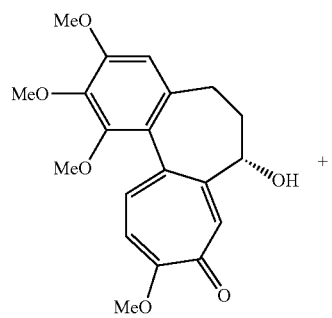

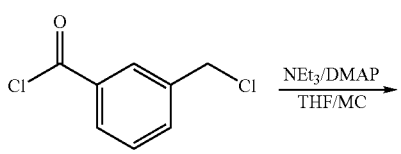

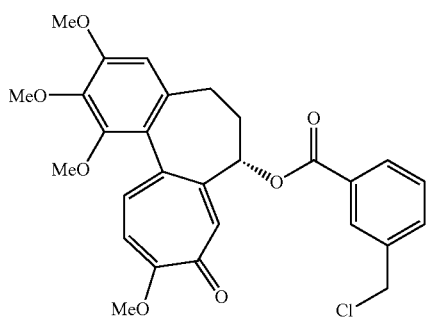

61.2 mg (0.171 mmol) of (−)-deacetamidocolchicine-7-ol was placed into a 25 ml flask, and 1 ml of chloromethane and 2 ml of THF were added thereto. To the solution, 26.7 μl (0.188 mmol) of 3-chloromethylbenzoyl chloride was added dropwise and then 71.4 μl, (0.512 mmol) of triethylamine was added. 4.2 mg (0.0342 mmol) of DMAP was added to the mixture and it was stirred at room temperature for 3 hours. The mixture was extracted with chloroform and dried over anhydrous sodium sulfate and concentrated under reduced pressure. The resulting concentrated product was purified with column chromatography (ethyl acetate:methanol=20:1) to obtain the title product 26 (60.0 mg, 68.8%).

$^1$H NMR (500 MHz, CDCl$_3$): δ 2.15–2.22 (m, 1H), 2.45–2.64 (m, 3H), 3.70 (s, 3H), 3.92 (s, 3H), 3.96 (s, 3H), 3.99 (s, 3H), 4.62 (s, 1H), 4.63 (s, 1H), 5.57 (dd, J=6.5, 5.5 Hz, 1H), 6.59 (s, 1H), 6.83 (d, J=11.0 Hz, 1H), 7.33 (d, J=11.0 Hz, 1H), 7.46 (t, J=7.5 Hz, 1H), 7.53 (s, 1H), 7.62 (d, J=7.5 Hz, 1H), 8.03 (d, J=7.5 Hz, 1H), 8.06 (s, 1H)

Example 27

(+)-3-chloromethyl-benzoic acid-1,2,3,10-tetramethoxy-9-oxo-5,6,7,9-tetrahydro-benzo[a]heptaren-7-yl ester

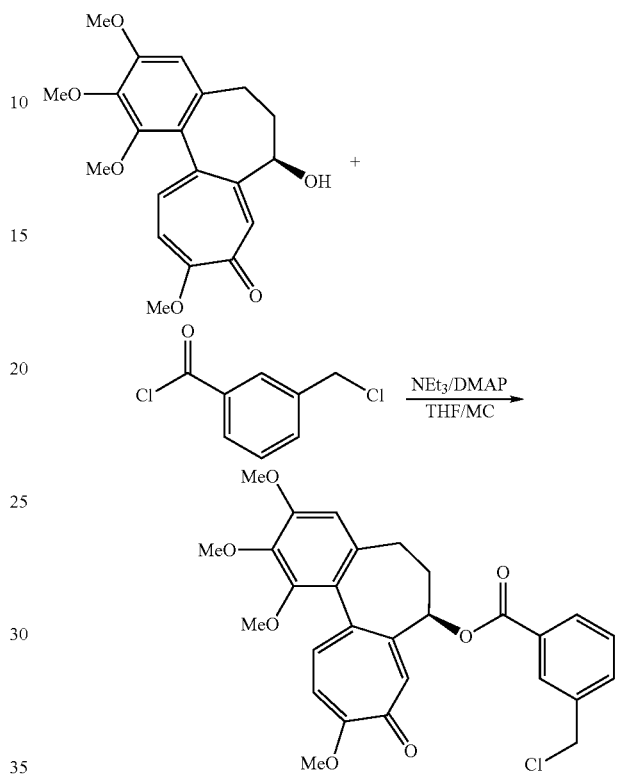

The title compound 27(58.7 mg, 67.4%) was obtained in accordance with the same method of the Example 26 except that (+)-deacetamidocolchicine-7-ol was used instead of (−)-deacetamidocolchicine-7-ol.

$^1$H NMR (500 MHz, CDCl$_3$): δ 2.15–2.22 (m, 1H), 2.45–2.64 (m, 3H), 3.70 (s, 3H), 3.92 (s, 3H), 3.96 (s, 3H), 3.99 (s, 3H), 4.62 (s, 1H), 4.63 (s, 1H), 5.57 (dd, J=6.5, 5.5 Hz, 1H), 6.59 (s, 1H), 6.83 (d, J=10.8 Hz, 1H), 7.33 (d, J=10.8 Hz, 1H), 7.46 (t, J=7.5 Hz, 1H), 7.53 (s, 1H), 7.62 (d, J=7.5 Hz, 1H), 8.03 (d, J=7.5 Hz, 1H), 8.06 (s, 1H)

Example 28

(−)-3-iodomethyl-benzoic acid-1,2,3,10-tetramethoxy-9-oxo-5,6,7,9-tetrahydro-benzo[a]heptarene-7-yl ester

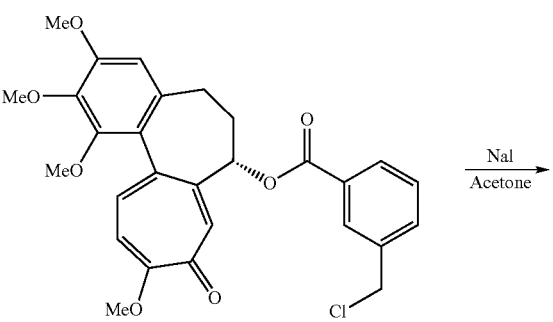

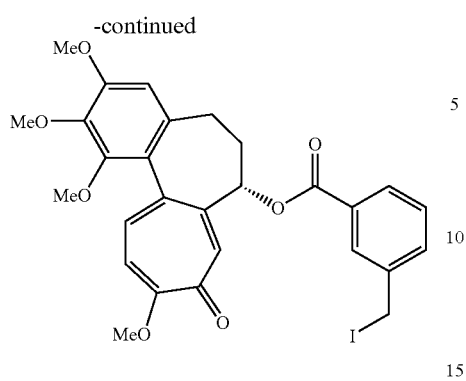

47.5 mg of the title product 28(67.1%) was prepared by the same method of the first step of the Example 4 except for using of compound 26 obtained in the Example 26.

$^1$H NMR (600 MHz, CDCl$_3$): δ 2.05–2.22 (m, 1H), 2.46–2.62 (m, 3H), 3.71 (s, 3H), 3.93 (s, 3H), 3.97 (s, 3H), 3.99 (s, 3H), 4.48 (d, J=9.9 Hz, 1H), 4.50 (d, J=9.9 Hz, 1H), 5.57 (dd, J=6.5, 4.3 Hz, 1H), 6.59 (s, 1H), 6.82 (d, J=10.8 Hz, 1H), 7.33 (d, J=10.8 Hz, 1H), 7.41 (t, J=7.8 Hz, 1H), 7.51 (s, 1H), 7.61 (d, J=7.8 Hz, 1H), 7.96 (d, J=7.8 Hz, 1H), 8.05 (s, 1H)

Example 29

(+)-3-iodomethyl-benzoic acid-1,2,3,10-tetramethoxy-9-oxo-5,6,7,9-tetrahydro-benzo[a]heptarene-7-yl ester

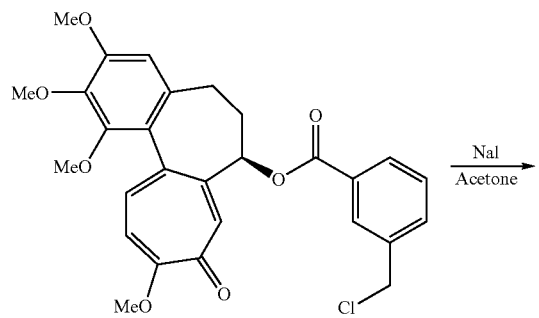

47.5 mg of the title compound 29 (68.6%) was prepared by the first step of the Example 4 except for using compound 27 obtained the Example 27.

$^1$H NMR (600 MHz, CDCl$_3$): δ 2.05–2.22 (m, 1H), 2.46–2.62 (m, 3H), 3.71 (s, 3H), 3.93 (s, 3H), 3.97 (s, 3H), 3.99 (s, 3H), 4.48 (d, J=9.9 Hz, 1H), 4.50 (d, J=9.9 Hz, 1H), 5.57 (dd, J=6.5, 4.3 Hz, 1H), 6.59 (s, 1H), 6.82 (d, J=10.8 Hz, 1H), 7.33 (d, J=10.8 Hz, 1H), 7.41 (t, J=7.8 Hz, 1H), 7.51 (s, 1H), 7.61 (d, J=7.8 Hz, 1H), 7.96 (d, J=7.8 Hz, 1H), 8.05 (s, 1H)

Example 30

(−)-3-nitrooxymethyl-benzoic acid-1,2,3,10-tetramethoxy-9-oxo-5,6,7,9-tetrahydro-benzo[a]heptaren-7-yl ester

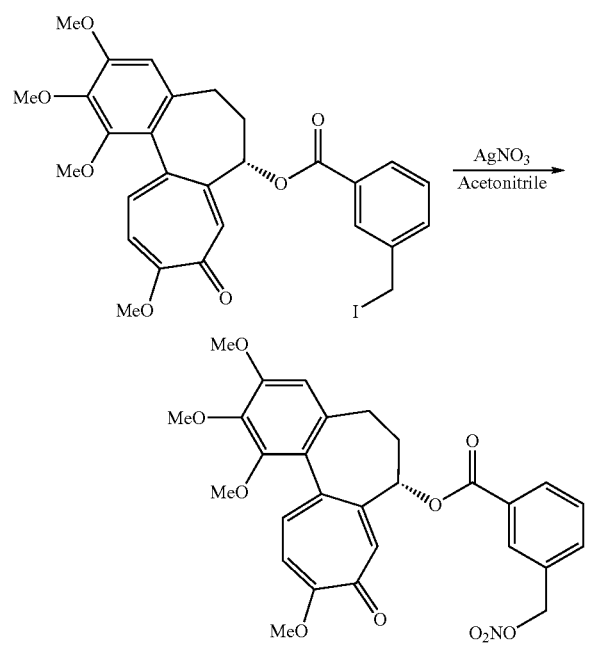

34.4 mg of the title compound 30 (81.2%) was prepared by the second step of the Example 4 except for using compound 28 obtained the Example 28.

$^1$H NMR (500 MHz, CDCl$_3$): δ 2.10–2.22 (m, 1H), 2.46–2.62 (m, 3H), 3.70 (s, 3H), 3.92 (s, 3H), 3.96 (s, 3H), 3.99 (s, 3H), 5.48 (s, 2H), 5.57 (dd, J=6.5, 4.5 Hz, 1H), 6.59 (s, 1H), 6.82 (d, J=10.8 Hz, 1H), 7.32 (d, J=10.8 Hz, 1H), 7.50 (s, 1H), 7.51 (t, J=7.8 Hz, 1H), 7.63 (d, J=7.8 Hz, 1H), 8.09 (s, 1H), 8.10 (d, J=7.8 Hz, 1H)

Example 31

(+)-3-nitrooxymethyl-benzoic acid-1,2,3,10-tetramethoxy-9-oxo-5,6,7,9-tetrahydro-benzo[a]heptarene-7-yl ester

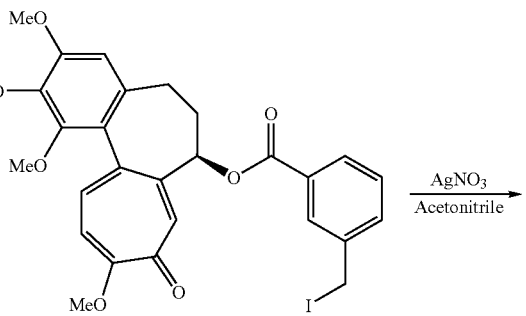

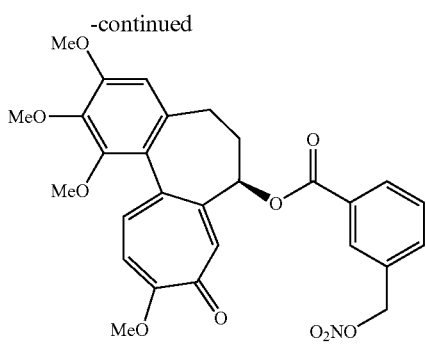

32.5 mg of the title compound 31 (76.7%) was prepared by the second step of the Example 4 except for using compound 29 obtained the Example 29.

$^1$H NMR (500 MHz, CDCl$_3$): δ 2.10–2.22 (m, 1H), 2.46–2.62 (m, 3H), 3.70 (s, 3H), 3.92 (s, 3H), 3.96 (s, 3H), 3.99 (s, 3H), 5.48 (s, 2H), 5.57 (dd, J=6.5, 4.5 Hz, 1H), 6.59 (s, 1H), 6.82 (d, J=10.8 Hz, 1H), 7.32 (d, J=10.8 Hz, 1H), 7.50 (s, 1H), 7.51 (t, J=7.8 Hz, 1H), 7.63 (d, J=7.8 Hz, 1H), 8.09 (s, 1H), 8.10 (d, J=7.8 Hz, 1H)

Table 1 shows the list of the compounds synthesized in accordance with the method of the present invention in addition to the compounds of the above Examples

TABLE 1A

| Compounds | $^1$H NMR (500 MHz): δ |
|---|---|
| (structure) | 1.85–1.90(m, 1H), 2.00(s, 3H), 2.23–2.42(m, 4H), 2.50–2.56(m, 1H), 2.82–2.88(m, 2H), 3.68(s, 3H), 3.74(t, J = 6.3 Hz, 2H), 3.96(s, 3H), 4.03(s, 3H), 4.62–4.66(m, 1H), 6.71(s, 1H), 6.88(d, J = 10.9 Hz, 1H), 7.34(d, J = 10.9 Hz, 1H), 7.38(d, J = 6.3 Hz, 1H), 7.54(s, 1H) |
| (structure) | 1.92–1.98(m, 1H), 2.00(s, 3H), 2.31–2.44(m, 2H), 2.55–2.59(m, 1H), 3.69(s, 3H), 3.94(s, 3H), 4.03(s, 3H), 4.64–4.69(m, 1H), 4.67(s, 2H), 6.83(s, 1H), 6.91(d, J = 10.9 Hz, 1H), 7.38(d, J = 10.9 Hz, 1H), 7.57(d, J = 8.2 Hz, 2H), 7.61(s, 1H), 7.94(d, J = 6.2 Hz, 1H), 8.23(d, J = 8.2 Hz, 2H) |
| (structure) | 1.92–2.00(m, 1H), 1.95(S, 3H), 2.31–2.44(m, 2H), 2.57–2.59(m, 1H), 3.70(s, 3H), 3.95(s, 3H), 4.04(s, 3H), 4.65–4.70(m, 1H), 4.69(s, 2H), 6.83(s, 1H), 6.92(d, J = 10.9 Hz, 1H), 7.39(d, J = 10.9 Hz, 1H), 7.56(t, J = 7.6 Hz, 1H), 7.64(s, 1H), 7.71(d, J = 7.6 Hz, 1H), 8.03(d, J = 6.2 Hz, 1H), 8.19(d, J = 7.6 Hz, 1H), 8.26(s, 1H) |

TABLE 1A-continued

| Compounds | $^1$H NMR (500 MHz): δ |
|---|---|
| *(structure)* | 1.91–1.96(m, 1H), 1.97(s, 3H), 2.20–2.26(m, 2H), 2.29–2.40(m, 2H), 2.52–2.56(m, 1H), 2.77–2.80(m, 2H), 3.66(s, 3H), 3.93(s, 3H), 4.03(s, 3H), 4.61–4.65(m, 1H), 4.64(t, J = 6.5 Hz, 2H), 6.70(s, 1H), 6.90(d, J = 10.9 Hz, 1H), 7.35(d, J = 10.9 Hz, 1H), 7.60(s, 1H), 8.05(d, J = 6.2 Hz, 1H) |
| *(structure)* | 1.90–1.95(m, 1H), 1.99(s, 3H), 2.29–2.43(m, 2H), 2.55–2.58(m, 1H), 3.69(s, 3H), 3.93(s, 3H), 4.03(s, 3H), 4.64–4.68(m, 1H), 4.82(s, 2H), 6.83(s, 1H), 6.91(d, J = 10.9 Hz, 1H), 7.38(d, J = 10.9 Hz, 1H), 7.53(d, J = 8.2 Hz, 2H), 7.60(s, 1H), 7.91(d, J = 6.2 Hz, 1H), 8.22(d, J = 8.2 Hz, 2H) |
| *(structure)* | 1.89–1.96(m, 1H), 1.99(s, 3H), 2.29–2.43(m, 2H), 2.54–2.58(m, 1H), 3.69(s, 3H), 3.93(s, 3H), 4.03(s, 3H), 4.63–4.68(m, 1H), 4.81(s, 2H), 6.82(s, 1H), 6.91(d, J = 10.9 Hz, 1H), 7.38(d, J = 10.9 Hz, 1H), 7.53(t, J = 7.6 Hz, 1H), 7.59 (s, 1H), 7.68(d, J = 7.6 Hz, 1H), 7.84(d, J = 6.2 Hz, 1H), 8.15(d, J = 7.6 Hz, 1H), 8.23(s, 1H) |
| *(structure)* | 1.99–2.06(m, 2H), 2.08–2.15(m, 1H), 2.22–2.28(m, 1H), 2.42(s, 3H), 2.43–2.51(m, 3H), 2.61–2.65(m, 1H), 3.28(s, 3H), 3.56(t, J = 6.0 Hz, 2H), 3.70(s, 3H), 3.90(s, 3H), 3.94(s, 3H), 4.98(q, J = 6.2 Hz, 1H), 6.53(s, 1H), 6.90(s, 1H), 7.02(d, J = 10.3 Hz, 1H), 7.27(d, J = 10.3 Hz, 1H) |

TABLE 1A-continued

| Compounds | $^1$H NMR (500 MHz): δ |
|---|---|
| (structure) | 2.25–2.36(m, 2H), 2.44(s, 3H), 2.49–2.56(m, 1H), 2.66–2.69(m, 1H), 3.23 (s, 3H), 3.72(s, 3H), 3.91(s, 3H), 3.94(s, 3H), 5.06(br, 1H), 5.42(s, 2H), 6.57(s, 1H), 7.05(d, J = 10.3 Hz, 1H), 7.08(s, 1H), 7.31–7.40(m, 5H) |
| (structure) | 2.25–2.37(m, 2H), 2.44(s, 3H), 2.48–2.56(m, 1H), 2.66–2.68(m, 1H), 3.24 (s, 3H), 3.72(s, 3H), 3.91(s, 3H), 3.94(s, 3H), 5.05(br, 1H), 5.40(s, 2H), 6.57(s, 1H), 7.06(d, J = 10.3 Hz, 1H), 7.09(s, 1H), 7.31–7.42(m, 5H) |
| (structure) | 2.15–2.20(m, 1H), 2.43(s, 3H), 2.44–2.64(m, 3H), 3.70(s, 3H), 3.92(s, 3H), 3.96(s, 3H), 4.62(s, 2H), 5.57(dd, J = 7, 7.5 Hz, 1H), 6.59(s, 1H), 7.05(d, J = 10.0 Hz, 1H), 7.30(d, J = 10.0 Hz, 1H), 7.33(s, 1H), 7.46(dd, J = 8.0, 8.0 Hz, 1H), 7.62(d, J = 8.0 Hz, 1H), 8.03(d, J = 8.0 Hz, 1H), 8.06(s, 1H) |
| (structure) | 2.15–2.20(m, 1H), 2.43(s, 3H), 2.44–2.64(m, 3H), 3.70(s, 3H), 3.92(s, 3H), 3.96(s, 3H), 4.62(s, 2H), 5.57(dd, J = 7, 7.5 Hz, 1H), 6.59(s, 1H), 7.05(d, J = 10.0 Hz, 1H), 7.30(d, J = 10.0 Hz, 1H), 7.33(s, 1H), 7.46(dd, J = 8.0, 8.0 Hz, 1H), 7.62(d, J = 8.0 Hz, 1H), 8.03(d, J = 8.0 Hz, 1H), 8.06(s, 1H) |
| (structure) | 2.15–2.20(m, 1H), 2.43(s, 3H), 2.44–2.64(m, 3H), 3.70(s, 3H), 3.92(s, 3H), 3.96(s, 3H), 5.48(s, 2H), 5.57(dd, J = 7, 7.5 Hz, 1H), 6.59(s, 1H), 7.05(d, J = 10.0 Hz, 1H), 7.30–7.33(m, 2H), 7.46(dd, J = 8.0, 8.0 Hz, 1H), 7.63(d, J = 8.0 Hz, 1H), 8.08–8.10(m, 2H) |

TABLE 1A-continued
| Compounds | ¹H NMR (500 MHz): δ |
|---|---|
| 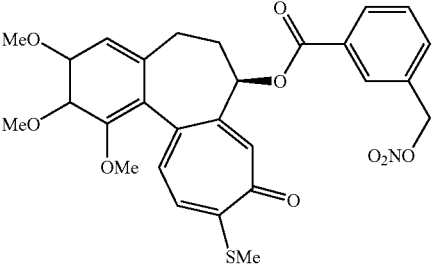 | 2.15–2.20(m, 1H), 2.43(s, 3H), 2.44–2.64(m, 3H), 3.70(s, 3H), 3.92(s, 3H), 3.96(s, 3H), 5.48(s, 2H), 5.57(dd, J = 7, 7.5 Hz, 1H), 6.59(s, 1H), 7.05(d, J = 10.0 Hz, 1H), 7.30–7.33(m, 2H), 7.46(dd, J = 8.0, 8.0 Hz, 1H), 7.63(d, J = 8.0 Hz, 1H), 8.08–8.10(m, 2H) |
| 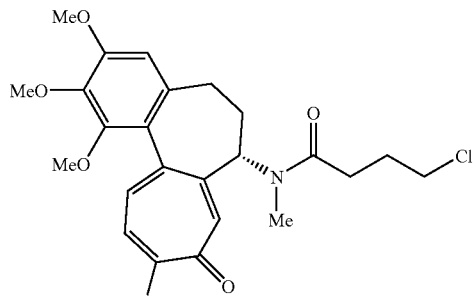 | 2.01–2.40(m, 4H), 2.43–2.64(m, 4H), 3.28(s, 3H), 3.56(t, J = 6.0 Hz, 2H), 3.69(s, 3H), 3.90(s, 3H), 3.94(s, 3H), 3.98(s, 3H), 4.94–5.01(m, 1H), 6.53(s, 1H), 6.80(d, J = 10.6 Hz, 1H), 7.09(s, 1H), 7.28(d, J = 10.6 Hz, 1H) |
| 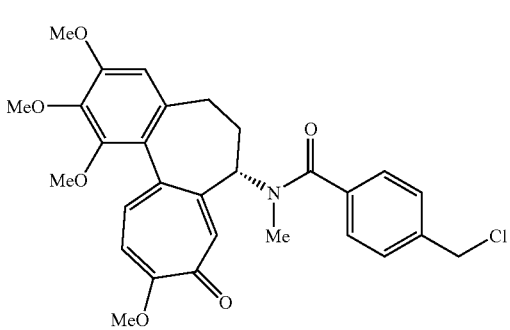 | 2.20–2.31(m, 2H), 2.46–2.53(m, 1H), 2.60–2.65(m, 1H), 3.22(s, 3H), 3.70(s, 3H), 3.84(s, 3H), 3.86(s, 3H), 3.97(s, 3H), 4.55(s, 2H), 5.01–5.03(m, 1H), 6.54(s, 1H), 6.79(d, J = 10.6 Hz, 1H), 7.25–7.45(m, 6H) |
| 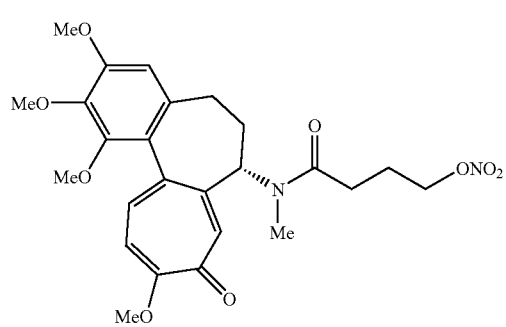 | 1.96–2.30(m, 4H), 2.40–2.67(m, 4H), 3.26(s, 3H), 3.69(s, 3H), 3.90(s, 3H), 3.94(s, 3H), 3.98(s, 3H), 4.45(t, J = 6.0 Hz, 2H), 5.01–5.04(m, 1H), 6.53(s, 1H), 6.81(d, J = 10.6 Hz, 1H), 7.07(s, 1H), 7.28(d, J = 10.6 Hz, 1H) |
| 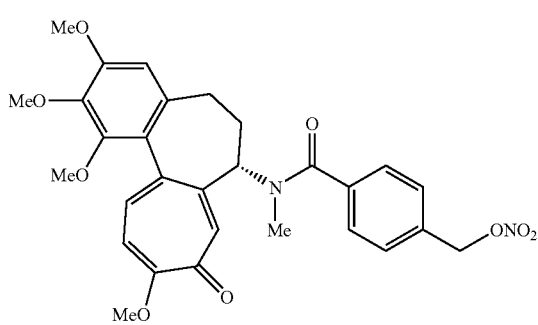 | 2.17–2.39(m, 2H), 2.51–2.69(m, 2H), 3.24(s, 3H), 3.71(s, 3H), 3.91(s, 3H), 3.94(s, 3H), 4.00(s, 3H), 5.00–5.10(m, 1H), 5.42(s, 2H), 6.57(s, 1H), 6.82(d, J = 10.6 Hz, 1H), 7.28–7.39(m, 6H) |

TABLE 1A-continued

| Compounds | $^1$H NMR (500 MHz): δ |
|---|---|
| | 1.87–1.96(m, 1H), 2.03(s, 3H), 2.05–2.12(m, 2H), 2.20–2.51(m, 2H), 2.49(t, J = 7.0 Hz, 2H), 2.81–2.83(m, 1H), 3.65(s, 3H), 3.96(s, 3H), 3.97(s, 3H), 4.02(s, 3H), 4.54(t, J = 7.0 Hz, 2H), 4.63–4.65(m, 1H), 5.17(d, J = 12.0 Hz, 1H), 5.29(d, J = 12.0 Hz, 1H), 6.88(d, J = 11.0 Hz, 1H), 7.28(d, J = 11.0 Hz, 1H), 7.56(s, 1H), 7.87(d, J = 6.5 Hz, 1H) |
| | 1.82–1.88(m, 1H), 2.00–2.26(m, 4H), 2.36–2.56(m, 2H), 2.45(s, 3H), 2.91–2.94(m, 1H), 3.42(s, 3H), 3.54(t, J = 6.2 Hz, 2H), 3.64(s, 3H), 3.95(s, 3H), 3.97(s, 3H), 4.46(d, J = 10.3 Hz, 1H), 4.50(d, J = 10.3 Hz, 1H), 4.61–4.66(m, 1H), 7.08(d, J = 10.6 Hz, 1H), 7.25(d, J = 10.6 Hz, 1H), 7.41(d, J = 7.3 Hz, 1H), 7.43(s, 1H) |
| | 2.05–2.34(m, 3H), 2.45(s, 3H), 2.96–3.00(m, 1H), 3.42(s, 3H), 3.72(s, 3H), 3.96(s, 3H), 3.99(s, 3H), 4.45(s, 2H), 4.47(d, J = 10.3 Hz, 1H), 4.54(d, J = 10.3 Hz, 1H), 4.85–4.93(m, 1H), 7.09(d, J = 10.6 Hz, 1H), 7.22(d, J = 8.3 Hz, 2H), 7.29(d, J = 10.3 Hz, 1H), 7.59(s, 1H), 7.84(d, J = 8.3 Hz, 2H), 8.34(d, J = 7.3 Hz, 1H) |
| | 1.78–1.85(m, 1H), 1.98–2.05(m, 2H), 2.14–2.42(m, 4H), 2.45(s, 3H), 2.91–2.94(m, 1H), 3.42(s, 3H), 3.64(s, 3H), 3.95(s, 3H), 3.97(s, 3H), 4.42–4.52(m, 4H), 4.63–4.67(m, 1H), 7.09(d, J = 10.6 Hz, 1H), 7.26(d, J = 10.6 Hz, 1H), 7.47(s, 1H), 7.77(d, J = 7.3 Hz, 1H) |

TABLE 1A-continued

| Compounds | $^1$H NMR (500 MHz): δ |
|---|---|
| *[structure: colchicine analog with MeO, MeO, MeO on aromatic ring, MeS on tropone, and CH2OMe group; amide linked to benzene with CH2ONO2]* | 2.14–2.34(m, 3H), 2.45(s, 3H), 2.96–3.01(m, 1H), 3.42(s, 3H), 3.72(s, 3H), 3.96(s, 3H), 3.99(s, 3H), 4.46(d, J = 10.3 Hz, 1H), 4.53(d, J = 10.3 Hz, 1H), 4.88–4.94(m, 1H), 5.30(s, 2H), 7.11(d, J = 10.6 Hz, 1H), 7.21(d, J = 8.3 Hz, 2H), 7.31(d, J = 10.3 Hz, 1H), 7.62(s, 1H), 7.88(d, J = 8.3 Hz, 2H), 8.51(d, J = 7.3 Hz, 1H) |
| *[structure: colchicine analog with MeO, MeO, MeO; NHAc at C7; tropone NH linked to benzamide with CH2Cl meta]* | 1.82(m, 1H), 2.03(s, 3H), 2.25(m, 1H), 2.40(m, 1H), 2.54(m, 1H), 3.66(s, 3H), 3.91(s, 3H), 3.94(s, 3H), 4.68(s, 2H), 4.71(m, 1H), 6.54(s, 1H), 6.73(d, J = 7.0 Hz, 1H), 7.51~7.65(m, 4H), 7.94(d, J = 8.0 Hz, 1H), 8.01(s, 1H), 9.20(d, J = 11.0 Hz, 1H), 10.32(s, 1H) |
| *[structure: general formula (I) with R4—O, R5, R3—O, H3CO, R1, R2, X substituents on colchicinoid scaffold]* (I) | 1.84(m, 1H), 2.03(s, 3H), 2.28(m, 1H), 2.42(m, 1H), 2.54(m, 1H), 3.67(s, 3H), 3.91(s, 3H), 3.92(s, 3H), 4.69(m, 1H)), 5.53(s, 2H), 6.39(d, J = 7.0 Hz, 1H), 6.54(s, 1H), 7.51~7.65(m, 4H), 8.01(d, J = 9.5 Hz, 1H), 8.03 (s, 1H), 9.18(d, J = 11.0 Hz, 1H), 10.32(s, 1H) |
| *[structure: colchicine analog with MeO, MeO, MeO; NHAc at C7; tropone NH linked to 4-chlorobutanoyl]* | 1.80(m, 1H), 2.02(s, 3H), 2.22(t, J = 6.0, 6.5 Hz, 2H), 2.40(m, 1H), 2.48 (m, 1H), 2.72(t, J = 7.0 Hz, 2H), 3.62(s, 3H), 3.67(t, J = 6.0 Hz, 2H), 3.90(s, 3H), 3.94(s, 3H) 4.64(m, 1H), 6.18(d, J = 7.0 Hz, 1H), 6.52(s, 1H), 7.43(d, J = 10.5 Hz, 1H), 7.49(s, 1H), 8.99(d, J = 11.0 Hz, 1H), 9.41(s, 1H) |

TABLE 1A-continued

| Compounds | ¹H NMR (500 MHz): δ |
|---|---|
| (structure: trimethoxy-dimethylamino tropone colchicine core with N-H benzamide bearing para-CH₂Cl) | 1.98(m, 1H), 2.25(m, 1H), 2.47(m, 1H), 2.49(m, 1H), 3.15(s, 1H), 3.71(s, 3H), 3.88(s, 3H), 3.95(s, 3H), 4.55(s, 2H), 4.81(m, 1H), 6.51(s, 1H), 6.55(d, J = 11.5 Hz, 1H), 7.22(s, 1H), 7.28~7.37(dd, J = 8.5, 11.5 Hz, 4H), 7.61(d, J = 7.0 Hz, 1H), 7.87(d, J = 10.5 Hz, 1H) |
| (structure: colchicine core with N-H benzamide bearing para-CH₂ONO₂) | 1.98(m, 1H), 2.29(m, 1H), 2.50(m, 1H), 2.51(m, 1H), 3.14(s, 6H), 3.71(s, 3H), 3.89(s, 3H), 3.95(s, 3H), 4.81(m, 1H), 5.42(s, 2H), 6.52(s, 1H), 6.55(d, J = 11.5 Hz, 1H), 7.17(s, 1H), 7.27~7.40(dd, J = 8.5, 11.5 Hz, 4H), 7.87(d, J = 8.5 Hz, 1H) |
| (structure: colchicine core with N-H benzamide bearing meta-CH₂Cl) | 1.98(m, 1H), 2.03(m, 1H), 2.48(m, 1H), 2.53(m, 1H), 3.14(s, 6H), 3.70(s, 3H), 3.90(s, 3H), 3.95(s, 3H), 4.56(s, 2H), 4.83(m, 1H), 6.55(s, 1H), 6.56(d, J = 11.2 Hz, 1H), 6.93(d, J = 7.5 Hz, 1H), 7.14~7.52(m, 4H), 7.73(d, J = 7.7 Hz, 1H), 7.79(s, 1H) |
| (structure: colchicine core with N-H benzamide bearing meta-CH₂ONO₂) | 2.20(m, 1H), 2.48(m, 1H), 2.54(m, 2H), 3.15(s, 6H), 3.72(s, 3H), 3.90(s, 3H), 3.96(s, 3H), 4.85(m, 1H), 5.32(d, J = 5.3 Hz, 2H), 6.55(s, 1H), 6.58(d, J = 11.3 Hz, 1H), 7.28~7.54(m, 4H), 7.76(d, J = 7.8 Hz, 1H), 7.80(s, 1H) |

TABLE 1A-continued

| Compounds | ¹H NMR (500 MHz): δ |
|---|---|
| [structure: colchicine derivative with MeO, MeO, MeO, Me₂N, and NHC(O)CH₂CH₂CH₂Cl side chain] | 1.80(m, 1H), 2.04(m, 1H), 2.07(t, 2H, J = 7.0 Hz), 2.20(m, 1H), 2.43(m, 1H), 2.49(t, J = 7.0 Hz, 2H), 3.17(s, 6H), 3.56(t, J = 6.0, 6.5 Hz, 2H), 3.64(s, 3H), 3.87(s, 3H), 3.93(s, 3H), 4.60(m, 1H), 6.49(s, 1H), 6.55(d, J = 11.5 Hz, 1H), 7.16(s, 1H), 7.21(d, J = 10.5 Hz, 1H), 7.27(d, J = 11.5 Hz, 1H) |
| [structure: colchicine derivative with MeO, MeO, MeO, Me₂N, and NHC(O)CH₂CH₂CH₂ONO₂ side chain] | 2.01(m, 1H), 2.04(t, 2H, J = 6.5, 6.5 Hz), 2.18(m, 1H), 2.40(m, 1H), 2.46(m, 2H), 2.48(m, 1H), 3.17(s, 6H), 3.64(s, 3H), 3.88(s, 3H), 3.93(s, 3H), 4.45(t, 2H, J = 6.0, 6.5 Hz), 4.58(m, 1H), 6.48(s, 1H), 6.55(d, 1H, J = 11.5 Hz), 7.11(s, 1H), 7.27(d, 1H, J = 11.5 Hz), 7.44(d, 1H, J = 7.0 Hz) |

Example A

Anticancer Effect Test

To ascertain the anticancer effects of colchicine derivatives of the formula (I) according to the present invention, the following tests were carried out by sulforhodamine-B (SRB) cytotoxicity assay. For comparison of anticancer effects, conventional colchicine and taxol as an anticancer drug were used as control groups.

Human tumor cells, including MCF-7 (human breast adenomatous tumor), MCF-7/DOX (adriamycin resistant cell strain), MRS-SA (human uterine sarcoma), MES-SA/DX5 (adriamycin resistant cell strain), A 549 (human non-small cell lung), SKOV-3 (human ovarian), SKMEL-2 (human melanoma), XF-498 (human CNS), HCT-15 (human colon) were incubated at 37° C. in the presence of 5% $CO_2$ using a DMEM culture medium. The respective cells were seeded into each well of 96-well plates at a concentration of $2 \times 10^3 \sim 5 \times 10^3$ cells/well. After culturing for 24 hours, colchicine dissolved in dimethylsulfoxide (DMSO), a compound 6, a compound 12 and taxol were diluted, and further cultured for 72 hours. Each cell line of the resultant plates was fixed with trichloroacetic acid (TCA), stained with 0.4% SRB solution and rinsed with 1% acetic acid. Thereafter, the dye was dissolved in 10 mM Tris base to measure the optical density (OD) at 520 nm. The measurement results are listed in Tables 2 and 3.

TABLE 2

| | ED50 (nM) | | | |
|---|---|---|---|---|
| Materials | MCF7 | MCF-7/DOX | MES-SA | MES-SA/DX5 |
| Colchicine | 4 | 183 | 16 | 961 |
| Compound 6 | 0.02 | 205 | 0.2 | 773 |
| Compound 12 | 0.02 | 28 | 0.01 | 115 |
| Taxol | 0.04 | 943 | 0.02 | 1147 |

TABLE 3

| | ED50 (nM) | | | | |
|---|---|---|---|---|---|
| Material | A549 | SK-OV-3 | SK-MEL-2 | XF498 | HCT15 |
| Colchicine | 9 | 8 | 3 | 4 | 3 |
| Compound 6 | 0.1 | 0.2 | 0.1 | 0.1 | 0.1 |
| Compound 12 | 0.1 | 0.3 | 0.1 | 0.2 | 0.1 |
| Taxol | 0.3 | 1.2 | 0.1 | 1.7 | 0.1 |

When ED50 values of the compounds 6 and 12 were investigated for each cell line, the colchicine derivative of the present invention exhibited a higher anticancer effect even at a low concentration of 0.02 to 773 nM than the conventional colchicine and taxol as shown in Tables 2 and 3.

Example B

Mixed Lymphocyte Reaction (MLR) Tests

MLR tests were carried out to determine the immunosuppressive effect of an immunosuppressive candidate material. When a responding cell (BALB/c mouse spleen cell) and a stimulating cell (DBA/2 mouse spleen cell) were cultured separately, the cells grew little. On the contrary, when the cells were simultaneously cultured, the cells were proliferated due to induction of an antigen-antibody reaction. The proliferated cells were treated with the immunosuppressive candidate material for measurement of the proliferation inhibitory extent.

Responding cells (BALB/c mouse spleen cells) and stimulating cells (DBA/2 mouse spleen cells) were respectively seeded into each well of 96-well plates at a concentration of $2 \times 10^5$ cells/well for simultaneous culturing, and cyclosporin A (positive control group), colchicines, and colchicine derivatives of the present invention (compounds 6, 9, 10, 11 and 12) were treated. After culturing for 72 hours at a $CO_2$ incubator, a 20 µl MTS solution was added to each well, followed by further culturing for 2 to 4 hours and measuring OD at 490 rum by using ELISA. The results were shown in FIG. 1.

As shown in FIG. 1, it can be found that the colchicine derivatives according to the present invention, that is, the compounds 6, 9, 10, 11 and 12, suppressed growth of cells even at concentrations as low as 100 to 1000 nm and had a good immunosuppressive effect.

Example C

Immunosuppressive Effect Test Using BALB/c Mouse Spleen Cells

This test was carried out to determine the immunosuppressive effect of an immunosuppressive candidate material by checking anti-proliferation of T cells and B cells. To identify the proliferation inhibitory extent, responding cells (BALB/c mouse spleen cells) were treated with an immunosuppressive candidate material, lipopolysaccharide (LPS) as a B cell activator and concanvalin A (ConA) as a T cell activator. It is known that the responding cells treated with LPS induce proliferation of B cells and those treated with ConA induce proliferation of T cells.

Responding cells (BALB/c mouse spleen cells) were seeded into each well of 96-well plates at a concentration of $2 \times 10^5$ cells/well. Then, 20 µg/ml lipopolysaccharide, cyclosporin A (positive control group), and inventive colchicine derivatives (compounds 6, 10 and 12) were simultaneously treated, and 2 µg/ml of ConA, cyclosporin A (positive control sample), and inventive colchicine derivatives (compounds 6, 10 and 12) were simultaneously treated. After culturing for 72 hours at a $CO_2$ incubator, a 20 µl MTS solution was added to each well, followed by further culturing for 2 to 4 hours and measuring OD at 490 nm using ELISA. The measurement results are shown in FIGS. 2 and 3.

Figure 2:
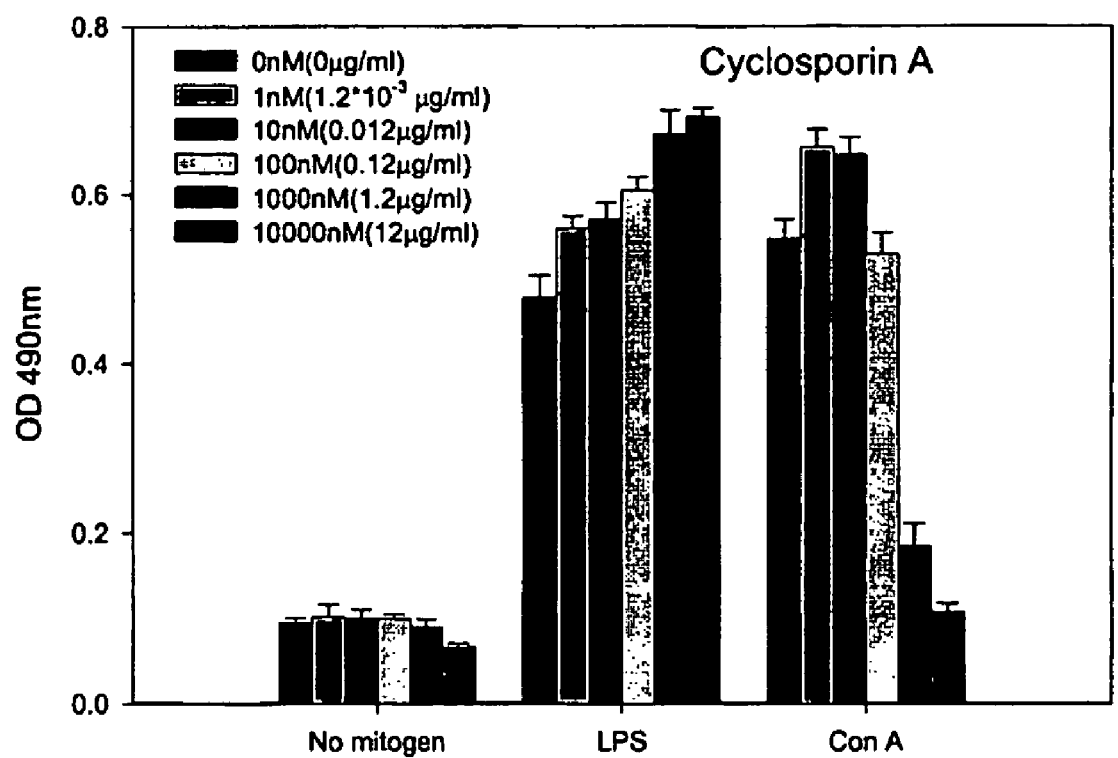
FIG. 2 is a graph showing the immonosuppressive effect of cyclosphorine A as a positive control sample in an immunosuppressive effect test using a BALB/c mouse spleen.
Figure 3:
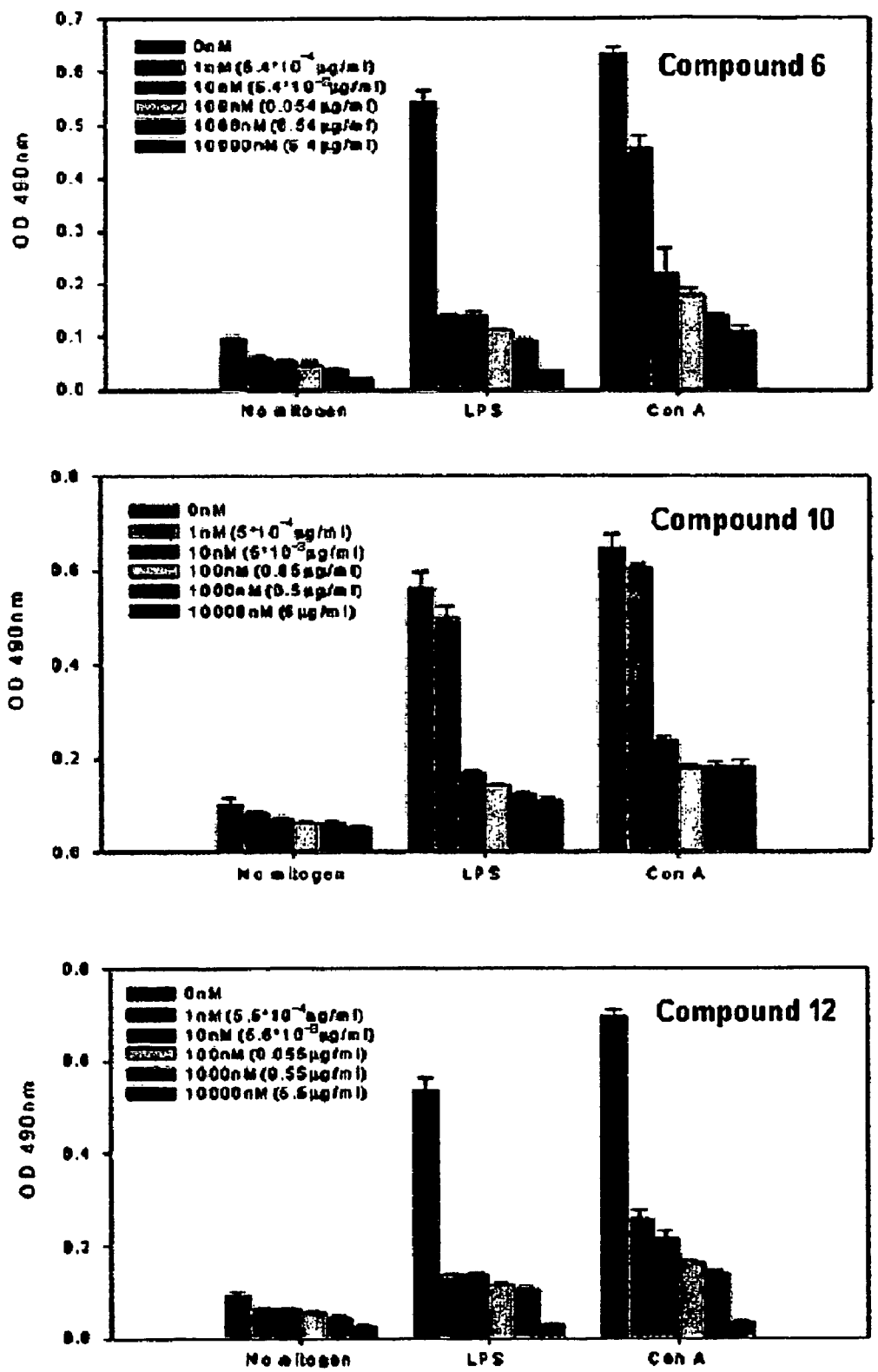
FIG. 3 is a graph showing the immonosuppressive effect of a colchicine derivative according to the present invention in an immunosuppressive effect test using a BALB/c mouse spleen.

As shown in FIGS. 2 and 3, the colchicine derivatives according to the present invention suppressed proliferation of the B and T cells induced by LPS and ConA, respectively, in a concentration-dependent manner. The immunosuppressive effect of the colchicine derivatives according to the present invention was superior to that of cyclosporin A, a conventional immunosuppressive agent. In particular, the compounds 6 and 12 exhibited a remarkable anti-proliferous effect on B and T cells (FIG. 3).

Example D

Toxicity Assay

The colchicine derivatives according to the present invention were administered to ICR mice of 4–5 weeks old, weighing 18 to 20 g, for acute (intravenous administration) toxicity assay and oral administration toxicity assay, as demonstrated in Tables 5 and 7. The same assays were carried out using colchicine as a control group (see Tables 4 and 6).

TABLE 4

Acute toxicity of colchicine intravenously administered to mice

| Group | Number of Mouse | Dosage (mg/kg) | 1 | 2 | 3 | 4 | 5 | 6 | 7 | Total |
|---|---|---|---|---|---|---|---|---|---|---|
| T1 | 5 | 2 | — | 3 | 1 | — | — | 1 | — | 5/5 |
| T2 | 5 | 5 | 1 | 4 | | | | | | 5/5 |
| T3 | 5 | 10 | 4 | 1 | | | | | | 5/5 |

Days for the test (death)

TABLE 5

Acute toxicity of compound 6 intravenously administered to mice

| Group | Number of Mouse | Dosage (mg/kg) | 1 | 2 | 3 | 4 | 5 | 6 | 7 | Total |
|---|---|---|---|---|---|---|---|---|---|---|
| T1 | 5 | 5 | — | — | — | — | — | — | — | 0/5 |
| T2 | 5 | 10 | — | — | — | — | — | — | — | 0/5 |
| T3 | 5 | 25 | — | — | — | — | — | — | — | 0/2 |
| T4 | 3 | 50 | 3 | | | | | | | 3/3 |

Days for the test (death)

TABLE 6

Toxicity of colchicine orally administered to mice

| Group | Number of Mouse | Dosage (mg/kg) | 1 | 2 | 3 | 4 | 5 | 6 | 7 | Total |
|---|---|---|---|---|---|---|---|---|---|---|
| T1 | 5 | 5 | — | — | — | — | — | — | — | 0/5 |
| T2 | 5 | 10 | — | — | — | — | — | — | — | 0/5 |
| T3 | 5 | 25 | — | — | 3 | 1 | — | — | — | 4/5 |
| T4 | 3 | 50 | — | 3 | — | 1 | 1 | — | — | 5/5 |

Days for the Test (death)

TABLE 7

Toxicity of compound 6 orally administered to mice

| Group | Number of Mouse | Dosage (mg/kg) | 1 | 2 | 3 | 4 | 5 | 6 | 7 | Total |
|---|---|---|---|---|---|---|---|---|---|---|
| T1 | 5 | 2 | — | — | — | — | — | — | — | 0/5 |
| T2 | 5 | 5 | — | — | — | 1 | — | — | — | 1/5 |
| T3 | 5 | 10 | — | 1 | 1 | — | — | — | — | 2/5 |

Days for the Test (death)

Example E

Reverse Mutation Assay by Using Bacteria

This assay is carried out to test mutagenicity of chemical substances using histidine auxotrophic strains that are one of *Salmonella Typhimurium* mutants. In the assay, artificially induced mutants (histidine auxotrophic mutants) are cultured in a histidine-free culture medium. When various mutagens are added to the culture medium, only revertants generated by reverse mutation survive. Thus generated colonies and spontaneously induced revertants are compared for detection of mutation.

Ames test was carried out using WP2 uvrA strains (tryptophan auxotrophic strains) of TA100, TA1535, TA98, TA1537 and *Escherichia coli*. Mutagens used as positive control samples were 0.5 µg/plate of sodium azide, 0.5 µg/plate of 4NQO (4-nitroquinolin-1-oxide), 50 µg/plate of 9-AA (9-aminoacridine). Colchicine and colchicine derivative (Compound 6) according to the present invention were treated at amounts of 0, 317.5, 625, 1250, 2500, and 5000 µg/plate, and incubated in the presence (+) and absence (−) of microsomal polysubstrate oxygenases (S-9 mixture) at 37° C. for 48 hours. After incubation, the number of revertant colonies was counted. 3 plates were prepared for each test and the average was calculated. The results are demonstrated in Tables 8 and 9.

TABLE 8

| Test Strain | Material | Dosage (µg/Plate) | Colony/Plate S-9 Mixture (−) | Colony/Plate S-9 Mixture (+) |
|---|---|---|---|---|
| TA100 | Colchicine | 0 | 121 | 103 |
| | | 317.5 | 115 | 79 |
| | | 625 | 110 | 76 |
| | | 1250 | 112 | 100 |
| | | 2500 | 115 | 91 |
| | | 5000 | 108 | 78 |
| TA1525 | Colchicine | 0 | 14 | 13 |
| | | 317.5 | 18 | 13 |
| | | 625 | 15 | 13 |
| | | 1250 | 17 | 7 |
| | | 2500 | 17 | 12 |
| | | 5000 | 13 | 10 |
| TA98 | Colchicine | 0 | 31 | 35 |
| | | 317.5 | 29 | 37 |
| | | 625 | 29 | 32 |
| | | 1250 | 29 | 33 |
| | | 2500 | 24 | 37 |
| | | 5000 | 26 | 28 |
| TA1537 | Colchicine | 0 | 10 | 14 |
| | | 317.5 | 17 | 20 |
| | | 625 | 14 | 18 |
| | | 1250 | 10 | 18 |
| | | 2500 | 8 | 21 |
| | | 5000 | 9 | 21 |
| *E. coli* WP2 uvrA | Colchicine | 0 | 11 | 10 |
| | | 317.5 | 10 | 11 |
| | | 625 | 6 | 14 |
| | | 1250 | 11 | 14 |
| | | 2500 | 10 | 12 |
| | | 5000 | 11 | 8 |
| Positive control group | | | | |
| TA100 | Sodium azide | 0.5 | 453 | 616 |
| TA1535 | Sodium azide | 0.5 | 279 | 444 |
| TA98 | 4NQO | 0.5 | 488 | 391 |
| TA1537 | 9-AA | 50 | 175 | 588 |
| WP2 uvrA | 4NQO | 0.5 | 268 | 653 |

TABLE 9

| Test Strain | Material | Dosage (µg/Plate) | Colony/Plate S-9 Mixture (−) | Colony/Plate S-9 Mixture (+) |
|---|---|---|---|---|
| TA100 | Compound 6 | 0 | 95 | 104 |
| | | 317.5 | 81 | 96 |
| | | 625 | 77 | 84 |
| | | 1250 | 84 | 81 |
| | | 2500 | 88 | 77 |
| | | 5000 | 79 | 78 |
| TA1525 | Compound 6 | 0 | 12 | 10 |
| | | 317.5 | 14 | 14 |
| | | 625 | 18 | 12 |
| | | 1250 | 15 | 11 |
| | | 2500 | 10 | 11 |
| | | 5000 | 13 | 9 |
| TA98 | Compound 6 | 0 | 28 | 36 |
| | | 317.5 | 21 | 32 |
| | | 625 | 32 | 29 |
| | | 1250 | 24 | 33 |
| | | 2500 | 22 | 22 |
| | | 5000 | 19 | 23 |
| TA1537 | Compound 6 | 0 | 10 | 15 |
| | | 317.5 | 8 | 11 |
| | | 625 | 10 | 16 |
| | | 1250 | 16 | 13 |
| | | 2500 | 11 | 17 |
| | | 5000 | 7 | 14 |
| *E. coli* WP2 uvrA | Compound 6 | 0 | 11 | 10 |
| | | 317.5 | 16 | 12 |
| | | 625 | 9 | 12 |
| | | 1250 | 10 | 12 |
| | | 2500 | 8 | 9 |
| | | 5000 | 11 | 13 |
| Positive Control group | | | | |
| TA100 | Sodium azide | 0.5 | 453 | 616 |
| TA1535 | Sodium azide | 0.5 | 279 | 444 |
| TA98 | 4NQO | 0.5 | 488 | 391 |
| TA1537 | 9-AA | 50 | 175 | 588 |
| WP2 uvrA | 4NQO | 0.5 | 268 | 653 |

As shown in Tables 8 and 9, the colchicine derivatives according to the present invention induced noticeably fewer revertant colonies than the positive control groups, implying no significant hazard as mutagens.

Industrial Applicability

As described above, the novel colchicine derivative of the formula I according to the present invention or pharmaceutically acceptable salts thereof are superior to conventional colchicine in view of anticancer, anti-proliferous and immunosuppressive effects, and have less likelihood of toxicity and less hazard as mutagen than conventional colchicine.

What is claimed is:

1. Colchicine derivative of the following formula (I) and pharmaceutically acceptable salts thereof:

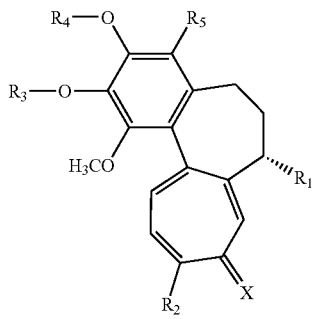

wherein:
when $R_1$ is $N(R6)$-A, $N(A)_2$ or $X_2$-A,
$R_2$ is $X_3R_7$,
$R_3$ and $R_4$ are independently hydrogen or a methyl group,
$R_5$ is hydrogen, or a methyl group,
wherein $R_6$ and $R_7$ are independently hydrogen or a lower alkyl group,
X, $X_1$, and $X_3$ are independently O or S, and $X_2$ is S;
when $R_2$ is $X_2C(X_1)$-A or $X_2$-A,
$R_1$ is $N(R_6)COCH_3$, $N(R_6)COCF_3$, or $NHC(O)OR_8$,
$R_3$ and $R_4$ are independently hydrogen or a methyl group,
$R_5$ is hydrogen or a methyl group,
wherein $R_6$ is hydrogen or a lower alkyl group,
$R_8$ is a lower alkyl, alkenyl, or substituted or unsubstituted aryl, and
X, $X_1$ and $X_2$ are independently O or S;
when $R_3$ and $R_4$ are independently $C(X_1)$-A or -A,
$R_1$ is $N(R_6)COCH_3$, $N(R_6)COCF_3$, or $NHC(O)OR_8$,
$R_2$ is $X_3R_7$,
$R_5$ is hydrogen or a methyl group,
wherein $R_6$ and $R_7$ are independently hydrogen or a lower alkyl group,
$R_8$ is a lower alkyl, alkenyl, or substituted or unsubstituted aryl, and
X, $X_1$ and $X_3$ are independently O or S;
wherein A is represented by the formula (a), (b), (c), (d), (e), (f), (g), (h), (i) or (j):

—$Y_1$—Hal (a)

—$Y_1$—$ONO_2$ (b)

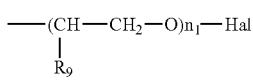 (c)

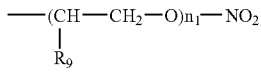 (d)

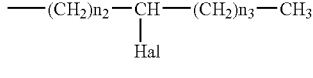 (e)

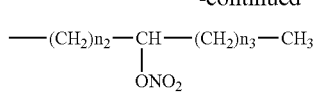 (f)

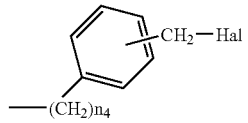 (g)

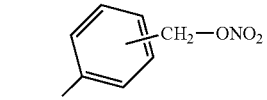 (h)

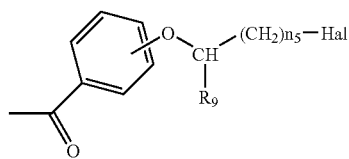 (i)

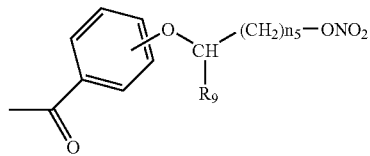 (j)

wherein $Y_1$ is a $C_3$ to $C_{10}$ straight chain or branched alkyl or a substituted $C_5$ to $C_7$ cycloalkyl group; Hal is halogen;
$R_9$ is hydrogen or a lower alkyl group;
$n_1$ is an integer from 1 to 6;
$n_2$ and $n_3$ are independently an integer from 1 to 5;
$n_4$ is an integer from 0 to 3; and
$n_5$ is an integer from 1 to 6.

2. A compound selected from the group consisting of:
4-chloro-N-(1,2,3,10-tetramethoxy-9-oxo-5,6,7,9-tetrahydro-benzo[a]heptarene-7-yl)-butylamide;
4-chloromethyl-N-(1,2,3,10-tetramethoxy-9-oxo-5,6,7,9-tetrahydro-benzo[a]heptarene-7-yl)-benzamide;
3-chloromethyl-N-(1,2,3,10-tetramethoxy-9-oxo-5,6,7,9-tetrahydro-benzo[a]heptarene-7-yl)-benzamide;
4-iodo-N-(1,2,3,10-tetramethoxy-9-oxo-5,6,7,9-tetrahydro-benzo[a]heptarene-7-yl)butylamide;
4-nitrooxy-N-(1,2,3,10-tetramethoxy-9-oxo-5,6,7,9-tetrahydro-benzo[a]heptarene-7-yl)-butylamide;
4-iodomethyl-N-(1,2,3,10-tetramethoxy-9-oxo-5,6,7,9-tetrahydro-benzo[a]heptarene-7-yl)-benzamide;
4-nitrooxymethyl-N-(1,2,3,10-tetramethoxy-9-oxo-5,6,7,9-tetrahydro-benzo[a]heptarene-7-yl)-benzamide;
3-iodomethyl-N-(1,2,3,10-tetramethoxy-9-oxo-5,6,7,9-tetrahydro-benzo[a]heptarene-7-yl)-benzamide;
3-nitrooxymethyl-N-(1,2,3,10-tetramethoxy-9-oxo-5,6,7,9-tetrahydro-benzo[a]heptarene-7-yl)-benzamide;
4-chloro-N-(1,2,3-trimethoxy-10-methylsulfanyl-9-oxo-5,6,7,9-tetrahydro-benzo[a]heptarene-7-yl)-butylamide;
4-chloromethyl-N-(1,2,3-trimethoxy-10-methylsulfanyl-9-oxo-5,6,7,9-tetrahydro-benzo[a]heptarene-7-yl)-benzamide;
3-chloromethyl-N-(1,2,3-trimethoxy-10-methylsulfanyl-9-oxo-5,6,7,9-tetrahydro-benzo[a]heptarene-7-yl)-benzamide;

4-iodo-N-(1,2,3-trimethoxy-10-methylsulfanyl-9-oxo-5,6,7,9-tetrahydro-benzo[a]heptarene-7-yl)-butylamide;

4-nitrooxy-N-(1,2,3-trimethoxy-10-methylsulfanyl-9-oxo-5,6,7,9-tetrahydro-benzo[a]heptarene-7-yl)-butylamide;

4-iodomethyl-N-(1,2,3-trimethoxy-10-methylsulfanyl-9-oxo-5,6,7,9-tetrahydro-benzo[a]heptarene-7-yl)-benzamide;

4-nitrooxymethyl-N-(1,2,3-trimethoxy-10-methylsulfanyl-9-oxo-5,6,7,9-tetrahydro-benzo[a]heptarene-7-yl)-benzamide;

3-iodomethyl-N-(1,2,3-trimethoxy-10-methylsulfanyl-9-oxo-5,6,7,9-tetrahydro-benzo[a]heptarene-7-yl)-benzamide;

3-nitrooxymethyl-N-(1,2,3-trimethoxy-10-methylsulfanyl-9-oxo-5,6,7,9-tetrahydro-benzo[a]heptarene7-yl)-benzamide;

4-chloro-N-methyl-N-(1,2,3-trimethoxy-10-methylsulfanyl-9-oxo-5,6,7,9-tetrahydro-benzo[a]heptarene-7-yl)-butylamide;

4-nitrooxymethyl-N-methyl-N-(1,2,3-trimethoxy-10-methylsulfanyl-9-oxo-5,6,7,9-tetrahydro-benzo[a]heptarene-7-yl)-benzamide;

3-nitrooxymethyl-N-methyl-N-(1,2,3-trimethoxy-10-methylsulfanyl-9-oxo-5,6,7,9-tetrahydro-benzo[a]heptarene-7-yl)-benzamide;

4-chloro-N-methyl-N-(1,2,3,10-tetramethoxy-9-oxo-5,6,7,9-tetrahydro-benzo[a]heptarene-7-yl)butylamide;

4-chloromethyl-N-methyl-N-(1,2,3,10-tetramethoxy-9-oxo-5,6,7,9-tetrahydro-benzo[a]heptarene-7-yl)benzamide;

N-methyl-4-nitrooxy-N-(1,2,3,10-tetramethoxy-9-oxo-5,6,7,9-tetrahydro-benzo[a]heptarene-7-yl)butylamide;

N-methyl-4-nitrooxymethyl-N-(1,2,3,10-tetramethoxy-9-oxo-5,6,7,9-tetrahydro-benzo[a]heptarene-7-yl)benzamide;

or pharmaceutically acceptable salts thereof.

3. A pharmaceutical composition comprising the colchicine derivative or its pharmaceutically acceptable salt according to claim 1.

4. A pharmaceutical composition comprising a colchicine derivative or its pharmaceutically acceptable salt according to claim 2 as an active ingredient.

5. A method for providing an anti-inflammatory effect comprising administering to a patient in need of such an effect an effective amount of a colchicine derivative according to claim 1.

6. A method for providing an immunosuppressive effect comprising administering to a patient in need of such an effect an effective amount of a colchicine derivative according to claim 1.

* * * * *